US010041088B2

(12) United States Patent
Schultheiss et al.

(10) Patent No.: US 10,041,088 B2
(45) Date of Patent: Aug. 7, 2018

(54) FUNGAL RESISTANT PLANTS EXPRESSING CASAR

(71) Applicant: BASF PLANT SCIENCE COMPANY GMBH, Ludwigshafen (DE)

(72) Inventors: Holger Schultheiss, Boehl-Iggelheim (DE); Nadine Tresch, Kirchheim (DE); Ralf Flachmann, Limburgerhof (DE)

(73) Assignee: BASF PLANT SCIENCE COMPANY GMBH, Ludwigshafen (DE)

( * ) Notice: Subject to any disclaimer, the term of this patent is extended or adjusted under 35 U.S.C. 154(b) by 161 days.

(21) Appl. No.: 14/442,256

(22) PCT Filed: Nov. 7, 2013

(86) PCT No.: PCT/IB2013/059971
§ 371 (c)(1),
(2) Date: May 12, 2015

(87) PCT Pub. No.: WO2014/076614
PCT Pub. Date: May 22, 2014

(65) Prior Publication Data

US 2016/0272996 A1 Sep. 22, 2016

(30) Foreign Application Priority Data

Nov. 13, 2012 (EP) .................................... 12192316

(51) Int. Cl.
*C12N 15/82* (2006.01)
*C07K 14/415* (2006.01)

(52) U.S. Cl.
CPC ........ *C12N 15/8282* (2013.01); *C07K 14/415* (2013.01); *C12N 15/8239* (2013.01)

(58) Field of Classification Search
None
See application file for complete search history.

(56) References Cited

U.S. PATENT DOCUMENTS 5,856,154 A 1/1999 Ryals et al.
2010/0071089 A1* 3/2010 Frank ................. C12N 15/8282 800/279
2010/0192254 A1 7/2010 Frank et al.

FOREIGN PATENT DOCUMENTS

| | | | |
|---|---|---|---|
| CN | 101511865 | A | 8/2009 |
| KR | 20030086078 | A | 11/2003 |
| WO | WO-2008/017706 | A1 | 2/2008 |
| WO | WO 2009/010460 | * | 1/2009 |
| WO | WO-2009/010460 | A2 | 1/2009 |
| WO | WO-2012/127373 | A1 | 9/2012 |

OTHER PUBLICATIONS

Lee et al (2003, Planta 216:387-396).*
Lee et al. 2003 Planta 216: 387-396.*
Guo et al (2004, Proc. Natl. Acad. Sci. USA 101: 9205-9210).*
Lee et al (2006, Plant Mol. Biol. 61:95-109).*
European Search Report for Application No. EP/12192316 dated Apr. 12, 2013.
Frederick et al., "Polymerase chain reaction assays for the detection and discrimination of the soybean rust pathogens *Phakopsora pachyrhizi* and *P. meibomiae*", *Phytopathology*, 92(2) :217-227 (2002).
GenBank Accession No. AF112868, "*Capsicum annuum* SAR8.2 precursor (Sar82A) mRNA, complete cds" dated May 13, 2004.
Godoy et al., "Diagrammatic scale for assessment of soybean rust severity", *Fitopatol. Bras*. 31(1):63-68 (2006).
Heath et al., "Cellular interactions between biotrophic fungal pathogens and host or nonhost plants", *Can. J. Plant Pathol*. 24 :259-264 (2002).
International Search Report and Written Opinion for Application No. PCT/IB2013/059971 dated Nov. 7, 2013.
Lee et al., "CASAR82A, a pathogen-induced pepper SAR8.2, exhibits an antifungal activity and its overexpression enhances disease resistance and stress tolerance", *Plant Molecular Biology*, 61: 95-109 (2006).
Lee et al., "Induction of some defense-related genes and oxidative burst is required for the establishment of systematic acquired resistance in *Capsicum annuum", Planta*, 221: 790-800 (2005).
Morillo et al., "Functional analysis of receptor-like kinases in monocots and dicots", *Current Opinion in Plant Biology*, 9:460-469 (2006).
Neu et al., "Cytological and molecular analysis of the *Hordeum vulgare-Puccinia triticina* nonhost interaction", *MPMI* 16(7): 626-33 (2003).
Rytter et al., "Additional alternative hosts of *Phakopsora pachyrhizi*, causal agent of soybean rust", *Plant Dis*. 68(9):818-819 (1984).
Shan et al., "Identification of a SAR8.2 gene in the susceptible host response of *Nicotiana benthamiana* to *Colletotrichum orbiculare", Functional Plant Biology*, 32:259-266 (2005).
Sinclair et al., (eds.) Proceedings of the Soybean Rust Workshop, Aug. 9-11, 1995. Urbana, IL: National Soybean Research Laboratory, (1995).

* cited by examiner

*Primary Examiner* — Anne Kubelik
(74) *Attorney, Agent, or Firm* — Marshall, Gerstein & Borun LLP

(57) ABSTRACT

The present invention relates to a method of increasing resistance against fungal pathogens of the order Pucciniales, preferably the family Phacopsoraceae, in plants and/or plant cells. This is achieved by increasing the expression of a CASAR protein or fragment thereof in a plant, plant part and/or plant cell in comparison to wild type plants, wild type plant parts and/or wild type plant cells. Furthermore, the invention relates to transgenic plants, plant parts, and/or plant cells having an increased resistance against fungal pathogens, in particular, pathogens of the order Pucciniales, preferably the family Phacopsoraceae, and to recombinant expression vectors comprising a sequence that is identical or homologous to a sequence encoding a CASAR protein.

15 Claims, 6 Drawing Sheets

Figure 4:

Figures 4, 5, 6, 7:
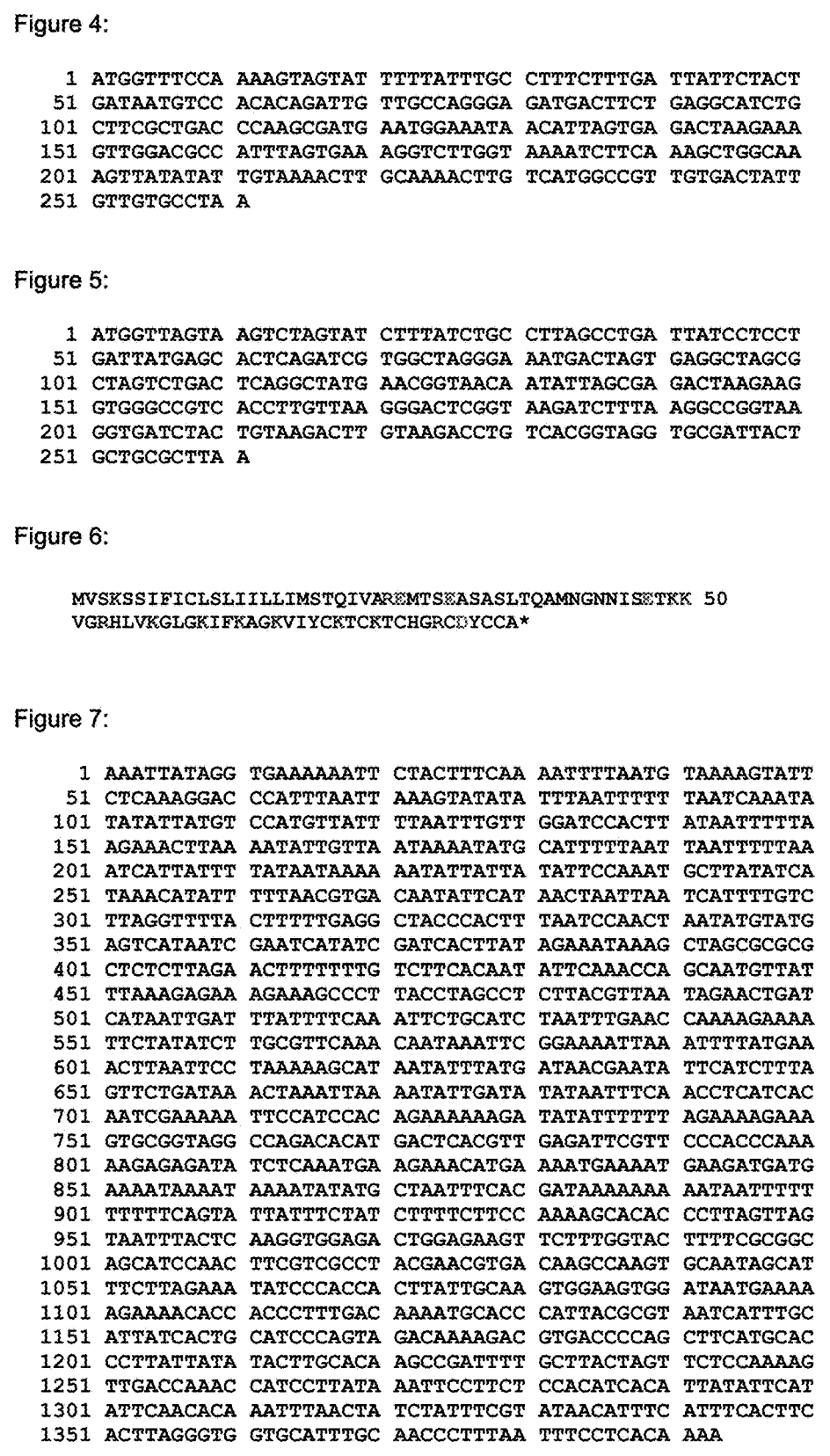

1 ATGGTTTCCA AAAGTAGTAT TTTTATTTGC CTTTCTTTGA TTATTCTACT
51 GATAATGTCC ACACAGATTG TTGCCAGGGA GATGACTTCT GAGGCATCTG
101 CTTCGCTGAC CCAAGCGATG AATGGAAATA ACATTAGTGA GACTAAGAAA
151 GTTGGACGCC ATTTAGTGAA AGGTCTTGGT AAAATCTTCA AAGCTGGCAA
201 AGTTATATAT TGTAAAACTT GCAAAACTTG TCATGGCCGT TGTGACTATT
251 GTTGTGCCTA A

Figure 5:

1 ATGGTTAGTA AGTCTAGTAT CTTTATCTGC CTTAGCCTGA TTATCCTCCT
51 GATTATGAGC ACTCAGATCG TGGCTAGGGA AATGACTAGT GAGGCTAGCG
101 CTAGTCTGAC TCAGGCTATG AACGGTAACA ATATTAGCGA GACTAAGAAG
151 GTGGGCCGTC ACCTTGTTAA GGGACTCGGT AAGATCTTTA AGGCCGGTAA
201 GGTGATCTAC TGTAAGACTT GTAAGACCTG TCACGGTAGG TGCGATTACT
251 GCTGCGCTTA A

Figure 6:

MVSKSSIFICLSLIILLIMSTQIVAR[illegible]MTS[illegible]ASASLTQAMNGNNIS[illegible]TKK 50
VGRHLVKGLGKIFKAGKVIYCKTCKTCHGRCDYCCA*

Figure 7:

1 AAATTATAGG TGAAAAAATT CTACTTTCAA AATTTTAATG TAAAAGTATT
51 CTCAAAGGAC CCATTTAATT AAAGTATATA TTTAATTTTT TAATCAAATA
101 TATATTATGT CCATGTTATT TTAATTTGTT GGATCCACTT ATAATTTTTA
151 AGAAACTTAA AATATTGTTA ATAAAATATG CATTTTTAAT TAATTTTTAA
201 ATCATTATTT TATAATAAAA AATATTATTA TATTCCAAAT GCTTATATCA
251 TAAACATATT TTTAACGTGA CAATATTCAT AACTAATTAA TCATTTTGTC
301 TTAGGTTTTA CTTTTTGAGG CTACCCACTT TAATCCAACT AATATGTATG
351 AGTCATAATC GAATCATATC GATCACTTAT AGAAATAAAG CTAGCGCGCG
401 CTCTCTTAGA ACTTTTTTTG TCTTCACAAT ATTCAAACCA GCAATGTTAT
451 TTAAAGAGAA AGAAAGCCCT TACCTAGCCT CTTACGTTAA TAGAACTGAT
501 CATAATTGAT TTATTTTCAA ATTCTGCATC TAATTTGAAC CAAAAGAAAA
551 TTCTATATCT TGCGTTCAAA CAATAAATTC GGAAAATTAA ATTTTATGAA
601 ACTTAATTCC TAAAAAGCAT AATATTTATG ATAACGAATA TTCATCTTTA
651 GTTCTGATAA ACTAAATTAA AATATTGATA TATAATTTCA ACCTCATCAC
701 AATCGAAAAA TTCCATCCAC AGAAAAAAGA TATATTTTTT AGAAAAGAAA
751 GTGCGGTAGG CCAGACACAT GACTCACGTT GAGATTCGTT CCCACCCAAA
801 AAGAGAGATA TCTCAAATGA AGAAACATGA AAATGAAAAT GAAGATGATG
851 AAAATAAAAT AAAATATATG CTAATTTCAC GATAAAAAAA AATAATTTTT
901 TTTTTCAGTA TTATTTCTAT CTTTTCTTCC AAAAGCACAC CCTTAGTTAG
951 TAATTTACTC AAGGTGGAGA CTGGAGAAGT TCTTTGGTAC TTTTCGCGGC
1001 AGCATCCAAC TTCGTCGCCT ACGAACGTGA CAAGCCAAGT GCAATAGCAT
1051 TTCTTAGAAA TATCCCACCA CTTATTGCAA GTGGAAGTGG ATAATGAAAA
1101 AGAAAACACC ACCCTTTGAC AAAATGCACC CATTACGCGT AATCATTTGC
1151 ATTATCACTG CATCCCAGTA GACAAAAGAC GTGACCCCAG CTTCATGCAC
1201 CCTTATTATA TACTTGCACA AGCCGATTTT GCTTACTAGT TCTCCAAAAG
1251 TTGACCAAAC CATCCTTATA AATTCCTTCT CCACATCACA TTATATTCAT
1301 ATTCAACACA AATTTAACTA TCTATTTCGT ATAACATTTC ATTTCACTTC
1351 ACTTAGGGTG GTGCATTTGC AACCCTTTAA TTTCCTCACA AAA

Figure 8:

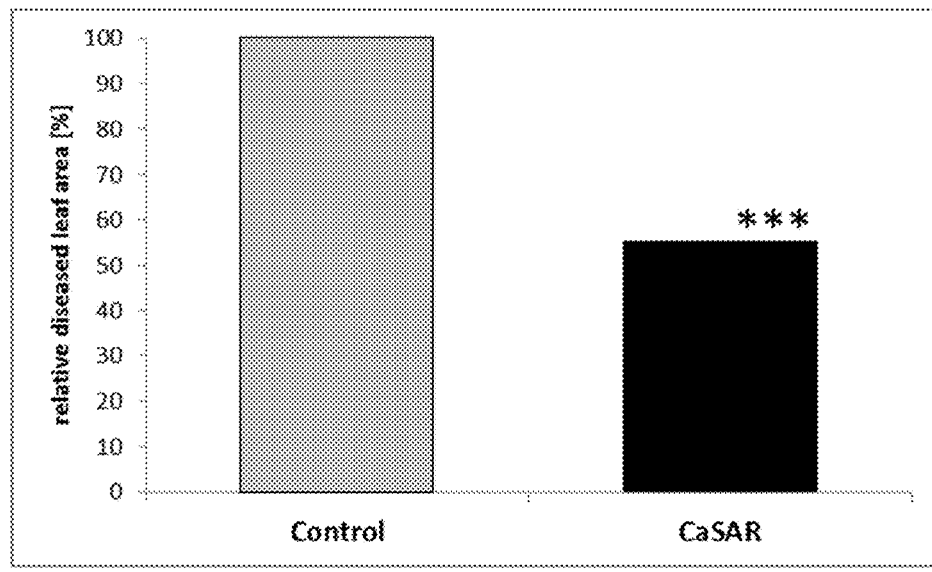

Figure 9:

| SEQ ID NO: | Description of the sequence listing |
|---|---|
| SEQ ID NO:1 | Nucleotide sequence CASAR; *Capsicum annuum* |
| SEQ ID NO:2 | Nucleotide sequence CASAR; *Capsicum annuum,* codon optimized |
| SEQ ID NO:3 | Amino acid sequence CASAR; *Capsicum annuum* |
| SEQ ID NO:4 | Nucleotide sequence of promoter the pGm rust induced mesophyll specific promoter 820 |
| SEQ ID NO:5 | Nucleotide sequence CASAR, variant 1 |
| SEQ ID NO:6 | Nucleotide sequence CASAR, variant 2 |
| SEQ ID NO:7 | Nucleotide sequence CASAR, variant 3 |
| SEQ ID NO:8 | Nucleotide sequence CASAR, variant 4 |
| SEQ ID NO:9 | Nucleotide sequence CASAR, variant 5 |
| SEQ ID NO:10 | Nucleotide sequence CASAR, variant 6 |
| SEQ ID NO:11 | Nucleotide sequence CASAR, variant 7 |
| SEQ ID NO:12 | Nucleotide sequence CASAR, variant 8 |
| SEQ ID NO:13 | Nucleotide sequence CASAR, variant 9 |
| SEQ ID NO:14 | Amino acid sequence CASAR, variant 9 |

Figure 9 continued:

| SEQ ID NO: | Description of the sequence listing |
|---|---|
| SEQ ID NO:15 | Nucleotide sequence CASAR, variant 10 |
| SEQ ID NO:16 | Amino acid sequence CASAR, variant 10 |
| SEQ ID NO:17 | Nucleotide sequence CASAR, variant 11 |
| SEQ ID NO:18 | Amino acid sequence CASAR, variant 11 |
| SEQ ID NO:19 | Nucleotide sequence CASAR, variant 12 |
| SEQ ID NO:20 | Amino acid sequence CASAR, variant 12 |
| SEQ ID NO:21 | Nucleotide sequence CASAR, variant 13 |
| SEQ ID NO:22 | Amino acid sequence CASAR, variant 13 |
| SEQ ID NO:23 | Nucleotide sequence CASAR, variant 14 |
| SEQ ID NO:24 | Amino acid sequence CASAR, variant 14 |
| SEQ ID NO:25 | Nucleotide sequence CASAR, variant 15 |
| SEQ ID NO:26 | Amino acid sequence CASAR, variant 15 |
| SEQ ID NO:27 | Nucleotide sequence CASAR, variant 16 |
| SEQ ID NO:28 | Amino acid sequence CASAR, variant 16 |

SEQUENCE LISTING

```
<160> NUMBER OF SEQ ID NOS: 28

<210> SEQ ID NO 1
<211> LENGTH: 261
<212> TYPE: DNA
<213> ORGANISM: Capsicum annuum
<220> FEATURE:
<221> NAME/KEY: source
<222> LOCATION: (1)..(261)
<223> OTHER INFORMATION: /organism="Capsicum annuum" /note="Nucleotide
      sequence CASAR" /mol_type="unassigned DNA"

<400> SEQUENCE: 1

atggtttcca aaagtagtat ttttatttgc ctttctttga ttattctact gataatgtcc      60

acacagattg ttgccaggga gatgacttct gaggcatctg cttcgctgac ccaagcgatg     120

aatggaaata acattagtga gactaagaaa gttggacgcc atttagtgaa aggtcttggt     180

aaaatcttca aagctggcaa agttatatat tgtaaaactt gcaaaacttg tcatggccgt     240

tgtgactatt gttgtgccta a                                               261


<210> SEQ ID NO 2
<211> LENGTH: 261
<212> TYPE: DNA
<213> ORGANISM: Artificial Sequence
<220> FEATURE:
<223> OTHER INFORMATION: Synthetic polynucleotide
<220> FEATURE:
<221> NAME/KEY: source
<222> LOCATION: (1)..(261)
<223> OTHER INFORMATION: /organism="Artificial Sequence"
      /note="Nucleotide sequence CASAR; codon optimized"
      /mol_type="unassigned DNA"

<400> SEQUENCE: 2

atggttagta agtctagtat ctttatctgc cttagcctga ttatcctcct gattatgagc      60

actcagatcg tggctaggga aatgactagt gaggctagcg ctagtctgac tcaggctatg     120

aacggtaaca atattagcga gactaagaag gtgggccgtc accttgttaa gggactcggt     180

aagatcttta aggccggtaa ggtgatctac tgtaagactt gtaagacctg tcacggtagg     240

tgcgattact gctgcgctta a                                               261


<210> SEQ ID NO 3
<211> LENGTH: 86
<212> TYPE: PRT
<213> ORGANISM: Capsicum annuum
<220> FEATURE:
<221> NAME/KEY: source
<222> LOCATION: (1)..(86)
<223> OTHER INFORMATION: Amino acid sequence CASAR

<400> SEQUENCE: 3
```

```
Met Val Ser Lys Ser Ser Ile Phe Ile Cys Leu Ser Leu Ile Ile Leu
1               5                   10                  15

Leu Ile Met Ser Thr Gln Ile Val Ala Arg Glu Met Thr Ser Glu Ala
            20                  25                  30

Ser Ala Ser Leu Thr Gln Ala Met Asn Gly Asn Asn Ile Ser Glu Thr
        35                  40                  45

Lys Lys Val Gly Arg His Leu Val Lys Gly Leu Gly Lys Ile Phe Lys
    50                  55                  60

Ala Gly Lys Val Ile Tyr Cys Lys Thr Cys Lys Thr Cys His Gly Arg
65                  70                  75                  80

Cys Asp Tyr Cys Cys Ala
                85


<210> SEQ ID NO 4
<211> LENGTH: 1393
<212> TYPE: DNA
<213> ORGANISM: Glycine max
<220> FEATURE:
<221> NAME/KEY: source
<222> LOCATION: (1)..(1393)
<223> OTHER INFORMATION: /organism="Glycine max" /note="rust induced
      mesophyll specific promoter 820" /mol_type="unassigned DNA"

<400> SEQUENCE: 4

aaattatagg tgaaaaaatt ctactttcaa aattttaatg taaaagtatt ctcaaaggac      60

ccatttaatt aaagtatata tttaattttt taatcaaata tatattatgt ccatgttatt     120

ttaatttgtt ggatccactt ataattttta agaaacttaa aatattgtta ataaaatatg     180

catttttaat taatttttaa atcattattt tataataaaa aatattatta tattccaaat     240

gcttatatca taaacatatt tttaacgtga caatattcat aactaattaa tcattttgtc     300

ttaggtttta ctttttgagg ctacccactt taatccaact aatatgtatg agtcataatc     360

gaatcatatc gatcacttat agaaataaag ctagcgcgcg ctctcttaga acttttttg      420

tcttcacaat attcaaacca gcaatgttat ttaaagagaa agaaagccct tacctagcct     480

cttacgttaa tagaactgat cataattgat ttattttcaa attctgcatc taatttgaac     540

caaaagaaaa ttctatatct tgcgttcaaa caataaattc ggaaaattaa attttatgaa     600

acttaattcc taaaaagcat aatatttatg ataacgaata ttcatcttta gttctgataa     660

actaaattaa aatattgata tataatttca acctcatcac aatcgaaaaa ttccatccac     720

agaaaaaaga tatatttttt agaaaagaaa gtgcggtagg ccagacacat gactcacgtt     780

gagattcgtt cccacccaaa aagagagata tctcaaatga agaaacatga aaatgaaaat     840

gaagatgatg aaaataaaat aaaatatatg ctaatttcac gataaaaaaa aataattttt     900

tttttcagta ttatttctat cttttcttcc aaaagcacac ccttagttag taatttactc     960

aaggtggaga ctggagaagt tctttggtac ttttcgcggc agcatccaac ttcgtcgcct    1020

acgaacgtga caagccaagt gcaatagcat ttcttagaaa tatcccacca cttattgcaa    1080

gtggaagtgg ataatgaaaa agaaaacacc accctttgac aaaatgcacc cattacgcgt    1140

aatcatttgc attatcactg catcccagta gacaaaagac gtgaccccag cttcatgcac    1200

ccttattata tacttgcaca agccgatttt gcttactagt tctccaaaag ttgaccaaac    1260

catccttata aattccttct ccacatcaca ttatattcat attcaacaca aatttaacta    1320

tctatttcgt ataacatttc atttcacttc acttagggtg gtgcatttgc aaccctttaa    1380

tttcctcaca aaa                                                       1393
```

```
<210> SEQ ID NO 5
<211> LENGTH: 261
<212> TYPE: DNA
<213> ORGANISM: Artificial Sequence
<220> FEATURE:
<223> OTHER INFORMATION: Synthetic polynucleotide
<220> FEATURE:
<221> NAME/KEY: source
<222> LOCATION: (1)..(261)
<223> OTHER INFORMATION: /organism="Artificial Sequence"
      /note="Nucleotide sequence CASAR, variant 1"
      /mol_type="unassigned DNA"

<400> SEQUENCE: 5

atggtgtcaa aatcgtctat ttttatctgt ttgtcaatga taattttact gataatgtca     60

acacaaatag tagcgcgaga gatgacgtca gaagcatccg cgagcatgac ccaagcaatg    120

aatgggaata acatatcgga aacaaaaaaa gtaggacgcc atctagtaaa ggggttgggg    180

aaaatattca aagcggggaa agtcatatat tgcaaaacat gcaaaacgtg ccatggccgg    240

tgtgactatt gttgtgcatg a                                               261


<210> SEQ ID NO 6
<211> LENGTH: 261
<212> TYPE: DNA
<213> ORGANISM: Artificial Sequence
<220> FEATURE:
<223> OTHER INFORMATION: Synthetic polynucleotide
<220> FEATURE:
<221> NAME/KEY: source
<222> LOCATION: (1)..(261)
<223> OTHER INFORMATION: /organism="Artificial Sequence"
      /note="Nucleotide sequence CASAR, variant 2"
      /mol_type="unassigned DNA"

<400> SEQUENCE: 6

atggttagta aatcgagtat attcatttgc ctgagcatga taattcttat gattatgagt     60

actcaaatag tcgcccgaga gatgacgtca gaagcgtccg cttctatgac gcaggccatg    120

aacgggaata acatctcgga gaccaaaaaa gtaggacgtc atcttgtaaa aggtctagga    180

aaaatcttca aagcggggaa agtgatttac tgcaaaactt gcaaaacatg ccatgggcgt    240

tgtgactatt gttgtgcatg a                                               261


<210> SEQ ID NO 7
<211> LENGTH: 261
<212> TYPE: DNA
<213> ORGANISM: Artificial Sequence
<220> FEATURE:
<223> OTHER INFORMATION: Synthetic polynucleotide
<220> FEATURE:
<221> NAME/KEY: source
<222> LOCATION: (1)..(261)
<223> OTHER INFORMATION: /organism="Artificial Sequence"
      /note="Nucleotide sequence CASAR, variant 3"
      /mol_type="unassigned DNA"

<400> SEQUENCE: 7

atggtaagta aatctagtat cttcatatgt ttatctatga ttattctgct gattatgagc     60

actcagatcg tggctcggga gatgacaagt gaagcatctg ctagcatgac gcaagccatg    120

aacggtaata atataagcga aacaaaaaaa gttgggcgtc atcttgttaa aggtctaggc    180

aaaatcttta aagcgggtaa agtgatttat tgcaagacct gtaaaacatg ccatggcagg    240

tgtgactact gttgtgccta g                                               261
```

<210> SEQ ID NO 8
<211> LENGTH: 261
<212> TYPE: DNA
<213> ORGANISM: Artificial Sequence
<220> FEATURE:
<223> OTHER INFORMATION: Synthetic polynucleotide
<220> FEATURE:
<221> NAME/KEY: source
<222> LOCATION: (1)..(261)
<223> OTHER INFORMATION: /organism="Artificial Sequence"
/note="Nucleotide sequence CASAR, variant 4"
/mol_type="unassigned DNA"

<400> SEQUENCE: 8

```
atggtgtcga agtcttcgat cttcatatgt ctaagtatga ttatacttct gattatgagc     60

actcaaattg tggctaggga gatgacctca gaagcaagcg ctagtatgac acaggctatg    120

aatggtaata atatttctga gaccaagaag gtaggccgtc atcttgttaa gggattgggc    180

aagatattca aggccggtaa agtgatatat tgcaagactt gcaaaacctg ccacggcagg    240

tgtgattact gctgcgcttg a                                              261
```

<210> SEQ ID NO 9
<211> LENGTH: 261
<212> TYPE: DNA
<213> ORGANISM: Artificial Sequence
<220> FEATURE:
<223> OTHER INFORMATION: Synthetic polynucleotide
<220> FEATURE:
<221> NAME/KEY: source
<222> LOCATION: (1)..(261)
<223> OTHER INFORMATION: /organism="Artificial Sequence"
/note="Nucleotide sequence CASAR, variant 5"
/mol_type="unassigned DNA"

<400> SEQUENCE: 9

```
atggttagca agagcagtat ctttatctgt cttagcatga taatcctcat gataatgagc     60

acgcagatcg tggcaaggga aatgacttca gaagctagcg ctagtctgac tcaggctatg    120

aatggtaata atattagcga gactaagaag gttggtcgtc acctggttaa gggactcgga    180

aagatttta aggccggtaa agtgatatat tgcaagactt gtaaaacctg tcacggtcgt    240

tgcgactatt gctgtgctta a                                              261
```

<210> SEQ ID NO 10
<211> LENGTH: 261
<212> TYPE: DNA
<213> ORGANISM: Artificial Sequence
<220> FEATURE:
<223> OTHER INFORMATION: Synthetic polynucleotide
<220> FEATURE:
<221> NAME/KEY: source
<222> LOCATION: (1)..(261)
<223> OTHER INFORMATION: /organism="Artificial Sequence"
/note="Nucleotide sequence CASAR, variant 6"
/mol_type="unassigned DNA"

<400> SEQUENCE: 10

```
atggttagta agtctagtat cttcatatgc cttagcatga ttatcctcat gattatgagc     60

actcagatcg tagcgcggga aatgactagt gaggccagcg ctagtctgac tcaggctatg    120

aatggcaaca atatcagcga aactaagaag gttggccgtc acctagttaa aggactcggt    180

aagatcttta aggccggtaa ggtgatctac tgcaaaacat gtaagacctg tcacggtagg    240

tgtgactact gttgcgctta a                                              261
```

<210> SEQ ID NO 11

<211> LENGTH: 261
<212> TYPE: DNA
<213> ORGANISM: Artificial Sequence
<220> FEATURE:
<223> OTHER INFORMATION: Synthetic polynucleotide
<220> FEATURE:
<221> NAME/KEY: source
<222> LOCATION: (1)..(261)
<223> OTHER INFORMATION: /organism="Artificial Sequence"
/note="Nucleotide sequence CASAR, variant 7"
/mol_type="unassigned DNA"

<400> SEQUENCE: 11

```
atggttagta agtctagtat ctttatttgc cttagcctga ttatcctcat gattatgagc     60

actcagatcg tggctaggga aatgactagt gaagctagcg ctagtctgac tcaagctatg    120

aacggtaata atatttcgga gactaagaag gtgggccgtc accttgttaa gggactcggt    180

aagatcttta aggcggggaa ggtgatctac tgcaaaactt gtaagacctg tcacggaagg    240

tgtgactact gctgcgcata a                                              261
```

<210> SEQ ID NO 12
<211> LENGTH: 261
<212> TYPE: DNA
<213> ORGANISM: Artificial Sequence
<220> FEATURE:
<223> OTHER INFORMATION: Synthetic polynucleotide
<220> FEATURE:
<221> NAME/KEY: source
<222> LOCATION: (1)..(261)
<223> OTHER INFORMATION: /organism="Artificial Sequence"
/note="Nucleotide sequence CASAR, variant 8"
/mol_type="unassigned DNA"

<400> SEQUENCE: 12

```
atggttagta agtctagtat ctttatctgc cttagcctga ttatcctcct gattatgagc     60

acgcagatcg tggccaggga aatgactagt gaggctagcg ctagtctgac gcaggctatg    120

aacggaaaca atattagcga gactaaaaag gtgggccgtc accttgttaa gggactcggt    180

aagatattca aggccggtaa ggtgatctac tgtaagactt gtaagacctg tcacggtagg    240

tgcgattact gctgtgctta a                                              261
```

<210> SEQ ID NO 13
<211> LENGTH: 258
<212> TYPE: DNA
<213> ORGANISM: Artificial Sequence
<220> FEATURE:
<223> OTHER INFORMATION: Synthetic polynucleotide
<220> FEATURE:
<221> NAME/KEY: source
<222> LOCATION: (1)..(258)
<223> OTHER INFORMATION: /organism="Artificial Sequence"
/note="Nucleotide sequence CASAR, variant 9"
/mol_type="unassigned DNA"

<400> SEQUENCE: 13

```
atgatgagca agtgctgcgg cttcatctgc ctgtgcctga tcgtgctgct gatcatgtgc     60

accaacgtga tcgccagaga gatgaccagc gaggccagca tcagcctgac ccaggccatg    120

caggccaacc agatctgcga caccaagaga gtgggcagac acatcgtgag aggcctgggc    180

agagtgttcc acgccggcca catcatctac tgcaagacct gcaagaccac ccacggcaga    240

tgcgacttct gctgcgcc                                                  258
```

<210> SEQ ID NO 14
<211> LENGTH: 86

<212> TYPE: PRT
<213> ORGANISM: Artificial Sequence
<220> FEATURE:
<223> OTHER INFORMATION: Amino acid sequence CASAR, variant 9

<400> SEQUENCE: 14

```
Met Met Ser Lys Cys Cys Gly Phe Ile Cys Leu Cys Leu Ile Val Leu
1               5                   10                  15

Leu Ile Met Cys Thr Asn Val Ile Ala Arg Glu Met Thr Ser Glu Ala
            20                  25                  30

Ser Ile Ser Leu Thr Gln Ala Met Gln Ala Asn Gln Ile Cys Asp Thr
        35                  40                  45

Lys Arg Val Gly Arg His Ile Val Arg Gly Leu Gly Arg Val Phe His
    50                  55                  60

Ala Gly His Ile Ile Tyr Cys Lys Thr Cys Lys Thr Thr His Gly Arg
65                  70                  75                  80

Cys Asp Phe Cys Cys Ala
                85
```

<210> SEQ ID NO 15
<211> LENGTH: 258
<212> TYPE: DNA
<213> ORGANISM: Artificial Sequence
<220> FEATURE:
<223> OTHER INFORMATION: Synthetic polynucleotide
<220> FEATURE:
<221> NAME/KEY: source
<222> LOCATION: (1)..(258)
<223> OTHER INFORMATION: /organism="Artificial Sequence"
/note="Nucleotide sequence CASAR, variant 10"
/mol_type="unassigned DNA"

<400> SEQUENCE: 15

```
atgggcagca agtgcagcat cttcatcacc ctgagcctga tcatcctgct gatcatgacc      60

acccagatcg tggccagaga catgaccagc gaggccagcg ccagcatcac ccaggccatc     120

aacctgcaga acctgagcga gaccaagaag ctgggcaagc acctgatcaa gggcctgctg     180

cacgcctgga aggccggcag agtgatctgg tgcagaacct gcaagacctg ccacggccac     240

tgcgactact gctgcatc                                                   258
```

<210> SEQ ID NO 16
<211> LENGTH: 86
<212> TYPE: PRT
<213> ORGANISM: Artificial Sequence
<220> FEATURE:
<223> OTHER INFORMATION: Amino acid sequence CASAR, variant 10

<400> SEQUENCE: 16

```
Met Gly Ser Lys Cys Ser Ile Phe Ile Thr Leu Ser Leu Ile Ile Leu
1               5                   10                  15

Leu Ile Met Thr Thr Gln Ile Val Ala Arg Asp Met Thr Ser Glu Ala
            20                  25                  30

Ser Ala Ser Ile Thr Gln Ala Ile Asn Leu Gln Asn Leu Ser Glu Thr
        35                  40                  45

Lys Lys Leu Gly Lys His Leu Ile Lys Gly Leu Leu His Ala Trp Lys
    50                  55                  60

Ala Gly Arg Val Ile Trp Cys Arg Thr Cys Lys Thr Cys His Gly His
65                  70                  75                  80

Cys Asp Tyr Cys Cys Ile
                85
```

```
<210> SEQ ID NO 17
<211> LENGTH: 258
<212> TYPE: DNA
<213> ORGANISM: Artificial Sequence
<220> FEATURE:
<223> OTHER INFORMATION: Synthetic polynucleotide
<220> FEATURE:
<221> NAME/KEY: source
<222> LOCATION: (1)..(258)
<223> OTHER INFORMATION: /organism="Artificial Sequence"
      /note="Nucleotide sequence CASAR, variant 11"
      /mol_type="unassigned DNA"

<400> SEQUENCE: 17

atggtgtgca agagcagcat cttcgtgtgc ctgagcctga tcggcctgct gatcatgagc     60

acccagatcg tggccagaga gatgaccagc gaggccagcg ccaccctgag ccaggccatg    120

aacggcaaca acatcaccga gacccacaag gtgggcagaa agatggtgag aggcctgctg    180

cacatctaca aggccggcaa gatcatctac tgccacacct gcaagacctg ccacatgaga    240

tgcgagtact gctgcatc                                                  258


<210> SEQ ID NO 18
<211> LENGTH: 86
<212> TYPE: PRT
<213> ORGANISM: Artificial Sequence
<220> FEATURE:
<223> OTHER INFORMATION: Amino acid sequence CASAR, variant 11

<400> SEQUENCE: 18

Met Val Cys Lys Ser Ser Ile Phe Val Cys Leu Ser Leu Ile Gly Leu
1               5                   10                  15

Leu Ile Met Ser Thr Gln Ile Val Ala Arg Glu Met Thr Ser Glu Ala
            20                  25                  30

Ser Ala Thr Leu Ser Gln Ala Met Asn Gly Asn Asn Ile Thr Glu Thr
        35                  40                  45

His Lys Val Gly Arg Lys Met Val Arg Gly Leu Leu His Ile Tyr Lys
    50                  55                  60

Ala Gly Lys Ile Ile Tyr Cys His Thr Cys Lys Thr Cys His Met Arg
65                  70                  75                  80

Cys Glu Tyr Cys Cys Ile
                85


<210> SEQ ID NO 19
<211> LENGTH: 258
<212> TYPE: DNA
<213> ORGANISM: Artificial Sequence
<220> FEATURE:
<223> OTHER INFORMATION: Synthetic polynucleotide
<220> FEATURE:
<221> NAME/KEY: source
<222> LOCATION: (1)..(258)
<223> OTHER INFORMATION: /organism="Artificial Sequence"
      /note="Nucleotide sequence CASAR, variant 12"
      /mol_type="unassigned DNA"

<400> SEQUENCE: 19

atggtgagca agagcagcat cttcatcagc ctgagcctga tcatcctgct gatcctgagc     60

acccagatcg tggccagaga gatgaccagc gagctgagcg ccagcctgac ccaggccatg    120

aacggcaaca acatcagcga gaccagaaag gtggccagaa agctggtgaa gggcctgggc    180

aagatgtgga agggcggcaa ggtgatcttc tgccactgct gcaagacctg ccacggcaga    240

tgcgactact gctgcctg                                                  258
```

<210> SEQ ID NO 20
<211> LENGTH: 86
<212> TYPE: PRT
<213> ORGANISM: Artificial Sequence
<220> FEATURE:
<223> OTHER INFORMATION: Amino acid sequence CASAR, variant 12

<400> SEQUENCE: 20

```
Met Val Ser Lys Ser Ser Ile Phe Ile Ser Leu Ser Leu Ile Ile Leu
1               5                   10                  15

Leu Ile Leu Ser Thr Gln Ile Val Ala Arg Glu Met Thr Ser Glu Leu
            20                  25                  30

Ser Ala Ser Leu Thr Gln Ala Met Asn Gly Asn Asn Ile Ser Glu Thr
        35                  40                  45

Arg Lys Val Ala Arg Lys Leu Val Lys Gly Leu Gly Lys Met Trp Lys
    50                  55                  60

Gly Gly Lys Val Ile Phe Cys His Cys Cys Lys Thr Cys His Gly Arg
65                  70                  75                  80

Cys Asp Tyr Cys Cys Leu
                85
```

<210> SEQ ID NO 21
<211> LENGTH: 258
<212> TYPE: DNA
<213> ORGANISM: Artificial Sequence
<220> FEATURE:
<223> OTHER INFORMATION: Synthetic polynucleotide
<220> FEATURE:
<221> NAME/KEY: source
<222> LOCATION: (1)..(258)
<223> OTHER INFORMATION: /organism="Artificial Sequence"
/note="Nucleotide sequence CASAR, variant 13"
/mol_type="unassigned DNA"

<400> SEQUENCE: 21

```
atggtgagca agagctgcat cttcatctgc ctgagcctga tcatcctgct gatcatgagc     60

acccagatcg tggccagaga gctgtgcagc gaggccagcg ccagcctgtg ccaggccatg    120

aacggcaaca acatcagcga gaccaagaag gtgggcagac acctggtgaa gggcctgggc    180

aagatcttcc acgccggcaa ggtgatctac tgcaagacct gcaagagctg ccacggcaga    240

tgcgagtact gctgcgcc                                                  258
```

<210> SEQ ID NO 22
<211> LENGTH: 86
<212> TYPE: PRT
<213> ORGANISM: Artificial Sequence
<220> FEATURE:
<223> OTHER INFORMATION: Amino acid sequence CASAR, variant 13

<400> SEQUENCE: 22

```
Met Val Ser Lys Ser Ser Ile Phe Ile Cys Leu Ser Leu Ile Ile Leu
1               5                   10                  15

Leu Ile Ile Ser Thr Gln Ile Val Leu Arg Glu Met Thr Ser Asp Ala
            20                  25                  30

Thr Ala Thr Leu Thr Gln Ala Met Asn Gly Asn Asn Ile Ser Glu Thr
        35                  40                  45

Lys His Val Gly Arg His Leu Val Lys Gly Ile Val Lys Ile Phe Lys
    50                  55                  60

Ala Gly Lys Val Ile Tyr Cys Lys Thr Cys Lys Thr Cys His Gly His
65                  70                  75                  80
```

```
Cys Asp Tyr Cys Cys Ala
                85


<210> SEQ ID NO 23
<211> LENGTH: 258
<212> TYPE: DNA
<213> ORGANISM: Artificial Sequence
<220> FEATURE:
<223> OTHER INFORMATION: Synthetic polynucleotide
<220> FEATURE:
<221> NAME/KEY: source
<222> LOCATION: (1)..(258)
<223> OTHER INFORMATION: /organism="Artificial Sequence"
      /note="Nucleotide sequence CASAR, variant 14"
      /mol_type="unassigned DNA"

<400> SEQUENCE: 23

atggtgagca agagctgcat cttcatctgc ctgagcctga tcatcctgct gatcatgagc      60

acccagatcg tggccagaga gctgtgcagc gaggccagcg ccagcctgtg ccaggccatg     120

aacggcaaca acatcagcga gaccaagaag gtgggcagac acctggtgaa gggcctgggc     180

aagatcttcc acgccggcaa ggtgatctac tgcaagacct gcaagagctg ccacggcaga     240

tgcgagtact gctgcgcc                                                   258


<210> SEQ ID NO 24
<211> LENGTH: 86
<212> TYPE: PRT
<213> ORGANISM: Artificial Sequence
<220> FEATURE:
<223> OTHER INFORMATION: Amino acid sequence CASAR, variant 14

<400> SEQUENCE: 24

Met Val Ser Lys Ser Cys Ile Phe Ile Cys Leu Ser Leu Ile Ile Leu
1               5                   10                  15

Leu Ile Met Ser Thr Gln Ile Val Ala Arg Glu Leu Cys Ser Glu Ala
            20                  25                  30

Ser Ala Ser Leu Cys Gln Ala Met Asn Gly Asn Asn Ile Ser Glu Thr
        35                  40                  45

Lys Lys Val Gly Arg His Leu Val Lys Gly Leu Gly Lys Ile Phe His
    50                  55                  60

Ala Gly Lys Val Ile Tyr Cys Lys Thr Cys Lys Ser Cys His Gly Arg
65                  70                  75                  80

Cys Glu Tyr Cys Cys Ala
                85


<210> SEQ ID NO 25
<211> LENGTH: 258
<212> TYPE: DNA
<213> ORGANISM: Artificial Sequence
<220> FEATURE:
<223> OTHER INFORMATION: Synthetic polynucleotide
<220> FEATURE:
<221> NAME/KEY: source
<222> LOCATION: (1)..(258)
<223> OTHER INFORMATION: /organism="Artificial Sequence"
      /note="Nucleotide sequence CASAR, variant 15"
      /mol_type="unassigned DNA"

<400> SEQUENCE: 25

atggtgagca agagcagcat cttcatctgc ctgagcatca tcatgctgct gatcatgagc      60

acccagatcg tggccagaga gatgaccagc gaggccagcg ccagcctgac ccaggccatg     120

aacggcaaca acatcagcga gaccaagaag gtggtgagac acctggtgaa gggcctgggc     180
```

```
aagatcttca aggccggcaa ggtgatctac tgcagaacca gcaagacctg ccacggcaga    240

tgcgactact gctgcgcc                                                  258


<210> SEQ ID NO 26
<211> LENGTH: 86
<212> TYPE: PRT
<213> ORGANISM: Artificial Sequence
<220> FEATURE:
<223> OTHER INFORMATION: Amino acid sequence CASAR, variant 15

<400> SEQUENCE: 26

Met Val Ser Lys Ser Ser Ile Phe Ile Cys Leu Ser Ile Ile Met Leu
1               5                   10                  15

Leu Ile Met Ser Thr Gln Ile Val Ala Arg Glu Met Thr Ser Glu Ala
            20                  25                  30

Ser Ala Ser Leu Thr Gln Ala Met Asn Gly Asn Asn Ile Ser Glu Thr
        35                  40                  45

Lys Lys Val Val Arg His Leu Val Lys Gly Leu Gly Lys Ile Phe Lys
    50                  55                  60

Ala Gly Lys Val Ile Tyr Cys Arg Thr Ser Lys Thr Cys His Gly Arg
65                  70                  75                  80

Cys Asp Tyr Cys Cys Ala
                85


<210> SEQ ID NO 27
<211> LENGTH: 258
<212> TYPE: DNA
<213> ORGANISM: Artificial Sequence
<220> FEATURE:
<223> OTHER INFORMATION: Synthetic polynucleotide
<220> FEATURE:
<221> NAME/KEY: source
<222> LOCATION: (1)..(258)
<223> OTHER INFORMATION: /organism="Artificial Sequence"
      /note="Nucleotide sequence CASAR, variant 16"
      /mol_type="unassigned DNA"

<400> SEQUENCE: 27

atggtgagca agagcagcat cttcatctgc ctgagcctga tcatcctgct gatcatgagc     60

acccagatcg tggccagaga gatgaccagc gaggccagcg ccagcctgac ccaggccatg    120

aacggcaaca acatcagcga gaccaagaag gtgggcagac acctggtgaa gggcctgggc    180

aagatcttcc acatgggcag agtgatctac tgcaagacct gcaagacctg ccacggcaga    240

tgcgactact gctgcgcc                                                  258


<210> SEQ ID NO 28
<211> LENGTH: 86
<212> TYPE: PRT
<213> ORGANISM: Artificial Sequence
<220> FEATURE:
<223> OTHER INFORMATION: Amino acid sequence CASAR, variant 16

<400> SEQUENCE: 28

Met Val Ser Lys Ser Ser Ile Phe Ile Cys Leu Ser Leu Ile Ile Leu
1               5                   10                  15

Leu Ile Met Ser Thr Gln Ile Val Ala Arg Glu Met Thr Ser Glu Ala
            20                  25                  30

Ser Ala Ser Leu Thr Gln Ala Met Asn Gly Asn Asn Ile Ser Glu Thr
        35                  40                  45

Lys Lys Val Gly Arg His Leu Val Lys Gly Leu Gly Lys Ile Phe His
```

-continued

```
    50                  55                  60

Met Gly Arg Val Ile Tyr Cys Lys Thr Cys Lys Thr Cys His Gly Arg
65                  70                  75                  80

Cys Asp Tyr Cys Cys Ala
                85
```

FUNGAL RESISTANT PLANTS EXPRESSING CASAR

This application is a National Stage application of International Application No. PCT/IB2013/059971, filed Nov. 7, 2013, which claims priority under 35 U.S.C. § 119 to European Patent Application No. 12192316.3 filed Nov. 13, 2012, the entire contents of which are incorporated herein by reference in their entirety.

REFERENCE TO SEQUENCE LISTING SUBMITTED VIA EFS-WEB

This application was filed electronically via EFS-Web and includes an electronically submitted sequence listing in .txt format. The .txt file contains a sequence listing entitled "74344-371_Seqlisting.txt" created on May 6, 2015, and is 22,328 bytes in size. The sequence listing in this .txt file is part of the specification and is hereby incorporated by reference herein in its entirety.

SUMMARY OF THE INVENTION

The present invention relates to a method of increasing resistance against fungal pathogens, in particular, pathogens of the order Pucciniales, for example soybean rust, in plants, plant parts, and/or plant cells. This is achieved by increasing the expression and/or activity of a CASAR protein in a plant, plant part and/or plant cell in comparison to wild type plants, wild type plant parts and/or wild type plant cells.

Furthermore, the invention relates to transgenic plants, plant parts, and/or plant cells having an increased resistance against fungal pathogens, in particular, pathogens of the order Pucciniales, for example soybean rust, and to recombinant expression vectors comprising a sequence that is identical or homologous to a sequence encoding a CASAR protein.

BACKGROUND OF THE INVENTION

The cultivation of agricultural crop plants serves mainly for the production of foodstuffs for humans and animals. Monocultures in particular, which are the rule nowadays, are highly susceptible to an epidemic-like spreading of diseases. The result is markedly reduced yields. To date, the pathogenic organisms have been controlled mainly by using pesticides. Nowadays, the possibility of directly modifying the genetic disposition of a plant or pathogen is also open to man.

Resistance generally describes the ability of a plant to prevent, or at least curtail the infestation and colonization by a harmful pathogen. Different mechanisms can be discerned in the naturally occurring resistance, with which the plants fend off colonization by phytopathogenic organisms. These specific interactions between the pathogen and the host determine the course of infection (Schopfer and Brennicke (1999) Pflanzenphysiologie, Springer Verlag, Berlin-Heidelberg, Germany).

With regard to the race specific resistance, also called host resistance, a differentiation is made between compatible and incompatible interactions. In the compatible interaction, an interaction occurs between a virulent pathogen and a susceptible plant. The pathogen survives, and may build up reproduction structures, while the host mostly dies off. An incompatible interaction occurs on the other hand when the pathogen infects the plant but is inhibited in its growth before or after weak development of symptoms (mostly by the presence of R genes of the nucleotide-binding site-leucine-rich repeat (NBS-LRR) family, see below). In the latter case, the plant is resistant to the respective pathogen (Schopfer and Brennicke, vide supra). However, this type of resistance is specific for a certain strain or pathogen.

In both compatible and incompatible interactions a defensive and specific reaction of the host to the pathogen occurs. In nature, however, this resistance is often overcome because of the rapid evolutionary development of new virulent races of the pathogens (Neu et al. (2003) American Cytopathol. Society, MPMI 16 No. 7: 626-633).

Most pathogens are plant-species specific. This means that a pathogen can induce a disease in a certain plant species, but not in other plant species (Heath (2002) Can. J. Plant Pathol. 24: 259-264). The resistance against a pathogen in certain plant species is called non-host resistance. The non-host resistance offers strong, broad, and permanent protection from phytopathogens. Genes providing non-host resistance provide the opportunity of a strong, broad and permanent protection against certain diseases in non-host plants. In particular, such a resistance works for different strains of the pathogen.

Fungi are distributed worldwide. Approximately 100 000 different fungal species are known to date. Thereof rusts are of great importance. They can have a complicated development cycle with up to five different spore stages (spermatium, aecidiospore, uredospore, teleutospore and basidiospore).

During the infection of plants by pathogenic fungi, different phases are usually observed. The first phases of the interaction between phytopathogenic fungi and their potential host plants are decisive for the colonization of the plant by the fungus. During the first stage of the infection, the spores become attached to the surface of the plants, germinate, and the fungus penetrates the plant. Fungi may penetrate the plant via existing ports such as stomata, lenticels, hydatodes and wounds, or else they penetrate the plant epidermis directly as the result of the mechanical force and with the aid of cell-wall-digesting enzymes. Specific infection structures are developed for penetration of the plant.

Immediately after recognition of a potential pathogen the plant starts to elicit defense reactions. Mostly the presence of the pathogen is sensed via so called PAMP receptors, a class of trans-membrane receptor like kinases recognizing conserved pathogen associated molecules (e.g. flagellin or chitin). Receptor-like kinases (RLKs) are signaling proteins that feature an extracellular domain connected via a transmembrane domain to a cytoplasmic kinase. This architecture indicates that RLKs perceive external signals, transducing them into the cell. In plants, RLKs were first implicated in the regulation of development, in pathogen responses, and in recognition events. (Santiago A Morillo and Frans E Tax (2006) Functional analysis of receptor-like kinases in monocots and dicots. Current Opinion in Plant Biology 9:460-469).

Downstream of the PAMP receptors, the phytohormones salicylic acid (SA), jasmonate (JA) and ethylene (ET) play a critical role in the regulation of the different defense reactions. Depending on the ratio of the different phytohormones, different defense reactions are elicited by the host cell. Generally SA dependent defense is linked with resistance against biotrophic pathogens, whereas JA/ET dependent defense reactions are active against necrotrophic pathogens (and insects).

In addition to the localized defense responses, plants that were attacked locally by a pathogen induce a "whole-plant" long lasting systemic defence response called systemic acquired resistance (SAR). SAR is associated with the induction of a wide range of genes (so called PR or "pathogenesis-related" genes), a burst of the reactive oxygen species (ROS), ethylene production and the accumulation of salicylic acid (SA).

Lee and Hwang (Planta 2005, Vol. 221: 790-800) showed that a gene called SAR8.2 (also known as CASAR for "*Capsicum annuum* SAR") accumulates in systemic pepper leaves as a result of a bacterial and fungal pathogen infection, abiotic elicitors, and by environmental stresses such as drought, salt, and low temperatures. The ectopic expression of CASAR in *Arabidopsis* leads to a constitutive expression of the PR-genes including AtPR-1, AtPR-4 and AtPR-5. Additionally the CASAR overexpression in *Arabidopsis* enhanced the resistance against infections by *Pseudomonas syringae* pv. *tomato, Fusarium oxysporum* f.sp. *matthiolae* or *Botrytis cinerea* (Lee and Hwang, Plant Molecular Biology (2006) 61:95-109). In addition Lee and Hwang (Plant Molecular Biology (2006) 61:95-109) showed that purified recombinant CASAR protein and crude protein extracts of the transgenic plants exhibited antifungal activity against some phytopathogenic fungi.

Lee and Hwang (Plant Molecular Biology (2006) 61:95-109) do not demonstrate enhanced resistance or antifungal activity against heminectrotrophic fungi, in particular against fungal pathogens of the order Pucciniales (rust). This specific group of fungal pathogens is characterized by a unique life-cycle.

For instance, the soybean rust *Phakopsora pachyrhizi* directly penetrates the plant epidermis. After crossing the epidermal cell, the fungus reaches the intercellular space of the mesophyll, where the fungus starts to spread through the leaves. To acquire nutrients the fungus penetrates mesophyll cells and develops haustoria inside the mesophyll cell. During the penetration process the plasmamembrane of the penetrated mesophyll cell stays intact. Therefore the soybean rust fungus establishes a biotrophic interaction with soybean.

The biotrophic phytopathogenic fungi, such as soybean rust and all other rust fungi, depend for their nutrition on the metabolism of living cells of the plants. This type of fungi belong to the group of biotrophic fungi, like other rust fungi, powdery mildew fungi or oomycete pathogens like the genus *Phytophthora* or *Peronospora* The necrotrophic phytopathogenic fungi depend for their nutrition on dead cells of the plants, e.g. species from the genus *Fusarium, Rhizoctonia* or *Mycospaerella*. Soybean rust has occupied an intermediate position, since it penetrates the epidermis directly, whereupon the penetrated cell becomes necrotic.

After the penetration, the fungus changes over to an obligatory-biotrophic lifestyle. The subgroup of the biotrophic fungal pathogens which follows essentially such an infection strategy is heminecrotrophic. In contrast to a heminecrotrophic pathogen, a hemibiotrophic pathogen lives for a short period of time in a biotrophic manner and subsequently starts killing the host cell and/or host organism, i.e., changes for the rest of its life-cycle to a necrotrophic life-style.

Soybean rust has become increasingly important in recent times. The disease may be caused by the biotrophic rusts *Phakopsora pachyrhizi* and *Phakopsora meibomiae*. They belong to the class Basidiomycota, order Pucciniales (rust), previously also known as Uredinales, family Phakopsoraceae. Both rusts infect a wide spectrum of leguminosic host plants. *P. pachyrhizi*, also referred to as Asian rust, is the more aggressive pathogen on soy (*Glycine max*), and is therefore, at least currently, of great importance for agriculture. *P. pachyrhizi* can be found in nearly all tropical and subtropical soy growing regions of the world. *P. pachyrhizi* is capable of infecting 31 species from 17 families of the Leguminosae under natural conditions and is capable of growing on further 60 species under controlled conditions (Sinclair et al. (eds.), Proceedings of the rust workshop (1995), National SoyaResearch Laboratory, Publication No. 1 (1996); Rytter J. L. et al., Plant Dis. 87, 818 (1984)). *P. meibomiae* has been found in the Caribbean Basin and in Puerto Rico, and has not caused substantial damage as yet.

*P. pachyrhizi* can currently be controlled in the field only by means of fungicides. Soy plants with resistance to the entire spectrum of the isolates are not available. When searching for resistant soybean accessions, six dominant R-genes of the NBS-LRR family, named Rpp1-5 and Rpp? (Hyuuga), which mediate resistance of soy to *P. pachyrhizi*, were discovered by screening thousands of soybean varieties. As the R-genes are derived from a host (soybean), the resistance was lost rapidly, as *P. pachyrhizi* develops new virulent races.

In recent years, fungal diseases, e.g. soybean rust, has gained in importance as pest in agricultural production. There was therefore a demand in the prior art for developing methods to control fungi and to provide fungal resistant plants.

Much research has been performed on the field of powdery and downy mildew infecting the epidermal layer of plants. However, the problem to cope with soybean rust which infects the mesophyll remains unsolved.

The object of the present invention is inter alia to provide a method of increasing resistance against fungal pathogens, preferably rust pathogens (i.e., fungal pathogens of the order Pucciniales), preferably against fungal pathogens of the family Phakopsoraceae, more preferably against fungal pathogens of the genus *Phakopsora*, most preferably against *Phakopsora pachyrhizi* and *Phakopsora meibomiae*, also known as soybean rust.

Surprisingly, we found that fungal pathogens, in particular of the order Pucciniales, in particular of the family Phakopsoraceae, for example soybean rust, can be controlled by increasing the expression of a CASAR gene.

The present invention therefore provides a method of increasing resistance against fungal pathogens, preferably against rust pathogens (i.e., fungal pathogens of the order Pucciniales), preferably fungal pathogens of the family Phakopsoraceae, more preferably against fungal pathogens of the genus *Phakopsora*, most preferably against *Phakopsora pachyrhizi* and *Phakopsora meibomiae*, also known as soybean rust, in transgenic plants, transgenic plant parts, or transgenic plant cells by overexpressing one or more CASAR nucleic acids.

A further object is to provide transgenic plants resistant against fungal pathogens, preferably rust pathogens (i.e., fungal pathogens of the order Pucciniales), preferably of the family Phakopsoraceae, more preferably against fungal pathogens of the genus *Phakopsora*, most preferably against *Phakopsora pachyrhizi* and *Phakopsora meibomiae*, also known as soybean rust, a method for producing such plants as well as a vector construct useful for the above methods.

Therefore, the present invention also refers to a recombinant vector construct and a transgenic plant, transgenic plant part, or transgenic plant cell comprising an exogenous CASAR nucleic acid. Furthermore, a method for the production of a transgenic plant, transgenic plant part or transgenic plant cell using the nucleic acid of the present invention is claimed herein. In addition, the use of a nucleic acid or the recombinant vector of the present invention for the transformation of a plant, plant part, or plant cell is claimed herein.

The objects of the present invention, as outlined above, are achieved by the subject-matter of the main claims. Preferred embodiments of the invention are defined by the subject matter of the dependent claims.

BRIEF SUMMARY OF THE INVENTION

The object of the present invention is inter alia to provide a method of increasing resistance against fungal pathogens, preferably rust pathogens (i.e., fungal pathogens of the order Pucciniales), preferably against fungal pathogens of the family Phakopsoraceae, more preferably against fungal pathogens of the genus *Phakopsora*, most preferably against *Phakopsora pachyrhizi* and *Phakopsora meibomiae*, also known as soybean rust.

Surprisingly, we found that resistance against fungal pathogens, in particular of the family Phakopsoraceae, for example soybean rust, can be enhanced by increasing the expression of a CASAR gene.

The present invention therefore provides a method of increasing resistance against fungal pathogens, preferably rust pathogens (i.e., fungal pathogens of the order Pucciniales), preferably against fungal pathogens of the family Phakopsoraceae, more preferably against fungal pathogens of the genus *Phakopsora*, most preferably against *Phakopsora pachyrhizi* and *Phakopsora meibomiae*, also known as soybean rust, in transgenic plants, transgenic plant parts, or transgenic plant cells by overexpressing one or more CASAR nucleic acids.

A further object is to provide transgenic plants resistant against fungal pathogens, preferably rust pathogens (i.e., fungal pathogens of the order Pucciniales), preferably of the family Phakopsoraceae, more preferably against fungal pathogens of the genus *Phakopsora*, most preferably against *Phakopsora pachyrhizi* and *Phakopsora meibomiae*, also known as soybean rust, a method for producing such plants as well as a vector construct useful for the above methods.

Therefore, the present invention also refers to a recombinant vector construct and a transgenic plant, transgenic plant part, or transgenic plant cell comprising an exogenous CASAR nucleic acid. Furthermore, a method for the production of a transgenic plant, transgenic plant part or transgenic plant cell using the nucleic acid of the present invention is claimed herein. In addition, the use of a nucleic acid or the recombinant vector of the present invention for the transformation of a plant, plant part, or plant cell is claimed herein.

The objects of the present invention, as outlined above, are achieved by the subject-matter of the main claims. Preferred embodiments of the invention are defined by the subject matter of the dependent claims.

BRIEF DESCRIPTION OF THE SEVERAL VIEWS OF THE DRAWINGS

FIG. 4 shows the full-length cDNA sequence of a CASAR gene from *Capsicum annuum* having SEQ ID NO: 1.

FIG. 5 shows the full-length cDNA sequence of a CASAR gene which has a codon optimization for optimal expression in soybean having SEQ ID NO: 2.

FIG. 6 shows the sequence of a CASAR protein (SEQ ID NO: 3).

FIG. 7 shows the sequence of the rust induced mesophyll specific promoter 820 having SEQ ID NO: 4.

FIG. 8 shows the result of the scoring of 43 transgenic soy plants (derived from 5 independent events) expressing the CASAR overexpression vector construct. $T_1$ soybean plants expressing CASAR protein were inoculated with spores of *Phakopsora pachyrhizi*. The evaluation of the diseased leaf area on all leaves was performed 14 days after inoculation. The average of the percentage of the leaf area showing fungal colonies or strong yellowing/browning on all leaves was considered as diseased leaf area. All 43 soybean $T_1$ plants expressing CASAR (expression checked by RT-PCR) were evaluated in parallel to non-transgenic control plants. The average of the diseased leaf area is shown in FIG. 7. Overexpression of CASAR significantly (***:$p<0.001$) reduces the diseased leaf area in comparison to non-transgenic control plants by 44.5%.

FIG. 9 contains a brief description of the sequences of the sequence listing.

DETAILED DESCRIPTION OF THE INVENTION

Figure 1:
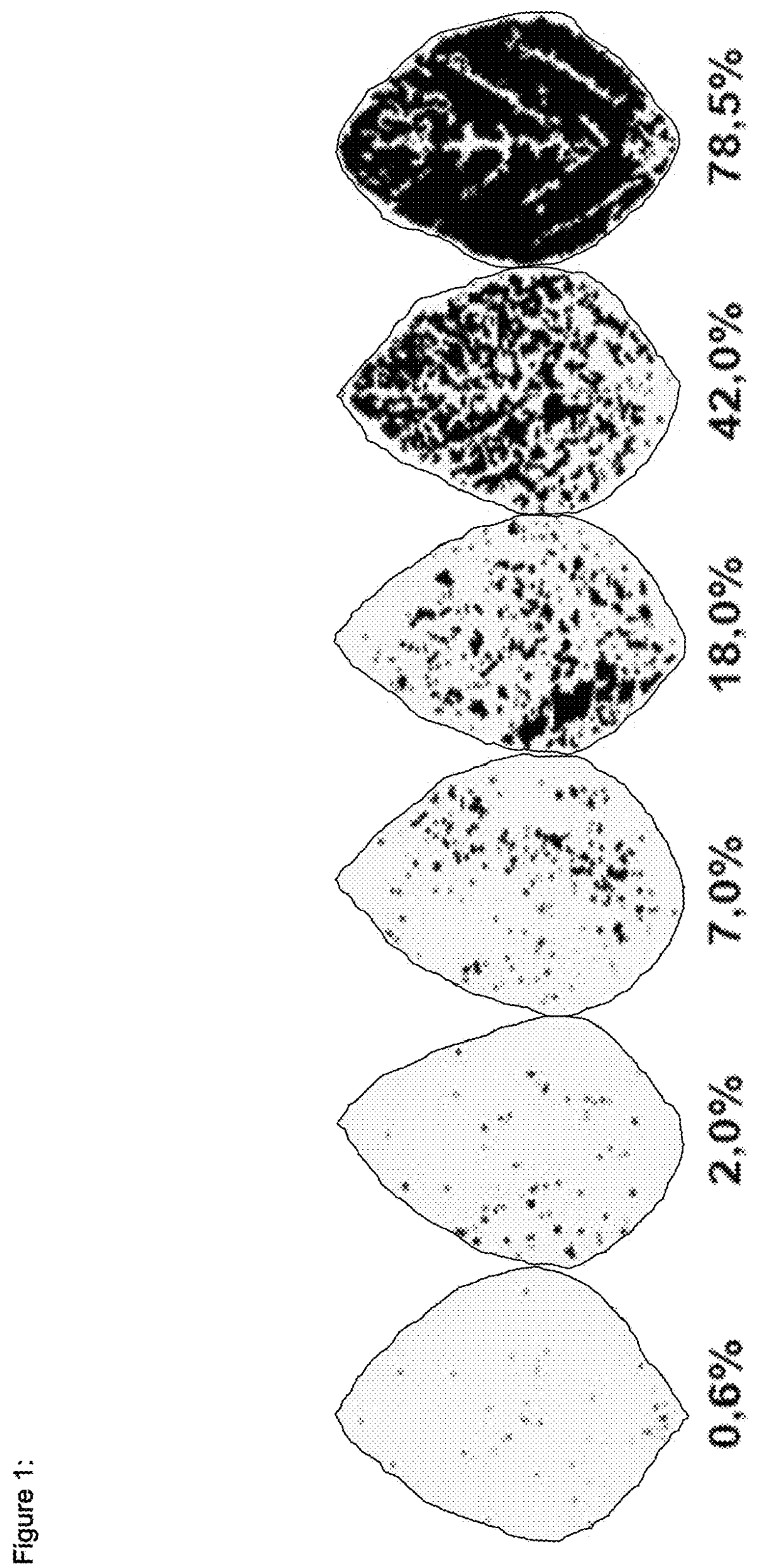
FIG. 1 shows the scoring system used to determine the level of diseased leaf area of wildtype and transgenic soy plants against the rust fungus *P. pachyrhizi* (as described in GODOY, C. V., KOGA, L. J. & CANTERI, M. G. Diagrammatic scale for assessment of soybean rust severity. Fitopatologia Brasileira 31:063-068. 2006).

The present invention may be understood more readily by reference to the following detailed description of the preferred embodiments of the invention and the examples included herein.

Definitions

Unless otherwise noted, the terms used herein are to be understood according to conventional usage by those of ordinary skill in the relevant art. In addition to the definitions of terms provided herein, definitions of common terms in molecular biology may also be found in Rieger et al., 1991 Glossary of genetics: classical and molecular, 5th Ed., Berlin: Springer-Verlag; and in Current Protocols in Molecular Biology, F. M. Ausubel et al., Eds., Current Protocols, a joint venture between Greene Publishing Associates, Inc. and John Wiley & Sons, Inc., (1998 Supplement).

It is to be understood that as used in the specification and in the claims, "a" or "an" can mean one or more, depending upon the context in which it is used. Thus, for example, reference to "a cell" can mean that at least one cell can be utilized. It is to be understood that the terminology used herein is for the purpose of describing specific embodiments only and is not intended to be limiting.

Throughout this application, various publications are referenced. The disclosures of all of these publications and those references cited within those publications in their entireties are hereby incorporated by reference into this application in order to more fully describe the state of the art to which this invention pertains. Standard techniques for cloning, DNA isolation, amplification and purification, for enzymatic reactions involving DNA ligase, DNA polymerase, restriction endonucleases and the like, and various separation techniques are those known and commonly employed by those skilled in the art. A number of standard techniques are described in Sambrook et al., 1989 Molecular Cloning, Second Edition, Cold Spring Harbor Laboratory, Plainview, N.Y.; Maniatis et al., 1982 Molecular Cloning, Cold Spring Harbor Laboratory, Plainview, N.Y.; Wu (Ed.) 1993 Meth. Enzymol. 218, Part I; Wu (Ed.) 1979 Meth Enzymol. 68; Wu et al., (Eds.) 1983 Meth. Enzymol. 100 and 101; Grossman and Moldave (Eds.) 1980 Meth. Enzymol. 65; Miller (Ed.) 1972 Experiments in Molecular Genetics, Cold Spring Harbor Laboratory, Cold Spring Harbor, N.Y.; Old and Primrose, 1981 Principles of Gene Manipulation, University of California Press, Berkeley; Schleif and Wensink, 1982 Practical Methods in Molecular Biology; Glover (Ed.) 1985 DNA Cloning Vol. I and II, IRL Press, Oxford, UK; Hames and Higgins (Eds.) 1985 Nucleic Acid Hybridization, IRL Press, Oxford, UK; and Setlow and Hollaender 1979 Genetic Engineering: Principles and Methods, Vols. 1-4, Plenum Press, New York. Abbreviations and nomenclature, where employed, are deemed standard in the field and commonly used in professional journals such as those cited herein.

"Homologues" of a protein encompass peptides, oligopeptides, polypeptides, proteins and/or enzymes having amino acid substitutions, deletions and/or insertions relative to the unmodified protein in question and having similar functional activity as the unmodified protein from which they are derived.

"Homologues" of a nucleic acid encompass nucleotides and/or polynucleotides having nucleic acid substitutions, deletions and/or insertions relative to the unmodified nucleic acid in question, wherein the protein coded by such nucleic acids has similar functional activity as the unmodified protein coded by the unmodified nucleic acid from which they are derived. In particular, homologues of a nucleic acid may encompass substitutions on the basis of the degenerative amino acid code.

The terms "identity", "homology" and "similarity" are used herein interchangeably. "Identity" or "homology" or "similarity" between two nucleic acids sequences or amino acid sequences refers in each case over the entire length of the respective CASAR nucleic acid sequence or CASAR amino acid sequence.

Preferably, "percentage of sequence identity" is calculated by comparing two optimally aligned sequences over a particular region, determining the number of positions at which the identical base or amino acid occurs in both sequences in order to yield the number of matched positions, dividing the number of such positions by the total number of positions in the region being compared and multiplying the result by 100.

Methods for the alignment of sequences for comparison are well known in the art, such methods include GAP, BESTFIT, BLAST, FASTA and TFASTA. GAP uses the algorithm of Needleman and Wunsch ((1970) J Mol Biol 48: 443-453) to find the global (i.e. spanning the complete sequences) alignment of two sequences that maximizes the number of matches and minimizes the number of gaps. The BLAST algorithm (Altschul et al. (1990) J Mol Biol 215: 403-10) calculates percent sequence identity or similarity or homology and performs a statistical analysis of the identity or similarity or homology between the two sequences. The software for performing BLAST analysis is publicly available through the National Centre for Biotechnology Information (NCBI). Homologues may readily be identified using, for example, the ClustalW multiple sequence alignment algorithm (version 1.83), with the default pairwise alignment parameters, and a scoring method in percentage. Global percentages of similarity/homology/identity may also be determined using one of the methods available in the MatGAT software package (Campanella et al., BMC Bioinformatics. 2003 Jul. 10; 4:29. MatGAT: an application that generates similarity/homology/identity matrices using protein or DNA sequences.). Minor manual editing may be performed to optimise alignment between conserved motifs, as would be apparent to a person skilled in the art. Furthermore, instead of using full-length sequences for the identification of homologues, specific domains may also be used. The sequence identity values may be determined over the entire nucleic acid or amino acid sequence or over selected domains or conserved motif(s), using the programs mentioned above using the default parameters. For local alignments, the Smith-Waterman algorithm is particularly useful (Smith T F, Waterman M S (1981) J. Mol. Biol 147(1); 195-7).

The sequence identity may also be calculated by means of the Vector NTI Suite 7.1 program of the company Informax (USA) employing the Clustal Method (Higgins D G, Sharp P M. Fast and sensitive multiple sequence alignments on a microcomputer. Comput Appl. Biosci. 1989 April; 5(2):151-1) with the following settings:

Multiple Alignment Parameter:

| | |
|---|---|
| Gap opening penalty | 10 |
| Gap extension penalty | 10 |
| Gap separation penalty range | 8 |
| Gap separation penalty | off |
| % identity for alignment delay | 40 |
| Residue specific gaps | off |
| Hydrophilic residue gap | off |
| Transition weighing | 0 |

Pairwise Alignment Parameter:

| | |
|---|---|
| FAST algorithm | on |
| K-tuple size | 1 |
| Gap penalty | 3 |
| Window size | 5 |
| Number of best diagonals | 5 |

Alternatively the identity may be determined according to Chenna, Ramu, Sugawara, Hideaki, Koike, Tadashi, Lopez, Rodrigo, Gibson, Toby J, Higgins, Desmond G, Thompson, Julie D. Multiple sequence alignment with the Clustal series of programs. (2003) Nucleic Acids Res 31 (13):3497-500, the web page: http://www.ebi.ac.uk/Tools/clustalw/index.html# and the following settings

| | |
|---|---|
| DNA Gap Open Penalty | 15.0 |
| DNA Gap Extension Penalty | 6.66 |
| DNA Matrix | Identity |
| Protein Gap Open Penalty | 10.0 |
| Protein Gap Extension Penalty | 0.2 |
| Protein matrix | Gonnet |
| Protein/DNA ENDGAP | −1 |
| Protein/DNA GAPDIST | 4 |

Sequence identity between the nucleic acid or protein useful according to the present invention and the CASAR nucleic acids or CASAR proteins may be optimized by sequence comparison and alignment algorithms known in the art (see Gribskov and Devereux, Sequence Analysis Primer, Stockton Press, 1991, and references cited therein)

and calculating the percent difference between the nucleotide or protein sequences by, for example, the Smith-Waterman algorithm as implemented in the BESTFIT software program using default parameters (e.g., University of Wisconsin Genetic Computing Group).

A "deletion" refers to removal of one or more amino acids from a protein or to the removal of one or more nucleic acids from DNA, ssRNA and/or dsRNA.

An "insertion" refers to one or more amino acid residues or nucleic acid residues being introduced into a predetermined site in a protein or the nucleic acid.

A "substitution" refers to replacement of amino acids of the protein with other amino acids having similar properties (such as similar hydrophobicity, hydrophilicity, antigenicity, propensity to form or break α-helical structures or beta-sheet structures).

On the nucleic acid level a substitution refers to a replacement of one or more nucleotides with other nucleotides within a nucleic acid, wherein the protein coded by the modified nucleic acid has a similar function. In particular homologues of a nucleic acid encompass substitutions on the basis of the degenerative amino acid code.

Amino acid substitutions are typically of single residues, but may be clustered depending upon functional constraints placed upon the protein and may range from 1 to 10 amino acids; insertions or deletion will usually be of the order of about 1 to 10 amino acid residues. The amino acid substitutions are preferably conservative amino acid substitutions. Conservative substitution tables are well known in the art (see for example Creighton (1984) Proteins. W.H. Freeman and Company (Eds) and Table 1 below or Taylor W. R. (1986) The classification of amino acid conservation J Theor Biol., 119:205-18).

TABLE 1

Examples of conserved amino acid substitutions

| Residue | Conservative Substitutions |
|---|---|
| Ala | Ser |
| Arg | Lys |
| Asn | Gln; His |
| Asp | Glu |
| Gln | Asn |
| Cys | Ser |
| Glu | Asp |
| Gly | Pro |
| His | Asn; Gln |
| Ile | Leu, Val |
| Leu | Ile; Val |
| Lys | Arg; Gln |
| Met | Leu; Ile |
| Phe | Met; Leu; Tyr |
| Ser | Thr; Gly |
| Thr | Ser; Val |
| Trp | Tyr |
| Tyr | Trp; Phe |
| Val | Ile; Leu |

Amino acid substitutions, deletions and/or insertions may readily be made using peptide synthetic techniques well known in the art, such as solid phase peptide synthesis and the like, or by recombinant DNA manipulation.

Methods for the manipulation of DNA sequences to produce substitution, insertion or deletion variants of a protein are well known in the art. For example, techniques for making substitution mutations at predetermined sites in DNA are well known to those skilled in the art and include M13 mutagenesis, T7-Gene in vitro mutagenesis (USB, Cleveland, Ohio), QuickChange Site Directed mutagenesis (Stratagene, San Diego, Calif.), PCR-mediated site-directed mutagenesis or other site-directed mutagenesis protocols.

Orthologues and paralogues encompass evolutionary concepts used to describe the ancestral relationships of genes. Paralogues are genes within the same species that have originated through duplication of an ancestral gene; orthologues are genes from different organisms that have originated through speciation, and are also derived from a common ancestral gene.

The terms "encode" or "coding for" is used for the capability of a nucleic acid to contain the information for the amino acid sequence of a protein via the genetic code, i.e., the succession of codons each being a sequence of three nucleotides, which specify which amino acid will be added next during protein synthesis. The terms "encode" or "coding for" therefore includes all possible reading frames of a nucleic acid. Furthermore, the terms "encode" or "coding for" also applies to a nucleic acid, which coding sequence is interrupted by noncoding nucleic acid sequences, which are removed prior translation, e.g., a nucleic acid sequence comprising introns.

The term "domain" refers to a set of amino acids conserved at specific positions along an alignment of sequences of evolutionarily related proteins. While amino acids at other positions can vary between homologues, amino acids that are highly conserved at specific positions indicate amino acids that are likely essential in the structure, stability or function of a protein.

Specialist databases exist for the identification of domains, for example, SMART (Schultz et al. (1998) Proc. Natl. Acad. Sci. USA 95, 5857-5864; Letunic et al. (2002) Nucleic Acids Res 30, 242-244), InterPro (Mulder et al., (2003) Nucl. Acids. Res. 31, 315-318), Prosite (Bucher and Bairoch (1994), A generalized profile syntax for biomolecular sequences motifs and its function in automatic sequence interpretation. (In) ISMB-94; Proceedings 2nd International Conference on Intelligent Systems for Molecular Biology. Altman R., Brutlag D., Karp P., Lathrop R., Searls D., Eds., pp 53-61, AAAI Press, Menlo Park; Hulo et al., Nucl. Acids. Res. 32:D134-D137, (2004)), or Pfam (Bateman et al., Nucleic Acids Research 30(1): 276-280 (2002)). A set of tools for in silico analysis of protein sequences is available on the ExPASy proteomics server (Swiss Institute of Bioinformatics (Gasteiger et al., ExPASy: the proteomics server for in-depth protein knowledge and analysis, Nucleic Acids Res. 31:3784-3788(2003)). Domains or motifs may also be identified using routine techniques, such as by sequence alignment.

As used herein the terms "fungal-resistance", "resistant to a fungus" and/or "fungal-resistant" mean reducing, preventing, or delaying an infection by fungi. The term "resistance" refers to fungal resistance. Resistance does not imply that the plant necessarily has 100% resistance to infection. In preferred embodiments, enhancing or increasing fungal resistance means that resistance in a resistant plant is greater than 10%, greater than 20%, greater than 30%, greater than 40%, greater than 50%, greater than 60%, greater than 70%, greater than 80%, greater than 90%, or greater than 95% in comparison to a wild type plant.

As used herein the terms "soybean rust-resistance", "resistant to a soybean rust", "soybean rust-resistant", "rust-resistance", "resistant to a rust", or "rust-resistant" mean reducing or preventing or delaying an infection of a plant, plant part, or plant cell by Phakopsoracea, in particular *Phakopsora pachyrhizi* and *Phakopsora meibomiae*—also known as soybean rust or Asian Soybean Rust (ASR), as compared to a wild type plant, wild type plant part, or wild type plant cell. Resistance does not imply that the plant necessarily has 100% resistance to infection. In preferred embodiments, enhancing or increasing rust resistance means that rust resistance in a resistant plant is greater than 10%, greater than 20%, greater than 30%, greater than 40%, greater than 50%, greater than 60%, greater than 70%, greater than 80%, greater than 90%, or greater than 95% in comparison to a wild type plant that is not resistant to soybean rust. Preferably the wild type plant is a plant of a similar, more preferably identical, genotype as the plant having increased resistance to the soybean rust, but does not comprise an exogenous CASAR nucleic acid, functional fragments thereof and/or an exogenous nucleic acid capable of hybridizing with a CASAR nucleic acid.

The level of fungal resistance of a plant can be determined in various ways, e.g. by scoring/measuring the infected leaf area in relation to the overall leaf area. Another possibility to determine the level of resistance is to count the number of soybean rust colonies on the plant or to measure the amount of spores produced by these colonies. Another way to resolve the degree of fungal infestation is to specifically measure the amount of rust DNA by quantitative (q) PCR. Specific probes and primer sequences for most fungal pathogens are available in the literature (Frederick R D, Snyder C L, Peterson G L, et al. 2002 Polymerase chain reaction assays for the detection and discrimination of the rust pathogens *Phakopsora pachyrhizi* and *P. meibomiae*, Phytopathology 92(2) 217-227).

The term "hybridization" as used herein includes "any process by which a strand of nucleic acid molecule joins with a complementary strand through base pairing" (J. Coombs (1994) Dictionary of Biotechnology, Stockton Press, New York). Hybridization and the strength of hybridization (i.e., the strength of the association between the nucleic acid molecules) is impacted by such factors as the degree of complementarity between the nucleic acid molecules, stringency of the conditions involved, the Tm of the formed hybrid, and the G:C ratio within the nucleic acid molecules.

As used herein, the term "Tm" is used in reference to the "melting temperature." The melting temperature is the temperature at which a population of double-stranded nucleic acid molecules becomes half dissociated into single strands. The equation for calculating the Tm of nucleic acid molecules is well known in the art. As indicated by standard references, a simple estimate of the Tm value may be calculated by the equation: Tm=81.5+0.41 (% G+C), when a nucleic acid molecule is in aqueous solution at 1 M NaCl (see e.g., Anderson and Young, Quantitative Filter Hybridization, in Nucleic Acid Hybridization (1985). Other references include more sophisticated computations, which take structural as well as sequence characteristics into account for the calculation of Tm. Stringent conditions, are known to those skilled in the art and can be found in Current Protocols in Molecular Biology, John Wiley & Sons, N.Y. (1989), 6.3.1-6.3.6.

In particular, the term "stringency conditions" refers to conditions, wherein 100 contiguous nucleotides or more, 150 contiguous nucleotides or more, 200 contiguous nucleotides or more or 250 contiguous nucleotides or more which are a fragment or identical to the complementary nucleic acid molecule (DNA, RNA, ssDNA or ssRNA) hybridizes under conditions equivalent to hybridization in 7% sodium dodecyl sulfate (SDS), 0.5 M NaPO4, 1 mM EDTA at 50° C. with washing in 2×SSC, 0.1% SDS at 50° C. or 65° C., preferably at 65° C., with a specific nucleic acid molecule (DNA; RNA, ssDNA or ss RNA). Preferably, the hybridizing conditions are equivalent to hybridization in 7% sodium dodecyl sulfate (SDS), 0.5 M NaPO4, 1 mM EDTA at 50° C. with washing in 1×SSC, 0.1% SDS at 50° C. or 65° C., preferably 65° C., more preferably the hybridizing conditions are equivalent to hybridization in 7% sodium dodecyl sulfate (SDS), 0.5 M NaPO4, 1 mM EDTA at 50° C. with washing in 0.1×SSC, 0.1% SDS at 50° C. or 65° C., preferably 65° C. Preferably, the complementary nucleotides hybridize with a fragment or the whole CASAR nucleic acids. Alternatively, preferred hybridization conditions encompass hybridisation at 65° C. in 1×SSC or at 42° C. in 1×SSC and 50% formamide, followed by washing at 65° C. in 0.3×SSC or hybridisation at 50° C. in 4×SSC or at 40° C. in 6×SSC and 50% formamide, followed by washing at 50° C. in 2×SSC. Further preferred hybridization conditions are 0.1% SDS, 0.1 SSD and 65° C.

The term "plant" is intended to encompass plants at any stage of maturity or development, as well as any tissues or organs (plant parts) taken or derived from any such plant unless otherwise clearly indicated by context. Plant parts include, but are not limited to, plant cells, stems, roots, flowers, ovules, stamens, seeds, leaves, embryos, meristematic regions, callus tissue, anther cultures, gametophytes, sporophytes, pollen, microspores, protoplasts, hairy root cultures, and/or the like. The present invention also includes seeds produced by the plants of the present invention. Preferably, the seeds comprise the exogenous CASAR nucleic acids. In one embodiment, the seeds can develop into plants with increased resistance to fungal infection as compared to a wild-type variety of the plant seed. As used herein, a "plant cell" includes, but is not limited to, a protoplast, gamete producing cell, and a cell that regenerates into a whole plant. Tissue culture of various tissues of plants and regeneration of plants therefrom is well known in the art and is widely published.

Reference herein to an "endogenous" nucleic acid and/or protein refers to the nucleic acid and/or protein in question as found in a plant in its natural form (i.e., without there being any human intervention).

The term "exogenous" nucleic acid refers to a nucleic acid that has been introduced in a plant by means of gene technology. An "exogenous" nucleic acid can either not occur in a plant in its natural form, be different from the nucleic acid in question as found in a plant in its natural form, or can be identical to a nucleic acid found in a plant in its natural form, but integrated not within its natural genetic environment. The corresponding meaning of "exogenous" is applied in the context of protein expression. For example, a transgenic plant containing a transgene, i.e., an exogenous nucleic acid, may, when compared to the expression of the endogenous gene, encounter a substantial increase of the expression of the respective gene or protein in total. A transgenic plant according to the present invention includes an exogenous CASAR nucleic acid integrated at any genetic loci and optionally the plant may also include the endogenous gene within the natural genetic background.

For the purposes of the invention, "recombinant" means with regard to, for example, a nucleic acid sequence, a nucleic acid molecule, an expression cassette or a vector construct comprising any one or more CASAR nucleic acids, all those constructions brought about by man by gene technological methods in which either (a) the sequences of the one or more CASAR nucleic acid or a part thereof, or (b) genetic control sequence(s) which is operably linked with the CASAR nucleic acid sequence according to the invention, for example a promoter, or (c) a) and b)

are not located in their natural genetic environment or have been modified by man by gene technological methods. The modification may take the form of, for example, a substitution, addition, deletion, inversion or insertion of one or more nucleotide residues. The natural genetic environment is understood as meaning the natural genomic or chromosomal locus in the original plant or the presence in a genomic library or the combination with the natural promoter.

For instance, a naturally occurring expression cassette—for example the naturally occurring combination of the natural promoter of the nucleic acid sequences with the corresponding nucleic acid sequence encoding a protein useful in the methods of the present invention, as defined above—becomes a recombinant expression cassette when this expression cassette is modified by man by non-natural, synthetic ("artificial") methods such as, for example, mutagenic treatment. Suitable methods are described, for example, in U.S. Pat. No. 5,565,350, WO 00/15815 or US200405323. Furthermore, a naturally occurring expression cassette—for example the naturally occurring combination of the natural promoter of the nucleic acid sequences with the corresponding nucleic acid sequence encoding a protein useful in the methods of the present invention, as defined above—becomes a recombinant expression cassette when this expression cassette is not integrated in the natural genetic environment but in a different genetic environment.

The term "isolated nucleic acid" or "isolated protein" refers to a nucleic acid or protein that is not located in its natural environment, in particular its natural cellular environment. Thus, an isolated nucleic acid or isolated protein is essentially separated from other components of its natural environment. However, the skilled person in the art is aware that preparations of an isolated nucleic acid or an isolated protein can display a certain degree of impurity depending on the isolation procedure used. Methods for purifying nucleic acids and proteins are well known in the art. The isolated gene may be isolated from an organism or may be manmade, for example by chemical synthesis. In this regard, a recombinant nucleic acid may also be in an isolated form.

As used herein, the term "transgenic" refers to an organism, e.g., a plant, plant cell, callus, plant tissue, or plant part that exogenously contains the nucleic acid, recombinant construct, vector or expression cassette described herein or a part thereof which is preferably introduced by non-essentially biological processes, preferably by Agrobacteria transformation. The recombinant construct or a part thereof is stably integrated into a chromosome, so that it is passed on to successive generations by clonal propagation, vegetative propagation or sexual propagation. Preferred successive generations are transgenic too. Essentially biological processes may be crossing of plants and/or natural recombination.

A transgenic plant, plants cell or tissue for the purposes of the invention is thus understood as meaning that an exogenous CASAR nucleic acid, recombinant construct, vector or expression cassette including one or more CASAR nucleic acids is integrated into the genome by means of gene technology.

A "wild type" plant, "wild type" plant part, or "wild type" plant cell means that said plant, plant part, or plant cell does not express exogenous CASAR nucleic acid or exogenous CASAR protein.

Natural locus means the location on a specific chromosome, preferably the location between certain genes, more preferably the same sequence background as in the original plant which is transformed.

Preferably, the transgenic plant, plant cell or tissue thereof expresses the CASAR nucleic acids, CASAR constructs or CASAR expression cassettes described herein.

The term "expression" or "gene expression" means the transcription of a specific gene or specific genes or specific genetic vector construct. The term "expression" or "gene expression" in particular means the transcription of a gene or genes or genetic vector construct into structural RNA (rRNA, tRNA), or mRNA with or without subsequent translation of the latter into a protein. The process includes transcription of DNA and processing of the resulting RNA product. The term "expression" or "gene expression" can also include the translation of the mRNA and therewith the synthesis of the encoded protein, i.e., protein expression.

The term "increased expression" or "enhanced expression" or "overexpression" or "increase of content" as used herein means any form of expression that is additional to the original wild-type expression level. For the purposes of this invention, the original wild-type expression level might also be zero (absence of expression).

Methods for increasing expression of genes or gene products are well documented in the art and include, for example, overexpression driven by appropriate promoters, the use of transcription enhancers or translation enhancers. Isolated nucleic acids which serve as promoter or enhancer elements may be introduced in an appropriate position (typically upstream) of a non-heterologous form of a polynucleotide so as to upregulate expression of a nucleic acid encoding the protein of interest. For example, endogenous promoters may be altered in vivo by mutation, deletion, and/or substitution (see, Kmiec, U.S. Pat. No. 5,565,350; Zarling et al., WO9322443), or isolated promoters may be introduced into a plant cell in the proper orientation and distance from a gene of the present invention so as to control the expression of the gene.

The term "functional fragment" refers to any nucleic acid or protein which comprises merely a part of the fulllength nucleic acid or fulllength protein, respectively, but still provides the same function, e.g., fungal resistance, when expressed or repressed in a plant, respectively. Preferably, the fragment comprises at least 50%, at least 60%, at least 70%, at least 80%, at least 90% at least 95%, at least 98%, at least 99% of the original sequence. Preferably, the functional fragment comprises contiguous nucleic acids or amino acids as in the original nucleic acid or original protein, respectively. In one embodiment the fragment of any of the CASAR nucleic acids has an identity as defined above over a length of at least 20%, at least 30%, at least 50%, at least 75%, at least 90% of the nucleotides of the respective CASAR nucleic acid.

The term "splice variant" as used herein encompasses variants of a nucleic acid sequence in which selected introns and/or exons have been excised, replaced, displaced or added, or in which introns have been shortened or lengthened. Thus, a splice variant can have one or more or even all introns removed or added. According to this definition, a cDNA is considered as a splice variant of the respective intron-containing genomic sequence and vice versa. Such splice variants may be found in nature or may be manmade. Methods for predicting and isolating such splice variants are well known in the art (see for example Foissac and Schiex (2005) BMC Bioinformatics 6: 25).

In cases where overexpression of nucleic acid is desired, the term "similar functional activity" or "similar function" means that any homologue and/or fragment provide fungal resistance when expressed in a plant. Preferably similar functional activity means at least 50%, at least 60%, at least 70%, at least 80%, at least 90%, at least 95%, at least 98%, at least 99% or 100% or higher fungal resistance compared with functional activity provided by the exogenous expression of the CASAR nucleotide sequence as defined by SEQ ID NO: 1 or 2 or the CASAR protein sequence as defined by SEQ ID NO: 3.

The term "increased activity" or "enhanced activity" as used herein means any protein having increased activity and which provides an increased fungal resistance compared with the wildtype plant merely expressing the respective endogenous CASAR nucleic acid. As far as overexpression is concerned, for the purposes of this invention, the original wild-type expression level might also be zero (absence of expression).

With respect to a vector construct and/or the recombinant nucleic acid molecules, the term "operatively linked" is intended to mean that the nucleic acid to be expressed is linked to the regulatory sequence, including promoters, terminators, enhancers and/or other expression control elements (e.g., polyadenylation signals), in a manner which allows for expression of the nucleic acid (e.g., in a host plant cell when the vector is introduced into the host plant cell). Such regulatory sequences are described, for example, in Goeddel, Gene Expression Technology: Methods in Enzymology 185, Academic Press, San Diego, Calif. (1990) and Gruber and Crosby, in: Methods in Plant Molecular Biology and Biotechnology, Eds. Glick and Thompson, Chapter 7, 89-108, CRC Press: Boca Raton, Fla., including the references therein. Regulatory sequences include those that direct constitutive expression of a nucleotide sequence in many types of host cells and those that direct expression of the nucleotide sequence only in certain host cells or under certain conditions. It will be appreciated by those skilled in the art that the design of the vector can depend on such factors as the choice of the host cell to be transformed, the level of expression of nucleic acid desired, and the like.

The term "introduction" or "transformation" as referred to herein encompass the transfer of an exogenous polynucleotide into a host cell, irrespective of the method used for transfer. Plant tissue capable of subsequent clonal propagation, whether by organogenesis or embryogenesis, may be transformed with a vector construct of the present invention and a whole plant regenerated there from. The particular tissue chosen will vary depending on the clonal propagation systems available for, and best suited to, the particular species being transformed. Exemplary tissue targets include leaf disks, pollen, embryos, cotyledons, hypocotyls, megagametophytes, callus tissue, existing meristematic tissue (e.g., apical meristem, axillary buds, and root meristems), and induced meristem tissue (e.g., cotyledon meristem and hypocotyl meristem). The polynucleotide may be transiently or stably introduced into a host cell and may be maintained non-integrated, for example, as a plasmid. Alternatively, it may be integrated into the host genome. The host genome includes the nucleic acid contained in the nucleus as well as the nucleic acid contained in the plastids, e.g., chloroplasts, and/or mitochondria. The resulting transformed plant cell may then be used to regenerate a transformed plant in a manner known to persons skilled in the art.

The term "terminator" encompasses a control sequence which is a DNA sequence at the end of a transcriptional unit which signals 3' processing and polyadenylation of a primary transcript and termination of transcription. The terminator can be derived from the natural gene, from a variety of other plant genes, or from T-DNA. The terminator to be added may be derived from, for example, the nopaline synthase or octopine synthase genes, or alternatively from another plant gene, or less preferably from any other eukaryotic gene.

DETAILED DESCRIPTION

CASAR Nucleic Acids

The CASAR nucleic acid to be overexpressed in order to achieve increased resistance to fungal pathogens, e.g., of the family Phakopsoraceae, for example soybean rust, is preferably a nucleic acid coding for a CASAR protein, and is preferably as defined by SEQ ID NO: 2, 1, 5-12, 13, 15, 17, 19, 21, 23, 25, or 27, or a fragment, homolog, derivative, orthologue or paralogue thereof, or a splice variant thereof. Preferably, the nucleic acid coding for a CASAR protein of the present invention has at least 60% identity, preferably at least 70% sequence identity, at least 80%, at least 90%, at least 95%, at least 98%, at least 99% sequence identity, or even 100% sequence identity with SEQ ID NO: 2, 1, 5-12, 13, 15, 17, 19, 21, 23, 25, or 27, or is a functional fragment thereof, or a splice variant thereof. Most preferred is at least 90% identity, at least 95% identity, more preferred is at least 98% or at least 99% identity with SEQ ID NO: 2, 1, 5-12, 13, 15, 17, 19, 21, 23, 25, or 27.

Preferably, the CASAR nucleic acid to be overexpressed in order to achieve increased resistance to fungal pathogens, e.g., of the family Phakopsoraceae, for example soybean rust, is preferably a nucleic acid coding for a CASAR protein, and is preferably as defined by SEQ ID NO: 1, or a fragment, homolog, derivative, orthologue or paralogue thereof, or a splice variant thereof. Preferably, the nucleic acid coding for a CASAR protein of the present invention has at least 60% identity, preferably at least 70% sequence identity, at least 80%, at least 90%, at least 95%, at least 98%, at least 99% sequence identity, or even 100% sequence identity with SEQ ID NO: 1 or is a functional fragment thereof, or a splice variant thereof. Most preferred is at least 90% identity, at least 95% identity, more preferred is at least 98% or at least 99% identity with SEQ ID NO: 1.

More preferably, the CASAR nucleic acid to be overexpressed in order to achieve increased resistance to fungal pathogens, e.g., of the family Phakopsoraceae, for example soybean rust, is preferably a nucleic acid coding for a CASAR protein, and is preferably as defined by SEQ ID NO: 2, or a fragment, homolog, derivative, orthologue or paralogue thereof, or a splice variant thereof. Preferably, the nucleic acid coding for a CASAR protein of the present invention has at least 60% identity, preferably at least 70% sequence identity, at least 80%, at least 90%, at least 95%, at least 98%, at least 99% sequence identity, or even 100% sequence identity with SEQ ID NO: 2 or is a functional fragment thereof, or a splice variant thereof. Most preferred is at least 95% identity, more preferred is at least 98% or at least 99% identity with SEQ ID NO: 2.

Preferably the CASAR nucleic acid is an isolated nucleic acid molecule consisting of or comprising a nucleic acid selected from the group consisting of:

(i) a nucleic acid having in increasing order of preference at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to the nucleic acid sequence represented by SEQ ID NO: 2, 1, 5-12, 13, 15, 17, 19, 21, 23, 25, or 27, or a functional fragment, derivative, orthologue, or paralogue thereof, or a splice variant thereof;

(ii) a nucleic acid encoding a CASAR protein having in increasing order of preference at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to the amino acid sequence represented by SEQ ID NO: 3, 14, 16, 18, 20, 22, 24, 26, or 28, or a functional fragment, derivative, orthologue, or paralogue thereof; preferably the CASAR protein has essentially the same biological activity as a CASAR protein encoded by SEQ ID NO: 2 or 1; preferably the CASAR protein confers enhanced fungal resistance relative to control plants;

(iii) a nucleic acid molecule which hybridizes with a complementary sequence of any of the nucleic acid molecules of (i) or (ii) under high stringency hybridization conditions; preferably encoding a CASAR protein; preferably wherein the nucleic acid molecule codes for a polypeptide which has essentially identical properties to the polypeptide described in SEQ ID NO: 3; preferably the encoded protein confers enhanced fungal resistance relative to control plants; and (iv) a nucleic acid encoding the same CASAR protein as the CASAR nucleic acids of (i) to (iii) above, but differing from the CASAR nucleic acids of (i) to (iii) above due to the degeneracy of the genetic code.

Preferably, the nucleic acid coding for a CASAR protein of the present invention has at least 60% identity, preferably at least 70% sequence identity, at least 80%, at least 90%, at least 95%, at least 98%, at least 99% sequence identity, or even 100% sequence identity with SEQ ID NO: 3, 14, 16, 18, 20, 22, 24, 26, or 28. Most preferred is at least 95% identity, more preferred is at least 98% or at least 99% identity with SEQ ID NO: 3, 14, 16, 18, 20, 22, 24, 26, or 28.

Preferably, the nucleic acid coding for a CASAR protein of the present invention has at least 60% identity, preferably at least 70% sequence identity, at least 80%, at least 90%, at least 95%, at least 98%, at least 99% sequence identity, or even 100% sequence identity with SEQ ID NO: 3. Most preferred is at least 95% identity, more preferred is at least 98% or at least 99% identity with SEQ ID NO: 3.

Preferably the CASAR nucleic acid is an isolated nucleic acid molecule consisting of or comprising a nucleic acid selected from the group consisting of:

(i) a nucleic acid having in increasing order of preference at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to the nucleic acid sequence represented by SEQ ID NO: 2, or a functional fragment, derivative, orthologue, or paralogue thereof, or a splice variant thereof;

(ii) a nucleic acid encoding a CASAR protein having in increasing order of preference at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to the amino acid sequence represented by SEQ ID NO: 3, or a functional fragment, derivative, orthologue, or paralogue thereof; preferably the CASAR protein has essentially the same biological activity as a CASAR protein encoded by SEQ ID NO: 2, preferably the CASAR protein confers enhanced fungal resistance relative to control plants;

(iii) a nucleic acid molecule which hybridizes with a complementary sequence of any of the nucleic acid molecules of (i) or (ii) under high stringency hybridization conditions; preferably encoding a CASAR protein; preferably wherein the nucleic acid molecule codes for a polypeptide which has essentially identical properties to the polypeptide described in SEQ ID NO: 3; preferably the encoded protein confers enhanced fungal resistance relative to control plants; and (iv) a nucleic acid encoding the same CASAR protein as the CASAR nucleic acids of (i) to (iii) above, but differing from the CASAR nucleic acids of (i) to (iii) above due to the degeneracy of the genetic code.

Percentages of identity of a nucleic acid are indicated with reference to the entire nucleotide region given in a sequence specifically disclosed herein.

Preferably the portion of the CASAR nucleic acid is about 150-160, about 160-170, about 170-180, about 180-190, about 190-200, about 200-210, about 210-220, about 220-230, about 230-240, about 240-250, or about 250-261 nucleotides, preferably consecutive nucleotides, preferably counted from the 5' or 3' end of the nucleic acid, in length, of the nucleic acid sequences given in SEQ ID NO: 2, 1, 5-12, 13, 15, 17, 19, 21, 23, 25, or 27.

Preferably, the CASAR nucleic acid comprises at least about 50, at least about 75, at least about 100, at least about 125, at least about 150, at least about 160, at least about 170, at least about 180, at least about 190, at least about 200, at least about 210, at least about 220, at least about 230, at least about 240, or at least about 250 nucleotides, preferably continuous nucleotides, preferably counted from the 5' or 3' end of the nucleic acid or up to the full length of the nucleic acid sequence set out in SEQ ID NO: 2, 1, 5-12, 13, 15, 17, 19, 21, 23, 25, or 27.

Preferably the portion of the CASAR nucleic acid is about 150-160, about 160-170, about 170-180, about 180-190, about 190-200, about 200-210, about 210-220, about 220-230, about 230-240, about 240-250, or about 250-261 nucleotides, preferably consecutive nucleotides, preferably counted from the 5' or 3' end of the nucleic acid, in length, of the nucleic acid sequences given in SEQ ID NO: 2 or 1.

Preferably, the CASAR nucleic acid comprises at least about 50, at least about 75, at least about 100, at least about 125, at least about 150, at least about 160, at least about 170, at least about 180, at least about 190, at least about 200, at least about 210, at least about 220, at least about 230, at least about 240, or at least about 250 nucleotides, preferably continuous nucleotides, preferably counted from the 5' or 3' end of the nucleic acid or up to the full length of the nucleic acid sequence set out in SEQ ID NO: 2 or 1.

All the nucleic acid sequences mentioned herein (single-stranded and double-stranded DNA and RNA sequences, for example cDNA and mRNA) can be produced in a known way by chemical synthesis from the nucleotide building blocks, e.g. by fragment condensation of individual overlapping, complementary nucleic acid building blocks of the double helix. Chemical synthesis of oligonucleotides can, for example, be performed in a known way, by the phosphoamidite method (Voet, Voet, 2nd edition, Wiley Press, New York, pages 896-897). The accumulation of synthetic oligonucleotides and filling of gaps by means of the Klenow fragment of DNA polymerase and ligation reactions as well as general cloning techniques are described in Sambrook et al. (1989), see below.

The CASAR nucleic acids described herein are useful in the constructs, methods, plants, harvestable parts and products of the invention.

CASAR Proteins

The CASAR protein is preferably defined by SEQ ID NO: 3, 14, 16, 18, 20, 22, 24, 26, or 28, or a fragment, homolog, derivative, orthologue or paralogue thereof. Preferably, the CASAR protein of the present invention is encoded by a nucleic acid, which has at least 60% identity, preferably at least 70% sequence identity, at least 80%, at least 90%, at least 95%, at least 98%, at least 99% sequence identity, or even 100% sequence identity with SEQ ID NO: 3, 14, 16, 18, 20, 22, 24, 26, or 28 or a functional fragment thereof. More preferably, the CASAR protein of the present invention has at least 60%, preferably at least 70% sequence identity, at least 80%, at least 90%, at least 95%, at least 98%, at least 99% sequence identity, or even 100% sequence identity with SEQ ID NO: 3, 14, 16, 18, 20, 22, 24, 26, or 28, or is a functional fragment thereof, an orthologue or a paralogue thereof. Most preferred is at least 90% identity, least 95% identity, more preferred is at least 98% or at least 99% identity with SEQ ID NO: 3, 14, 16, 18, 20, 22, 24, 26, or 28.

The CASAR protein is preferably defined by SEQ ID NO: 3, or a fragment, homolog, derivative, orthologue or paralogue thereof. Preferably, the CASAR protein of the present invention is encoded by a nucleic acid, which has at least 60% identity, preferably at least 70% sequence identity, at least 80%, at least 90%, at least 95%, at least 98%, at least 99% sequence identity, or even 100% sequence identity with SEQ ID NO: 3, or a functional fragment thereof. More preferably, the CASAR protein of the present invention has at least 60%, preferably at least 70% sequence identity, at least 80%, at least 90%, at least 95%, at least 98%, at least 99% sequence identity, or even 100% sequence identity with SEQ ID NO: 3, or is a functional fragment thereof, an orthologue or a paralogue thereof. Most preferred is at least 90% identity, least 95% identity, more preferred is at least 98% or at least 99% identity with SEQ ID NO: 3.

Preferably, the CASAR protein is a protein consisting of or comprising an amino acid sequence selected from the group consisting of:

(i) an amino acid sequence having in increasing order of preference at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to the amino acid sequence represented by SEQ ID NO: 3, 14, 16, 18, 20, 22, 24, 26, or 28, or a functional fragment, derivative, orthologue, or paralogue thereof; preferably the CASAR protein has essentially the same biological activity as a CASAR protein encoded by SEQ ID NO: 2 or 1; preferably the CASAR protein confers enhanced fungal resistance relative to control plants; or (ii) an amino acid sequence encoded by a nucleic acid having in increasing order of preference at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to the nucleic acid sequence represented by SEQ ID NO: 2, 1, 5-12, 13, 15, 17, 19, 21, 23, 25, or 27, or a functional fragment, derivative, orthologue, or paralogue thereof, or a splice variant thereof; preferably the CASAR protein confers enhanced fungal resistance relative to control plants.

Preferably, the CASAR protein is a protein comprising an amino acid sequence selected from the group consisting of:

(i) an amino acid sequence having in increasing order of preference at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to the amino acid sequence represented by SEQ ID NO: 3, or a functional fragment, derivative, orthologue, or paralogue thereof; preferably the CASAR protein has essentially the same biological activity as a CASAR protein encoded by SEQ ID NO: 2 or 1; preferably the CASAR protein confers enhanced fungal resistance relative to control plants; or (ii) an amino acid sequence encoded by a nucleic acid having in increasing order of preference at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to the nucleic acid sequence represented by SEQ ID NO: 2 or 1, or a functional fragment, derivative, orthologue, or paralogue thereof, or a splice variant thereof; preferably the CASAR protein confers enhanced fungal resistance relative to control plants.

A preferred derivative of a CASAR protein is a CASAR protein consisting of or comprising an amino acid sequence selected from the group consisting of:

an amino acid sequence having in increasing order of preference at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, and at least 99% sequence identity to the amino acid sequence represented by SEQ ID NO: 3, 14, 16, 18, 20, 22, 24, 26, or 28, wherein the non-identical amino acid residues are conservative amino acid substitutions, preferably as shown in Table 1, of the corresponding amino acid residue of SEQ ID NO: 3, 14, 16, 18, 20, 22, 24, 26, or 28; preferably the CASAR protein has essentially the same biological activity as SEQ ID NO: 3, 14, 16, 18, 20, 22, 24, 26, or 28 or as a CASAR protein encoded by SEQ ID NO: 2 or 1; preferably the CASAR protein confers enhanced fungal resistance relative to control plants.

Preferably, the CASAR protein consists of or comprises an amino acid sequence represented by SEQ ID NO: 3, 14, 16, 18, 20, 22, 24, 26, or 28 with one or more conservative amino acid substitutions, preferably as shown in Table 1, of the corresponding amino acid residues of SEQ ID NO: 3, 14, 16, 18, 20, 22, 24, 26, or 28. Preferably 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 1-10, 10-20, 20-30, 40-50, 50-60, 60-70, 70-80, 80-90, 90-100, 100-110, 110-120, or 120-130 amino acid residues of SEQ ID NO: 3 are conservative amino acid substitutions, preferably as shown in Table 1, of the corresponding amino acid residue of SEQ ID NO: 3, 14, 16, 18, 20, 22, 24, 26, or 28.

More preferably, the CASAR protein consists of or comprises an amino acid sequence having at least 80%, at least 85%, at least 90%, at least 95%, at least 98% or at least 99% sequence identity with an amino acid sequence as represented by SEQ ID NO: 3, 14, 16, 18, 20, 22, 24, 26, or 28, wherein at least 1, at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, at least 26, at least 27, at least 28, at least 29, or at least 30 of the non-identical amino acid residues, or wherein 1-10, 10-20, 20-30, 40-50, 50-60, 60-70, 70-80, 80-90 or 90-100 or even all of the non-identical amino acid residues are conservative amino acid substitutions, preferably as shown in Table 1, of the corresponding amino acid residue of SEQ ID NO: 3, 14, 16, 18, 20, 22, 24, 26, or 28.

Percentages of identity of a polypeptide or protein are indicated with reference to the entire amino acid sequence specifically disclosed herein.

Preferably, the CASAR protein comprises at least about 25, at least about 30, at least about 35, at least about 40, at least about 45, at least about 50, at least about 55, at least about 60, at least about 65, at least about 70, at least about 75, at least about 80, or at least about 85 preferably continuous amino acid residues, preferably counted from the N-terminus or the C-terminus of the amino acid sequence, or up to the full length of the amino acid sequence set out in SEQ ID NO: 3, 14, 16, 18, 20, 22, 24, 26, or 28.

Preferably, the CASAR polypeptide comprises about 25-30, about 30-35, about 35-40, about 40-45, about 45-50, about 50-55, about 55-60, about 60-65, about 65-70, about 70-75, about 75-80, or about 80-86 amino acids, preferably consecutive amino acids, preferably counted from the N-terminus or C-terminus of the amino acid sequence, or up to the full length of any of the amino acid sequences encoded by the nucleic acid sequences set out in SEQ ID NO: 3, 14, 16, 18, 20, 22, 24, 26, or 28.

Preferably, the CASAR protein comprises at least about 25, at least about 30, at least about 35, at least about 40, at least about 45, at least about 50, at least about 55, at least about 60, at least about 65, at least about 70, at least about 75, at least about 80, or at least about 85 preferably continuous amino acid residues, preferably counted from the N-terminus or the C-terminus of the amino acid sequence, or up to the full length of the amino acid sequence set out in SEQ ID NO: 3.

Preferably, the CASAR polypeptide comprises about 25-30, about 30-35, about 35-40, about 40-45, about 45-50, about 50-55, about 55-60, about 60-65, about 65-70, about 70-75, about 75-80, or about 80-86 amino acids, preferably consecutive amino acids, preferably counted from the N-terminus or C-terminus of the amino acid sequence, or up to the full length of any of the amino acid sequences encoded by the nucleic acid sequences set out in SEQ ID NO: 3.

The CASAR proteins described herein are useful in the constructs, methods, plants, harvestable parts and products of the invention.

Methods for Increasing Fungal Resistance; Methods for Modulating Gene Expression One embodiment of the invention is a method for increasing fungal resistance, preferably resistance to Phakopsoraceae, for example soy bean rust, in a plant, plant part, or plant cell by increasing the expression of a CASAR protein or a functional fragment, orthologue, paralogue or homologue thereof in comparison to wild-type plants, wild-type plant parts or wild-type plant cells.

The present invention also provides a method for increasing resistance to fungal pathogens, preferably to a heminecrotrophic pathogen, in particular to rust pathogens (i.e., fungal pathogens of the order Pucciniales), preferably fungal pathogens of the family Phakopsoraceae, preferably against fungal pathogens of the genus *Phakopsora*, most preferably against *Phakopsora pachyrhizi* and *Phakopsora meibomiae*, also known as soy bean rust in plants or plant cells, wherein in comparison to wild type plants, wild type plant parts, or wild type plant cells a CASAR protein is overexpressed.

The present invention further provides a method for increasing resistance to fungal pathogens of the genus *Phakopsora*, most preferably against *Phakopsora pachyrhizi* and *Phakopsora meibomiae*, also known as soy bean rust in plants or plant cells by overexpression of a CASAR protein.

In preferred embodiments, the protein amount and/or function of the CASAR protein in the plant is increased by at least 10%, at least 20%, at least 30%, at least 40%, at least 50%, at least 60%, at least 70%, at least 80%, at least 90%, or at least 95% or more in comparison to a wild type plant that is not transformed with the CASAR nucleic acid.

In one embodiment of the invention, the CASAR protein is encoded by (i) an exogenous nucleic acid having at least 60%, preferably at least 70%, for example at least 75%, more preferably at least 80%, for example at least 85%, even more preferably at least 90%, for example at least 95% or at least 96% or at least 97% or at least 98%, most preferably 99% identity with SEQ ID NO: 2, 1, 5-12, 13, 15, 17, 19, 21, 23, 25, or 27, a functional fragment thereof, or an orthologue or a paralogue thereof, or a splice variant thereof; or by (ii) an exogenous nucleic acid encoding a protein having at least 60% identity, preferably at least 70%, for example at least 75%, more preferably at least 80%, for example at least 85%, even more preferably at least 90%, for example at least 95% or at least 96% or at least 97% or at least 98% most preferably 99% homology with SEQ ID NO: 3, 14, 16, 18, 20, 22, 24, 26, or 28, a functional fragment thereof, an orthologue or a paralogue thereof, preferably the encoded protein confers enhanced fungal resistance relative to control plants;

(iii) an exogenous nucleic acid capable of hybridizing under stringent conditions with a complementary sequence of any of the nucleic acids according to (i) or (ii); preferably encoding a CASAR protein; preferably wherein the nucleic acid molecule codes for a polypeptide which has essentially identical properties to the polypeptide described in SEQ ID NO: 3; preferably the encoded protein confers enhanced fungal resistance relative to control plants; or by (iv) an exogenous nucleic acid encoding the same CASAR protein as any of the nucleic acids of (i) to (iii) above, but differing from the nucleic acids of (i) to (iii) above due to the degeneracy of the genetic code.

A method for increasing fungal resistance, preferably resistance to Phakopsoraceae, for example soy bean rust, in a plant, plant part, or plant cell, by increasing the expression of a CASAR protein or a functional fragment, orthologue, paralogue or homologue thereof, or a splice variant thereof, wherein the CASAR protein is encoded by (i) an exogenous nucleic acid having at least 60% identity, preferably at least 70% sequence identity, at least 80%, at least 90%, at least 95%, at least 98%, at least 99% sequence identity, or even 100% sequence identity with SEQ ID NO: 2, 1, 5-12, 13, 15, 17, 19, 21, 23, 25, or 27, or a functional fragment thereof, an orthologue or a paralogue thereof, or a splice variant thereof;

(ii) an exogenous nucleic acid encoding a protein having at least 60%, preferably at least 70% sequence identity, at least 80%, at least 90%, at least 95%, at least 98%, at least 99% sequence identity, or even 100% sequence identity with SEQ ID NO: 3, 14, 16, 18, 20, 22, 24, 26, or 28, a functional fragment thereof, an orthologue or a paralogue thereof; preferably the encoded protein confers enhanced fungal resistance relative to control plants;

(iii) an exogenous nucleic acid capable of hybridizing under stringent conditions with a complementary sequence of any of the nucleic acids according to (i) or (ii); preferably encoding a CASAR protein; preferably wherein the nucleic acid molecule codes for a polypeptide which has essentially identical properties to the polypeptide described in SEQ ID NO: 3; preferably the encoded protein confers enhanced fungal resistance relative to control plants; and/or by (iv) an exogenous nucleic acid encoding the same CASAR protein as any of the nucleic acids of (i) to (iii) above, but differing from the nucleic acids of (i) to (iii) above due to the degeneracy of the genetic code is a further embodiment of the invention.

A method for increasing fungal resistance, preferably resistance to Phakopsoraceae, for example soy bean rust, in a plant, plant part, or plant cell, by increasing the expression of a CASAR protein or a functional fragment, orthologue, paralogue or homologue thereof, or a splice variant thereof, wherein the CASAR protein is encoded by (i) an exogenous nucleic acid having at least 60% identity, preferably at least 70% sequence identity, at least 80%, at least 90%, at least 95%, at least 98%, at least 99% sequence identity, or even 100% sequence identity with SEQ ID NO: 2 or a functional fragment thereof, an orthologue or a paralogue thereof, or a splice variant thereof;

(ii) an exogenous nucleic acid encoding a protein having at least 60%, preferably at least 70% sequence identity, at least 80%, at least 90%, at least 95%, at least 98%, at least 99% sequence identity, or even 100% sequence identity with SEQ ID NO: 3, a functional fragment thereof, an orthologue or a paralogue thereof; preferably the encoded protein confers enhanced fungal resistance relative to control plants;

(iii) an exogenous nucleic acid capable of hybridizing under stringent conditions with a complementary sequence of any of the nucleic acids according to (i) or (ii); preferably encoding a CASAR protein; preferably wherein the nucleic acid molecule codes for a polypeptide which has essentially identical properties to the polypeptide described in SEQ ID NO: 3; preferably the encoded protein confers enhanced fungal resistance relative to control plants; and/or by (iv) an exogenous nucleic acid encoding the same CASAR protein as any of the nucleic acids of (i) to (iii) above, but differing from the nucleic acids of (i) to (iii) above due to the degeneracy of the genetic code is a further embodiment of the invention.

In a further method of the invention, the method comprises the steps of (a) stably transforming a plant cell with a recombinant expression cassette comprising
  (i) a nucleic acid having at least 60% identity, preferably at least 70% sequence identity, at least 80%, at least 90%, at least 95%, at least 98%, at least 99% sequence identity, or even 100% sequence identity with SEQ ID NO: 2, 1, 5-12, 13, 15, 17, 19, 21, 23, 25, or 27, or a functional fragment thereof, or an orthologue or a paralogue thereof, or a splice variant thereof;
  (ii) a nucleic acid coding for a protein having at least 60% identity, preferably at least 70% sequence identity, at least 80%, at least 90%, at least 95%, at least 98%, at least 99% sequence identity, or even 100% sequence identity with SEQ ID NO: 3, 14, 16, 18, 20, 22, 24, 26, or 28, a functional fragment thereof, an orthologue or a paralogue thereof; preferably the encoded protein confers enhanced fungal resistance relative to control plants;
  (iii) a nucleic acid capable of hybridizing under stringent conditions with a complementary sequence of any of the nucleic acids according to (i) or (ii); preferably encoding a CASAR protein; preferably wherein the nucleic acid molecule codes for a polypeptide which has essentially identical properties to the polypeptide described in SEQ ID NO: 3; preferably the encoded protein confers enhanced fungal resistance relative to control plants; and/or
  (iv) a nucleic acid encoding the same CASAR polypeptide as any of the nucleic acids of (i) to (iii) above, but differing from the nucleic acids of (i) to (iii) above due to the degeneracy of the genetic code, in functional linkage with a promoter;

(b) regenerating the plant from the plant cell; and (c) expressing said nucleic acid, optionally wherein the nucleic acid which codes for a CASAR protein is expressed in an amount and for a period sufficient to generate or to increase soybean rust resistance in said plant.

Preferably, the method comprises the steps of (a) stably transforming a plant cell with a recombinant expression cassette comprising
  (i) a nucleic acid having at least 60% identity, preferably at least 70% sequence identity, at least 80%, at least 90%, at least 95%, at least 98%, at least 99% sequence identity, or even 100% sequence identity with SEQ ID NO: 2, or a functional fragment thereof, or an orthologue or a paralogue thereof, or a splice variant thereof;
  (ii) a nucleic acid coding for a protein having at least 60% identity, preferably at least 70% sequence identity, at least 80%, at least 90%, at least 95%, at least 98%, at least 99% sequence identity, or even 100% sequence identity with SEQ ID NO: 3, a functional fragment thereof, an orthologue or a paralogue thereof; preferably the encoded protein confers enhanced fungal resistance relative to control plants;
  (iii) a nucleic acid capable of hybridizing under stringent conditions with a complementary sequence of any of the nucleic acids according to (i) or (ii); preferably encoding a CASAR protein; preferably wherein the nucleic acid molecule codes for a polypeptide which has essentially identical properties to the polypeptide described in SEQ ID NO: 3; preferably the encoded protein confers enhanced fungal resistance relative to control plants; and/or
  (iv) a nucleic acid encoding the same CASAR polypeptide as any of the nucleic acids of (i) to (iii) above, but differing from the nucleic acids of (i) to (iii) above due to the degeneracy of the genetic code, in functional linkage with a promoter;
(b) regenerating the plant from the plant cell; and
(c) expressing said nucleic acid, optionally wherein the nucleic acid which codes for a CASAR protein is expressed in an amount and for a period sufficient to generate or to increase soybean rust resistance in said plant.

Preferably, the promoter is a rust induced and/or mesophyll-specific promoter, preferably the rust induced mesophyll specific promoter 820, preferably, as shown in SEQ ID NO: 4.

Preferably, the method for increasing fungal resistance, preferably resistance to Phakopsoraceae, for example soy bean rust, in a plant, plant part, or plant cell further comprises the step of selecting a transgenic plant expressing (i) an exogenous nucleic acid having at least 60% identity, preferably at least 70% sequence identity, at least 80%, at least 90%, at least 95%, at least 98%, at least 99% sequence identity, or even 100% sequence identity with SEQ ID NO: 2, 1, 5-12, 13, 15, 17, 19, 21, 23, 25, or 27, or a functional fragment thereof, or an orthologue or a paralogue thereof, or a splice variant thereof;
(ii) an exogenous nucleic acid coding for a protein having at least 60% identity, preferably at least 70% sequence identity, at least 80%, at least 90%, at least 95%, at least 98%, at least 99% sequence identity, or even 100% sequence identity with SEQ ID NO: 3, 14, 16, 18, 20, 22, 24, 26, or 28, a functional fragment thereof, an orthologue or a paralogue thereof; preferably the encoded protein confers enhanced fungal resistance relative to control plants;
(iii) an exogenous nucleic acid capable of hybridizing under stringent conditions a complementary sequence of any of the nucleic acids according to (i) or (ii); preferably encoding a CASAR protein; preferably wherein the nucleic acid molecule codes for a polypeptide which has essentially identical properties to the polypeptide described in SEQ ID NO: 3; preferably the encoded protein confers enhanced fungal resistance relative to control plants; and/or
(iv) an exogenous nucleic acid encoding the same CASAR polypeptide as any of the nucleic acids of (i) to (iii) above, but differing from the nucleic acids of (i) to (iii) above due to the degeneracy of the genetic code.

A preferred embodiment is a method for increasing resistance to soy bean rust in a soy bean plant, soy bean plant part, or soy bean plant cell, by increasing the expression of a CASAR protein, wherein the CASAR protein is encoded by (i) an exogenous nucleic acid having at least 80%, at least 90%, at least 95%, at least 98%, at least 99% sequence identity, or even 100% sequence identity with SEQ ID NO: 2, 1, 5-12, 13, 15, 17, 19, 21, 23, 25, or 27;
(ii) an exogenous nucleic acid encoding a protein having at least 80%, at least 90%, at least 95%, at least 98%, at least 99% sequence identity, or even 100% sequence identity with SEQ ID NO: 3, 14, 16, 18, 20, 22, 24, 26, or 28; preferably the encoded protein confers enhanced fungal resistance relative to control plants;
(iii) an exogenous nucleic acid capable of hybridizing under stringent conditions with a complementary sequence of any of the nucleic acids according to (i) or (ii); preferably encoding a CASAR protein; preferably wherein the nucleic acid molecule codes for a polypeptide which has essentially identical properties to the polypeptide described in SEQ ID NO: 3; preferably the encoded protein confers enhanced fungal resistance relative to control plants; and/or by
(iv) an exogenous nucleic acid encoding the same CASAR protein as any of the nucleic acids of (i) to (iii) above, but differing from the nucleic acids of (i) to (iii) above due to the degeneracy of the genetic code, wherein increasing the expression of the CASAR protein is achieved by transforming the soy bean plant, plant part or plant cell with a nucleic acid comprising the nucleic acid set out under item (i) or (ii) or (iii) or (iv).

Also a preferred embodiment is a method for increasing resistance to soy bean rust in a soy bean plant, soy bean plant part, or soy bean plant cell, by increasing the expression of a CASAR protein, wherein the CASAR protein is encoded by (i) an exogenous nucleic acid having at least 80%, at least 90%, at least 95%, at least 98%, at least 99% sequence identity, or even 100% sequence identity with SEQ ID NO: 2, 1, 5-12, 13, 15, 17, 19, 21, 23, 25, or 27;
(ii) an exogenous nucleic acid encoding a protein having at least 80%, at least 90%, at least 95%, at least 98%, at least 99% sequence identity, or even 100% sequence identity with SEQ ID NO: 3, 14, 16, 18, 20, 22, 24, 26, or 28; preferably the encoded protein confers enhanced fungal resistance relative to control plants; or
(iii) an exogenous nucleic acid encoding the same CASAR protein as any of the nucleic acids of (i) to (ii) above, but differing from the nucleic acids of (i) to (ii) above due to the degeneracy of the genetic code, wherein increasing the expression of the CASAR protein is achieved by transforming the soy bean plant, plant part or plant cell with a nucleic acid comprising the nucleic acid set out under item (i) or (ii) or (iii).

The fungal pathogens or fungus-like pathogens (such as, for example, Chromista) can belong to the group comprising Plasmodiophoramycota, Oomycota, Ascomycota, Chytridiomycetes, Zygomycetes, Basidiomycota or Deuteromycetes (*Fungi imperfecti*). Pathogens which may be mentioned by way of example, but not by limitation, are those detailed in Tables 2 and 3, and the diseases which are associated with them.

TABLE 2

| Diseases caused by biotrophic and/or heminecrotrophic phytopathogenic fungi | |
|---|---|
| Disease | Pathogen |
| Leaf rust | *Puccinia recondita* |
| Yellow rust | *P. striiformis* |
| Powdery mildew | *Erysiphe graminis/Blumeria grarrinis* |

TABLE 2-continued

| Diseases caused by biotrophic and/or heminecrotrophic phytopathogenic fungi | |
|---|---|
| Disease | Pathogen |
| Rust (common corn) | *Puccinia sorghi* |
| Rust (Southern corn) | *Puccinia polysora* |
| Tobacco leaf spot | *Cercospora nicotianae* |
| Rust (soybean) | *Phakopsora pachyrhizi*, *P. meibomiae* |
| Rust (tropical corn) | *Physopella pallescens*, *P. zeae* = *Angiopsora zeae* |

TABLE 3

| Diseases caused by necrotrophic and/or hemibiotrophic fungi and Oomycetes | |
|---|---|
| Disease | Pathogen |
| Plume blotch | *Septoria* (*Stagonospora*) *nodorurr* |
| Leaf blotch | *Septoria tritici* |
| Ear fusarioses | *Fusarium* spp. |
| Late blight | *Phytophthora infestans* |
| Anthrocnose leaf blight<br>Anthracnose stalk rot | *Colletotrichum graminicola* (teleomorph: *Glomerella graminicola* Politis); *Glomerella tucumanensis* (anamorph: *Glomerella falcatum* Went) |
| *Curvularia* leaf spot | *Curvularia clavata*, *C. eragrostidis*, = *C. maculans* (teleomorph: *Cochliobolus eragrostidis*), *Curvularia inaequalis*, *C. intermedia* (teleomorph: *Cochliobolus intermedius*), *Curvularia lunata* (teleomorph: *Cochliobolus lunatus*), *Curvularia pallescens* (teleomorph: *Cochliobolus pallescens*), *Curvularia senegalensis*, *C. tuberculata* (teleomorph: *Cochliobolus tuberculatus*) |
| *Didymella* leaf spot | *Didymella exitalis* |
| *Diplodia* leaf spot or streak | *Stenocarpella macrospora* = *Diplodialeaf macrospora* |
| Brown stripe downy mildew | *Sclerophthora rayssiae* var. *zeae* |
| Crazy top downy mildew | *Sclerophthora macrospora* = *Sclerospora macrospora* |
| Green ear downy mildew (*graminicola* downy mildew) | *Sclerospora graminicola* |
| Leaf spots, minor | *Alternaria alternata*, *Ascochyta maydis*, *A. tritici*, *A. zeicola*, *Bipolaris victoriae* = *Helminthosporium victoriae* (teleomorph: *Cochliobolus victoriae*), *C. sativus* (anamorph: *Bipolaris sorokiniana* = *H. sorokinianum* = *H. sativum*), *Epicoccum nigrum*, *Exserohilum prolatum* = *Drechslera prolata* (teleomorph: *Setosphaeria prolata*) *Graphium penicillioides*, *Leptosphaeria maydis*, *Leptothyrium zeae*, *Ophiosphaerella herpotricha*, (anamorph: *Scolecosporiella* sp.), *Paraphaeosphaeria michotii*, *Phoma* sp., *Septoria zeae*, *S. zeicola*, *S. zeina* |
| Northern corn leaf blight (white blast, crown stalk rot, stripe) | *Setosphaeria turcica* (anamorph: *Exserohilum turcicum* = *Helminthosporium turcicum*) |
| Northern corn leaf spot<br>*Helminthosporium* ear rot (race 1) | *Cochliobolus carbonum* (anamorph: *Bipolaris zeicola* = *Helminthosporium carbonum*) |
| *Phaeosphaeria* leaf spot | *Phaeosphaeria maydis* = *Sphaerulina maydis* |
| Rostratum leaf spot (*Helminthosporium* leaf disease, ear and stalk rot) | *Setosphaeria rostrata*, (anamorph: *xserohilum rostratum* = *Helminthosporium rostratum*) |
| Java downy mildew | *Peronosclerospora maydis* = *Sclerospora maydis* |
| Philippine downy mildew | *Peronosclerospora philippinensis* = *Sclerospora philippinensis* |
| *Sorghum* downy mildew | *Peronosclerospora sorghi* = *Sclerospora sorghi* |
| *Spontaneum* downy mildew | *Peronosclerospora spontanea* = *Sclerospora spontanea* |
| Sugarcane downy mildew | *Peronosclerospora sacchari* = *Sclerospora sacchari* |
| *Sclerotium* ear rot (southern blight) | *Sclerotium rolfsii* Sacc. (teleomorph: *Athelia rolfsii*) |
| Seed rot-seedling blight | *Bipolaris sorokiniana*, *B. zeicola* = *Helminthosporium carbonum*, *Diplodia maydis*, *Exserohilum pedicillatum*, *Exserohilum turcicum* = *Helminthosporium turcicum*, *Fusarium avenaceum*, *F. culmorum*, *F. moniliforme*, *Gibberella zeae* (anamorph: *F. graminearum*), *Macrophomina phaseolina*, *Penicillium* spp., *Phomopsis* sp., *Pythium* spp., *Rhizoctonia solani*, *R. zeae*, *Sclerotium rolfsii*, *Spicaria* sp. |

TABLE 3-continued

| Diseases caused by necrotrophic and/or hemibiotrophic fungi and Oomycetes | |
|---|---|
| Disease | Pathogen |
| *Selenophoma* leaf spot | *Selenophoma* sp. |
| Yellow leaf blight | *Ascochyta ischaemi*, *Phyllosticta maydis* (teleomorph: *Mycosphaerella zeae-maydis*) |
| Zonate leaf spot | *Gloeocercospora sorghi* |

The following are especially preferred:

Plasmodiophoromycota such as *Plasmodiophora brassicae* (clubroot of crucifers), *Spongospora subterranea, Polymyxa graminis,*

Oomycota such as *Bremia lactucae* (downy mildew of lettuce), *Peronospora* (downy mildew) in snapdragon (*P. antirrhini*), onion (*P. destructor*), spinach (*P. effusa*), soybean (*P. manchurica*), tobacco ("blue mold"; *P. tabacina*) alfalfa and clover (*P. trifolium*), *Pseudoperonospora humuli* (downy mildew of hops), *Plasmopara* (downy mildew in grapevines) (*P. viticola*) and sunflower (*P. halstedii*), *Sclerophthora macrospora* (downy mildew in cereals and grasses), *Pythium* (for example damping-off of Beta beet caused by *P. debaryanum*), *Phytophthora infestans* (late blight in potato and in tomato and the like), *Albugo* spec.

Ascomycota such as *Microdochium nivale* (snow mold of rye and wheat), *Fusarium, Fusarium graminearum, Fusarium culmorum* (partial ear sterility mainly in wheat), *Fusarium oxysporum* (*Fusarium* wilt of tomato), *Blumeria graminis* (powdery mildew of barley (f.sp. *hordei*) and wheat (f.sp. *tritici*)), *Erysiphe pisi* (powdery mildew of pea), *Nectria galligena* (*Nectria* canker of fruit trees), *Uncinula necator* (powdery mildew of grapevine), *Pseudopeziza tracheiphila* (red fire disease of grapevine), *Claviceps purpurea* (ergot on, for example, rye and grasses), *Gaeumannomyces graminis* (take-all on wheat, rye and other grasses), *Magnaporthe grisea, Pyrenophora graminea* (leaf stripe of barley), *Pyrenophora teres* (net blotch of barley), *Pyrenophora tritici-repentis* (leaf blight of wheat), *Venturia inaequalis* (apple scab), *Sclerotinia sclerotium* (stalk break, stem rot), *Pseudopeziza medicaginis* (leaf spot of alfalfa, white and red clover).

Basidiomycetes such as *Typhula incarnata* (*typhula* blight on barley, rye, wheat), *Ustilago maydis* (blister smut on maize), *Ustilago nuda* (loose smut on barley), *Ustilago tritici* (loose smut on wheat, spelt), *Ustilago avenae* (loose smut on oats), *Rhizoctonia solani* (*rhizoctonia* root rot of potato), *Sphacelotheca* spp. (head smut of sorghum), *Melampsora lini* (rust of flax), *Puccinia graminis* (stem rust of wheat, barley, rye, oats), *Puccinia recondita* (leaf rust on wheat), *Puccinia dispersa* (brown rust on rye), *Puccinia hordei* (leaf rust of barley), *Puccinia coronata* (crown rust of oats), *Puccinia striiformis* (yellow rust of wheat, barley, rye and a large number of grasses), *Uromyces appendiculatus* (brown rust of bean), *Sclerotium rolfsii* (root and stem rots of many plants).

Deuteromycetes (*Fungi imperfecti*) such as *Septoria* (*Stagonospora*) *nodorum* (glume blotch) of wheat (*Septoria tritici*), *Pseudocercosporella herpotrichoides* (eyespot of wheat, barley, rye), *Rynchosporium secalis* (leaf spot on rye and barley), *Alternaria solani* (early blight of potato, tomato), *Phoma betae* (blackleg on Beta beet), *Cercospora beticola* (leaf spot on Beta beet), *Alternaria brassicae* (black spot on oilseed rape, cabbage and other crucifers), *Verticillium dahliae* (*verticillium* wilt), *Colletotrichum, Colletotrichum lindemuthianum* (bean anthracnose), *Phoma lingam* (blackleg of cabbage and oilseed rape), *Botrytis cinerea* (grey mold of grapevine, strawberry, tomato, hops and the like).

Especially preferred are biotrophic pathogens, e.g., *Phakopsora pachyrhizi* and/or those pathogens which have essentially a similar infection mechanism as *Phakopsora pachyrhizi*, as described herein. Particularly preferred are pathogens from the subclass Pucciniomycetes, preferably from the order Pucciniales (rust), previously also known as Uredinales, among which in particular the Melompsoraceae. Preferred are Phakopsoraceae, more preferably *Phakopsora*. Especially preferred are *Phakopsora pachyrhizi* and/or *Phakopsora meibomiae.*

Also preferred rust fungi are selected from the group of *Puccinia, Gymnosporangium, Juniperus, Cronartium, Hemileia*, and *Uromyces*, preferably *Puccinia sorghi, Gymnosporangium juniperi-virginianae, Juniperus virginiana, Cronartium ribicola, Hemlleia vastatrix, Puccinia graminis, Puccinia coronata, Uromyces phaseoli, Puccinia hemerocallldis, Puccinia persistens* subsp. *Triticina, Puccinia striiformis, Puccinia graminis* causes, and/or *Uromyces appendeculatus.*

CASAR Expression Constructs and Vector Constructs

A recombinant nucleic acid, expression cassette or vector construct preferably comprises a natural gene and a natural promoter, a natural gene and a non-natural promoter, a non-natural gene and a natural promoter, or a non-natural gene and a non-natural promoter.

If protein expression is desired, it is generally desirable to include a transcription termination sequence, e.g., a polyadenylation region at the 3'-end of a polynucleotide coding region. The polyadenylation region can be derived from the natural gene, from a variety of other plant genes, or from T-DNA. The 3' end sequence to be added may be derived from, for example, the nopaline synthase or octopine synthase genes, or alternatively from another plant gene, or less preferably from any other eukaryotic gene.

A recombinant vector construct comprising:

(a) (i) a nucleic acid having at least 60% identity, preferably at least 70% sequence identity, at least 80%, at least 90%, at least 95%, at least 98%, at least 99% sequence identity, or even 100% sequence identity with SEQ ID NO: 2, 1, 5-12, 13, 15, 17, 19, 21, 23, 25, or 27, or a functional fragment thereof, or an orthologue or a paralogue thereof, or a splice variant thereof;

(ii) a nucleic acid coding for a protein having at least 60% identity, preferably at least 70% sequence identity, at least 80%, at least 90%, at least 95%, at least 98%, at least 99% sequence identity, or even 100% sequence identity with SEQ ID NO: 3, 14, 16, 18, 20, 22, 24, 26, or 28, a functional fragment thereof, an orthologue or a paralogue thereof; preferably the encoded protein confers enhanced fungal resistance relative to control plants;

(iii) a nucleic acid capable of hybridizing under stringent conditions with a complementary sequence of any of the nucleic acids according to (i) or (ii); preferably encoding a CASAR protein; preferably wherein the nucleic acid molecule codes for a polypeptide which has essentially identical properties to the polypeptide described in SEQ ID NO: 3; preferably the encoded protein confers enhanced fungal resistance relative to control plants; and/or (iv) a nucleic acid encoding the same CASAR protein as any of the nucleic acids of (i) to (iii) above, but differing from the nucleic acids of (i) to (iii) above due to the degeneracy of the genetic code, operably linked with (b) a promoter and (c) a transcription termination sequence is a further embodiment of the invention.

Furthermore, a recombinant vector construct is provided comprising:

(a) (i) a nucleic acid having at least 80%, at least 90%, at least 95%, at least 98%, at least 99% sequence identity, or even 100% sequence identity with SEQ ID NO: 2, 1, 5-12, 13, 15, 17, 19, 21, 23, 25, or 27;

(ii) a nucleic acid coding for a protein having at least 80%, at least 90%, at least 95%, at least 98%, at least 99% sequence identity, or even 100% sequence identity with SEQ ID NO: 3, 14, 16, 18, 20, 22, 24, 26, or 28; preferably the encoded protein confers enhanced fungal resistance relative to control plants;

(iii) a nucleic acid capable of hybridizing under stringent conditions with a complementary sequence of any of the nucleic acids according to (i) or (ii); preferably encoding a CASAR protein; preferably wherein the nucleic acid molecule codes for a polypeptide which has essentially identical properties to the polypeptide described in SEQ ID NO: 3; preferably the encoded protein confers enhanced fungal resistance relative to control plants; and/or (iv) a nucleic acid encoding the same CASAR protein as any of the nucleic acids of (i) to (iii) above, but differing from the nucleic acids of (i) to (iii) above due to the degeneracy of the genetic code, operably linked with (b) a promoter and (c) a transcription termination sequence is a further embodiment of the invention.

Furthermore, a recombinant vector construct is provided comprising:

(a) (i) a nucleic acid having at least 80%, at least 90%, at least 95%, at least 98%, at least 99% sequence identity, or even 100% sequence identity with SEQ ID NO: 2;

(ii) a nucleic acid coding for a protein having at least 80%, at least 90%, at least 95%, at least 98%, at least 99% sequence identity, or even 100% sequence identity with SEQ ID NO: 3; preferably the encoded protein confers enhanced fungal resistance relative to control plants;

(iii) a nucleic acid capable of hybridizing under stringent conditions with a complementary sequence of any of the nucleic acids according to (i) or (ii); preferably encoding a CASAR protein; preferably wherein the nucleic acid molecule codes for a polypeptide which has essentially identical properties to the polypeptide described in SEQ ID NO: 3; preferably the encoded protein confers enhanced fungal resistance relative to control plants; and/or (iv) a nucleic acid encoding the same CASAR protein as any of the nucleic acids of (i) to (iii) above, but differing from the nucleic acids of (i) to (iii) above due to the degeneracy of the genetic code, operably linked with (b) a promoter and (c) a transcription termination sequence is a further embodiment of the invention.

In the case of a genomic library, the natural genetic environment of the nucleic acid sequence is preferably retained, at least in part. The environment preferably flanks the nucleic acid sequence at least on one side and has a sequence length of at least 50 bp, preferably at least 500 bp, especially preferably at least 1000 bp, most preferably at least 5000 bp.

Promoters according to the present invention may be constitutive, inducible, in particular pathogen-inducible, developmental stage-preferred, cell type-preferred, tissue-preferred or organ-preferred. Preferably, the promoter is a non-natural promoter. Constitutive promoters are active under most conditions. Non-limiting examples of constitutive promoters include the CaMV 19S and 35S promoters (Odell et al., 1985, Nature 313:810-812), the sX CaMV 35S promoter (Kay et al., 1987, Science 236:1299-1302), the Sep1 promoter, the rice actin promoter (McElroy et al., 1990, Plant Cell 2:163-171), the *Arabidopsis* actin promoter, the ubiquitin promoter (Christensen et al., 1989, Plant Molec. Biol. 18:675-689); pEmu (Last et al., 1991, Theor. Appl. Genet. 81:581-588), the figwort mosaic virus 35S promoter, the Smas promoter (Velten et al., 1984, EMBO J. 3:2723-2730), the GRP1-8 promoter, the cinnamyl alcohol dehydrogenase promoter (U.S. Pat. No. 5,683,439), promoters from the T-DNA of *Agrobacterium*, such as mannopine synthase, nopaline synthase, and octopine synthase, the small subunit of ribulose biphosphate carboxylase (ssu-RUBISCO) promoter, and/or the like.

Preferably, the expression vector of the invention comprises a constitutive promoter, mesophyll-specific promoter, epidermis-specific promoter, root-specific promoter, a pathogen inducible promoter, or a fungal-inducible promoter.

A promoter is inducible, if its activity, measured on the amount of RNA produced under control of the promoter, is at least 30%, at least 40%, at least 50% preferably at least 60%, at least 70%, at least 80%, at least 90% more preferred at least 100%, at least 200%, at least 300% higher in its induced state, than in its un-induced state. A promoter is cell-, tissue- or organ-specific, if its activity, measured on the amount of RNA produced under control of the promoter, is at least 30%, at least 40%, at least 50% preferably at least 60%, at least 70%, at least 80%, at least 90% more preferred at least 100%, at least 200%, at least 300% higher in a particular cell-type, tissue or organ, then in other cell-types or tissues of the same plant, preferably the other cell-types or tissues are cell types or tissues of the same plant organ, e.g. a root. In the case of organ specific promoters, the promoter activity has to be compared to the promoter activity in other plant organs, e.g. leaves, stems, flowers or seeds. Preferably, the promoter is a constitutive promoter, mesophyll-specific promoter, or epidermis-specific promoter.

In preferred embodiments, the increase in the protein amount and/or activity of the CASAR protein takes place in a constitutive or tissue-specific manner. In especially preferred embodiments, an essentially pathogen-induced increase in the protein amount and/or protein activity takes place, for example by recombinant expression of the CASAR nucleic acid under the control of a fungal-inducible promoter. In particular, the expression of the CASAR nucleic acid takes place on fungal infected sites, where, however, preferably the expression of the CASAR nucleic acid remains essentially unchanged in tissues not infected by fungus.

Developmental stage-preferred promoters are preferentially expressed at certain stages of development. Tissue and organ preferred promoters include those that are preferentially expressed in certain tissues or organs, such as leaves, roots, seeds, or xylem. Examples of tissue preferred and organ preferred promoters include, but are not limited to fruit-preferred, ovule-preferred, male tissue-preferred, seed-preferred, integument-preferred, tuber-preferred, stalk-preferred, pericarp-preferred, leaf-preferred, stigma-preferred, pollen-preferred, anther-preferred, a petal-preferred, sepal-preferred, pedicel-preferred, silique-preferred, stem-preferred, root-preferred promoters and/or the like. Seed preferred promoters are preferentially expressed during seed development and/or germination. For example, seed preferred promoters can be embryo-preferred, endosperm preferred and seed coat-preferred. See Thompson et al., 1989, BioEssays 10:108. Examples of seed preferred promoters include, but are not limited to cellulose synthase (celA), Cim1, gamma-zein, globulin-1, maize 19 kD zein (cZ19B1) and/or the like.

Other suitable tissue-preferred or organ-preferred promoters include, but are not limited to, the napin-gene promoter from rapeseed (U.S. Pat. No. 5,608,152), the USP-promoter from *Vicia faba* (Baeumlein et al., 1991, Mol Gen Genet. 225(3):459-67), the oleosin-promoter from *Arabidopsis* (PCT Application No. WO 98/45461), the phaseolin-promoter from *Phaseolus vulgaris* (U.S. Pat. No. 5,504,200), the Bce4-promoter from *Brassica* (PCT Application No. WO 91/13980), or the legumin B4 promoter (LeB4; Baeumlein et al., 1992, Plant Journal, 2(2):233-9), as well as promoters conferring seed specific expression in monocot plants like maize, barley, wheat, rye, rice, etc. Suitable promoters to note are the Ipt2 or Ipt1-gene promoter from barley (PCT Application No. WO 95/15389 and PCT Application No. WO 95/23230) or those described in PCT Application No. WO 99/16890 (promoters from the barley hordein-gene, rice glutelin gene, rice oryzin gene, rice prolamin gene, wheat gliadin gene, wheat glutelin gene, oat glutelin gene, Sorghum kasirin-gene, and/or rye secalin gene).

Promoters useful according to the invention include, but are not limited to, are the major chlorophyll a/b binding protein promoter, histone promoters, the Ap3 promoter, the β-conglycin promoter, the napin promoter, the soybean lectin promoter, the maize 15 kD zein promoter, the 22 kD zein promoter, the 27 kD zein promoter, the g-zein promoter, the waxy, shrunken 1, shrunken 2, bronze promoters, the Zm13 promoter (U.S. Pat. No. 5,086,169), the maize polygalacturonase promoters (PG) (U.S. Pat. Nos. 5,412,085 and 5,545,546), the SGB6 promoter (U.S. Pat. No. 5,470,359), as well as synthetic or other natural promoters.

Epidermis-specific promoters may be selected from the group consisting of:

WIR5 (=GstA1); acc. X56012; Dudler & Schweizer,

GLP4, acc. AJ310534; Wei Y., Zhang Z., Andersen C. H., Schmelzer E., Gregersen P. L., Collinge D. B., Smedegaard-Petersen V. and Thordal-Christensen H., Plant Molecular Biology 36, 101 (1998), GLP2a, acc. AJ237942, Schweizer P., Christoffel A. and Dudler R., Plant J. 20, 541 (1999); Prx7, acc. AJ003141, Kristensen B. K., Ammitzböll H., Rasmussen S. K. and Nielsen K. A., Molecular Plant Pathology, 2(6), 311 (2001);

GerA, acc. AF250933; Wu S., Druka A., Horvath H., Kleinhofs A., Kannangara G. and von Wettstein D., Plant Phys Biochem 38, 685 (2000);

OsROC1, acc. AP004656

RTBV, acc. AAV62708, AAV62707; Klöti A., Henrich C., Bieri S., He X., Chen G., Burkhardt P. K., Wünn J., Lucca P., Hohn T., Potrykus I. and Fütterer J., PMB 40, 249 (1999);

Chitinase ChtC2-Promoter from potato (Ancillo et al., Planta. 217(4), 566, (2003));

AtProT3 Promoter (Grallath et al., Plant Physiology. 137(1), 117 (2005));

SHN-Promoters from *Arabidopsis* (AP2/EREBP transcription factors involved in cutin and wax production) (Aarón et al., Plant Cell. 16(9), 2463 (2004)); and/or GSTA1 from wheat (Dudler et al., WP2005306368 and Altpeter et al., Plant Molecular Biology. 57(2), 271 (2005)).

Mesophyll-specific promoters may be selected from the group consisting of:

PPCZm1 (=PEPC); Kausch A. P., Owen T. P., Zachwieja S. J., Flynn A. R. and Sheen J., Plant Mol. Biol. 45, 1 (2001);

OsrbcS, Kyozuka et al., PlaNT Phys 102, 991 (1993); Kyozuka J., McElroy D., Hayakawa T., Xie Y., Wu R. and Shimamoto K., Plant Phys. 102, 991 (1993); OsPPDK, acc. AC099041;

TaGF-2.8, acc. M63223; Schweizer P., Christoffel A. and Dudler R., Plant J. 20, 541 (1999);

TaFBPase, acc. X53957;

TaWIS1, acc. AF467542; US 200220115849;

HvBIS1, acc. AF467539; US 200220115849;

ZmMIS1, acc. AF467514; US 200220115849;

HvPR1a, acc. X74939; Bryngelsson et al., Mol. Plant Microbe Interacti. 7 (2), 267 (1994);

HvPR1 b, acc. X74940; Bryngelsson et al., Mol. Plant Microbe Interact. 7(2), 267 (1994);

HvB1,3gluc; acc. AF479647;

HvPrx8, acc. AJ276227; Kristensen et al., Molecular Plant Pathology, 2(6), 311 (2001); and/or HvPAL, acc. X97313; Wei Y., Zhang Z., Andersen C. H., Schmelzer E., Gregersen P. L., Collinge D. B., Smedegaard-Petersen V. and Thordal-Christensen H. Plant Molecular Biology 36, 101 (1998)

Rust induced mesophyll specific promoter 820, as shown in SEQ ID NO: 4.

Constitutive promoters may be selected from the group consisting of:

PcUbi promoter from parsley (WO 03/102198)

CaMV 35S promoter: Cauliflower Mosaic Virus 35S promoter (Benfey et al. 1989 EMBO J. 8(8): 2195-2202), STPT promoter: *Arabidopsis thaliana* Short Triose phosphate translocator promoter (Accession NM_123979)

Act1 promoter: *Oryza sativa* actin 1 gene promoter (McElroy et al. 1990 PLANT CELL 2(2) 163-171 a) and/or EF1A2 promoter: *Glycine max* translation elongation factor EF1 alpha (US 20090133159).

In preferred embodiments, the increase in the protein quantity or function of the CASAR protein takes place in a constitutive or tissue-specific manner. In especially preferred embodiments, an essentially pathogen-induced increase in the protein quantity or protein function takes place, for example by exogenous expression of the CASAR nucleic acid under the control of a fungal-inducible promoter, preferably a rust-inducible promoter. In particular, the expression of the CASAR nucleic acid takes place on fungal infected sites, where, however, preferably the expression of the CASAR nucleic acid sequence remains essentially unchanged in tissues not infected by fungus.

Preferably, the CASAR nucleic acid is under the control of a rust induced mesophyll specific promoter. More preferably, the promoter is the rust induced mesophyll specific promoter 820, preferably, as shown in SEQ ID NO: 4. Preferably, the rust induced mesophyll specific promoter comprises a nucleic acid sequence which is at least 70%, at least 80%, at least 85%, at least 90%, at least 95%, at least 98%, or at least 99% identical with the nucleic acid sequence shown in SEQ ID NO: 4.

A preferred terminator is the terminator of the cathepsin D inhibitor gene from *Solanum* tuberosum.

Preferred promoter-terminator combinations with the gene of interest in between are a promoter from parsley, preferably, the parsley ubiquitine promoter, in combination with the terminator of the cathepsin D inhibitor gene from *Solanum tuberosum*. Another preferred promoter-terminator combination is the rust induced mesophyll specific promoter 820 in combination with the terminator of the cathepsin D inhibitor gene from *Solanum tuberosum*.

An intron sequence may also be added to the 5' untranslated region (UTR) and/or the coding sequence of the partial coding sequence to increase the amount of the mature message that accumulates in the cytosol. Inclusion of a spliceable intron in the transcription unit in both plant and animal expression constructs has been shown to increase gene expression at both the mRNA and protein levels up to 1000-fold (Buchman and Berg (1988) Mol. Cell biol. 8: 4395-4405; Callis et al. (1987) Genes Dev 1:1183-1200). Such intron enhancement of gene expression is typically greatest when placed near the 5' end of the transcription unit. Use of the maize introns Adh1-S intron 1, 2, and 6, the Bronze-1 intron are known in the art. For general information see: The Maize Handbook, Chapter 116, Freeling and Walbot, Eds., Springer, N.Y. (1994).

One type of vector construct is a "plasmid," which refers to a circular double stranded DNA loop into which additional DNA segments can be ligated. Another type of vector is a viral vector, wherein additional DNA segments can be ligated into the viral genome. Certain vector constructs are capable of autonomous replication in a host plant cell into which they are introduced. Other vector constructs are integrated into the genome of a host plant cell upon introduction into the host cell, and thereby are replicated along with the host genome. In particular the vector construct is capable of directing the expression of gene to which the vectors is operatively linked. However, the invention is intended to include such other forms of expression vector constructs, such as viral vectors (e.g., potato virus X, tobacco rattle virus, and/or Gemini virus), which serve equivalent functions.

Transgenic Organisms; Transgenic Plants, Plant Parts, and Plant Cells

A preferred embodiment is a transgenic plant, transgenic plant part, or transgenic plant cell overexpressing an exogenous CASAR protein. Preferably, the CASAR protein overexpressed in the plant, plant part or plant cell is encoded by (i) an exogenous nucleic acid having at least 60% identity with SEQ ID NO: 2, 1, 5-12, 13, 15, 17, 19, 21, 23, 25, or 27, or a functional fragment thereof, an orthologue or a paralogue thereof, or a splice variant thereof; or by (ii) an exogenous nucleic acid encoding a protein having at least 60% identity with SEQ ID NO: 3, 14, 16, 18, 20, 22, 24, 26, or 28, a functional fragment thereof, an orthologue or a paralogue thereof; preferably the encoded protein confers enhanced fungal resistance relative to control plants;

(iii) an exogenous nucleic acid capable of hybridizing under stringent conditions with a complementary sequence of any of the nucleic acids according to (i) or (ii); preferably encoding a CASAR protein; preferably wherein the nucleic acid molecule codes for a polypeptide which has essentially identical properties to the polypeptide described in SEQ ID NO: 3; preferably the encoded protein confers enhanced fungal resistance relative to control plants; and/or by (iv) an exogenous nucleic acid encoding the same CASAR protein as any of the nucleic acids of (i) to (iii) above, but differing from the nucleic acids of (i) to (iii) above due to the degeneracy of the genetic code.

Most preferably, the exogenous nucleic acid has at least 80%, at least 90%, at least 95%, at least 98%, at least 99% sequence identity, or even 100% sequence identity with SEQ ID NO: 2; or comprises an exogenous nucleic acid encoding a protein having at least 80%, at least 90%, at least 95%, at least 98%, at least 99% sequence identity, or even 100% sequence identity with SEQ ID NO: 3.

A preferred embodiment is a transgenic plant, transgenic plant part, or transgenic plant cell overexpressing an exogenous CASAR protein. Preferably, the CASAR protein overexpressed in the plant, plant part or plant cell is encoded by (i) an exogenous nucleic acid having at least 60% identity with SEQ ID NO: 2 or a functional fragment thereof, an orthologue or a paralogue thereof, or a splice variant thereof; or by (ii) an exogenous nucleic acid encoding a protein having at least 60% identity with SEQ ID NO: 3, a functional fragment thereof, an orthologue or a paralogue thereof; preferably the encoded protein confers enhanced fungal resistance relative to control plants;

(iii) an exogenous nucleic acid capable of hybridizing under stringent conditions with a complementary sequence of any of the nucleic acids according to (i) or (ii); preferably encoding a CASAR protein; preferably wherein the nucleic acid molecule codes for a polypeptide which has essentially identical properties to the polypeptide described in SEQ ID NO: 3; preferably the encoded protein confers enhanced fungal resistance relative to control plants; and/or by (iv) an exogenous nucleic acid encoding the same CASAR protein as any of the nucleic acids of (i) to (iii) above, but differing from the nucleic acids of (i) to (iii) above due to the degeneracy of the genetic code.

Most preferably, the exogenous nucleic acid has at least 80%, at least 90%, at least 95%, at least 98%, at least 99% sequence identity, or even 100% sequence identity with SEQ ID NO: 2; or comprises an exogenous nucleic acid encoding a protein having at least 95%, at least 98%, at least 99% sequence identity, or even 100% sequence identity with SEQ ID NO: 3.

In preferred embodiments, the protein amount of a CASAR protein in the transgenic plant is increased by at least 10%, at least 20%, at least 30%, at least 40%, at least 50%, at least 60%, at least 70%, at least 80%, at least 90%, or at least 95% or more in comparison to a wild type plant that is not transformed with the CASAR nucleic acid.

More preferably, the transgenic plant, transgenic plant part, or transgenic plant cell according to the present invention has been obtained by transformation with a recombinant vector described herein.

Suitable methods for transforming or transfecting host cells including plant cells are well known in the art of plant biotechnology. Any method may be used to transform the recombinant expression vector into plant cells to yield the transgenic plants of the invention. General methods for transforming dicotyledonous plants are disclosed, for example, in U.S. Pat. Nos. 4,940,838; 5,464,763, and the like. Methods for transforming specific dicotyledonous plants, for example, cotton, are set forth in U.S. Pat. Nos. 5,004,863; 5,159,135; and 5,846,797. Soy transformation methods are set forth in U.S. Pat. Nos. 4,992,375; 5,416,011; 5,569,834; 5,824,877; 6,384,301 and in EP 0301749B1 may be used. Transformation methods may include direct and indirect methods of transformation. Suitable direct methods include polyethylene glycol induced DNA uptake, liposome-mediated transformation (U.S. Pat. No. 4,536,475), biolistic methods using the gene gun (Fromm M E et al., Bio/Technology. 8(9):833-9, 1990; Gordon-Kamm et al. Plant Cell 2:603, 1990), electroporation, incubation of dry embryos in DNA-comprising solution, and microinjection. In the case of these direct transformation methods, the plasmids used need not meet any particular requirements. Simple plasmids, such as those of the pUC series, pBR322, M13mp series, pACYC184 and the like can be used. If intact plants are to be regenerated from the transformed cells, an additional selectable marker gene is preferably located on the plasmid. The direct transformation techniques are equally suitable for dicotyledonous and monocotyledonous plants.

Transformation can also be carried out by bacterial infection by means of *Agrobacterium* (for example EP 0 116 718), viral infection by means of viral vectors (EP 0 067 553; U.S. Pat. No. 4,407,956; WO 95/34668; WO 93/03161) or by means of pollen (EP 0 270 356; WO 85/01856; U.S. Pat. No. 4,684,611). *Agrobacterium* based transformation techniques (especially for dicotyledonous plants) are well known in the art. The *Agrobacterium* strain (e.g., *Agrobacterium tumefaciens* or *Agrobacterium rhizogenes*) comprises a plasmid (Ti or Ri plasmid) and a T-DNA element which is transferred to the plant following infection with *Agrobacterium*. The T-DNA (transferred DNA) is integrated into the genome of the plant cell. The T-DNA may be localized on the Ri- or Ti-plasmid or is separately comprised in a so-called binary vector. Methods for the *Agrobacterium*-mediated transformation are described, for example, in Horsch R B et al. (1985) Science 225:1229. The *Agrobacterium*-mediated transformation is best suited to dicotyledonous plants but has also been adapted to monocotyledonous plants. The transformation of plants by Agrobacteria is described in, for example, White F F, Vectors for Gene Transfer in Higher Plants, Transgenic Plants, Vol. 1, Engineering and Utilization, edited by S. D. Kung and R. Wu, Academic Press, 1993, pp. 15-38; Jenes B et al. Techniques for Gene Transfer, Transgenic Plants, Vol. 1, Engineering and Utilization, edited by S. D. Kung and R. Wu, Academic Press, 1993, pp. 128-143; Potrykus (1991) Annu Rev Plant Physiol Plant Molec Biol 42:205-225. Transformation may result in transient or stable transformation and expression. Although a nucleotide sequence of the present invention can be inserted into any plant and plant cell falling within these broad classes, it is particularly useful in crop plant cells.

The genetically modified plant cells can be regenerated via all methods with which the skilled worker is familiar. Suitable methods can be found in the abovementioned publications by S. D. Kung and R. Wu, Potrykus or Höfgen and Willmitzer.

After transformation, plant cells or cell groupings may be selected for the presence of one or more markers which are encoded by plant-expressible genes co-transferred with the gene of interest, following which the transformed material is regenerated into a whole plant. To select transformed plants, the plant material obtained in the transformation is, as a rule, subjected to selective conditions so that transformed plants can be distinguished from untransformed plants. For example, the seeds obtained in the above-described manner can be planted and, after an initial growing period, subjected to a suitable selection by spraying. A further possibility consists in growing the seeds, if appropriate after sterilization, on agar plates using a suitable selection agent so that only the transformed seeds can grow into plants. Alternatively, the transformed plants are screened for the presence of a selectable marker such as the ones described above. The transformed plants may also be directly selected by screening for the presence of the CASAR nucleic acid.

Following DNA transfer and regeneration, putatively transformed plants may also be evaluated, for instance using Southern analysis, for the presence of the gene of interest, copy number and/or genomic organisation. Alternatively or additionally, expression levels of the newly introduced DNA may be monitored using Northern and/or Western analysis, both techniques being well known to persons having ordinary skill in the art.

The generated transformed plants may be propagated by a variety of means, such as by clonal propagation or classical breeding techniques. For example, a first generation (or T1) transformed plant may be selfed and homozygous second-generation (or T2) transformants selected, and the T2 plants may then further be propagated through classical breeding techniques. The generated transformed organisms may take a variety of forms. For example, they may be chimeras of transformed cells and non-transformed cells; clonal transformants (e.g., all cells transformed to contain the expression cassette); grafts of transformed and untransformed tissues (e.g., in plants, a transformed rootstock grafted to an untransformed scion).

Preferably, constructs or vectors or expression cassettes are not present in the genome of the original plant or are present in the genome of the transgenic plant not at their natural locus of the genome of the original plant.

Preferably, the transgenic plant of the present invention or the plant obtained by the method of the present invention has increased resistance against fungal pathogens, preferably rust pathogens (i.e., fungal pathogens of the order Pucciniales), preferably against fungal pathogens of the family Phakopsoraceae, more preferably against fungal pathogens of the genus *Phakopsora*, most preferably against *Phakopsora pachyrhizi* and *Phakopsora meibomiae*, also known as soybean rust. Preferably, resistance against *Phakopsora pachyrhizi* and/or *Phakopsora meibomiae* is increased.

Preferably, the plant, plant part, or plant cell is a plant or derived from a plant selected from the group consisting of beans, soya, pea, clover, kudzu, lucerne, lentils, lupins, vetches, groundnut, rice, wheat, barley, *Arabidopsis*, lentil, banana, canola, cotton, potato, corn, sugar cane, alfalfa, and sugar beet.

In one embodiment of the present invention the plant is selected from the group consisting of beans, soya, pea, clover, kudzu, lucerne, lentils, lupins, vetches, and/or groundnut. Preferably, the plant is a legume, comprising plants of the genus *Phaseolus* (comprising French bean, dwarf bean, climbing bean (*Phaseolus vulgaris*), Lima bean (*Phaseolus lunatus* L.), Tepary bean (*Phaseolus acutifolius* A. Gray), runner bean (*Phaseolus coccineus*)); the genus

*Glycine* (comprising *Glycine soja*, soybeans (*Glycine max* (L.) Merill)); pea (*Pisum*) (comprising shelling peas (*Pisum sativum* L. convar. *sativum*), also called smooth or round-seeded peas; marrowfat pea (*Pisum sativum* L. convar. *medullare* Alef. emend. C.O. Lehm), sugar pea (*Pisum sativum* L. convar. *axiphium* Alef emend. C.O. Lehm), also called snow pea, edible-podded pea or mangetout, (*Pisum granda sneida* L. convar. *sneidulo* p. *shneiderium*)); peanut (*Arachis hypogaea*), clover (*Trifolium* spec.), medick (*Medicago*), kudzu vine (*Pueraria lobata*), common lucerne, alfalfa (*M. sativa* L.), chickpea (*Cicer*), lentils (Lens) (*Lens culinaris* Medik.), lupins (*Lupinus*); vetches (*Vicia*), field bean, broad bean (*Vicia faba*), vetchling (*Lathyrus*) (comprising chickling pea (*Lathyrus sativus*), heath pea (*Lathyrus tuberosus*)); genus *Vigna* (comprising moth bean (*Vigna aconitifolia* (Jacq.) Maréchal), adzuki bean (*Vigna angularis* (Willd.) Ohwi & H. Ohashi), urd bean (*Vigna mungo* (L.) Hepper), mung bean (*Vigna radiata* (L.) R. Wilczek), bambara groundnut (*Vigna subterrane* (L.) Verdc.), rice bean (*Vigna umbellata* (Thunb.) Ohwi & H. Ohashi), *Vigna vexillata* (L.) A. Rich., *Vigna unguiculata* (L.) Walp., in the three subspecies asparagus bean, cowpea, catjang bean)); pigeonpea (*Cajanus cajan* (L.) Millsp.), the genus *Macrotyloma* (comprising geocarpa groundnut (*Macrotyloma geocarpum* (Harms) Maréchal & Baudet), horse bean (*Macrotyloma uniflorum* (Lam.) Verdc.); goa bean (*Psophocarpus tetragonolobus* (L.) DC.), African yam bean (*Sphenostylis stenocarpa* (Hochst. ex A. Rich.) Harms), Egyptian black bean, *dolichos* bean, *lablab* bean (*Lablab purpureus* (L.) Sweet), yam bean (*Pachyrhizus*), guar bean (*Cyamopsis tetragonolobus* (L.) Taub.); and/or the genus *Canavalia* (comprising jack bean (*Canavalia ensiformis* (L.) DC.), sword bean (*Canavalia gladiata* (Jacq.) DC.).

Further preferred is a plant selected from the group consisting of beans, soya, pea, clover, kudzu, lucerne, lentils, lupins, vetches, and groundnut. Most preferably, the plant, plant part, or plant cell is or is derived from soy.

Preferably, the transgenic plant of the present invention or the plant obtained by the method of the present invention is a soybean plant and has increased resistance against fungal pathogens of the order Pucciniales (rust), preferably, of the family Phakopsoraceae, more preferably against fungal pathogens of the genus *Phakopsora*, most preferably against *Phakopsora pachyrhizi* and *Phakopsora meibomiae*, also known as soybean rust. Preferably, resistance against *Phakopsora pachyrhizi* and/or *Phakopsora meibomiae* is increased.

Methods for the Production of Transgenic Plants

One embodiment according to the present invention provides a method for producing a transgenic plant, a transgenic plant part, or a transgenic plant cell resistant to a fungal pathogen, preferably of the family Phakopsoraceae, for example soybean rust, wherein the recombinant nucleic acid used to generate a transgenic plant comprises a promoter that is functional in the plant cell, operably linked to a CASAR nucleic acid, which is preferably SEQ ID NO: 2, 1, 5-12, 13, 15, 17, 19, 21, 23, 25, or 27, and a terminator regulatory sequence.

In one embodiment, the present invention refers to a method for the production of a transgenic plant, transgenic plant part, or transgenic plant cell having increased fungal resistance, comprising (a) introducing a recombinant vector construct according to the present invention into a plant, a plant part or a plant cell and (b) generating a transgenic plant from the plant, plant part or plant cell.

Preferably, the method for the production of the transgenic plant, transgenic plant part, or transgenic plant cell further comprises the step (c) expressing the CASAR protein, preferably encoded by
  (i) an exogenous nucleic acid having at least 60% identity with SEQ ID NO: 2, 1, 5-12, 13, 15, 17, 19, 21, 23, 25, or 27, a functional fragment thereof, an orthologue or a paralogue thereof, or a splice variant thereof;
  (ii) an exogenous nucleic acid encoding a protein having at least 60% identity with SEQ ID NO: 3, 14, 16, 18, 20, 22, 24, 26, or 28, or a functional fragment thereof, an orthologue or a paralogue thereof; preferably the encoded protein confers enhanced fungal resistance relative to control plants;
  (iii) an exogenous nucleic acid capable of hybridizing under stringent conditions with a complementary sequence of any of the nucleic acids according to (i) or (ii); preferably encoding a CASAR protein; preferably wherein the nucleic acid molecule codes for a polypeptide which has essentially identical properties to the polypeptide described in SEQ ID NO: 3; preferably the encoded protein confers enhanced fungal resistance relative to control plants; and/or by
  (iv) an exogenous nucleic acid encoding the same CASAR protein as any of the nucleic acids of (i) to (iii) above, but differing from the nucleic acids of (i) to (iii) above due to the degeneracy of the genetic code.

Preferably, said introducing and expressing does not comprise an essentially biological process.

More preferably, the method for the production of the transgenic plant, transgenic plant part, or transgenic plant cell further comprises the step (c) expressing the CASAR protein, preferably encoded by
  (i) an exogenous nucleic acid having at least 60% identity with SEQ ID NO: 2, a functional fragment thereof, an orthologue or a paralogue thereof, or a splice variant thereof;
  (ii) an exogenous nucleic acid encoding a protein having at least 60% identity with SEQ ID NO: 3, or a functional fragment thereof, an orthologue or a paralogue thereof; preferably the encoded protein confers enhanced fungal resistance relative to control plants;
  (iii) an exogenous nucleic acid capable of hybridizing under stringent conditions with a complementary sequence of any of the nucleic acids according to (i) or (ii); preferably encoding a CASAR protein; preferably wherein the nucleic acid molecule codes for a polypeptide which has essentially identical properties to the polypeptide described in SEQ ID NO: 3; preferably the encoded protein confers enhanced fungal resistance relative to control plants; and/or by
  (iv) an exogenous nucleic acid encoding the same CASAR protein as any of the nucleic acids of (i) to (iii) above, but differing from the nucleic acids of (i) to (iii) above due to the degeneracy of the genetic code.

Preferably, the method for the production of the transgenic plant, transgenic plant part, or transgenic plant cell further comprises the step of selecting a transgenic plant expressing (i) an exogenous nucleic acid having at least 60% identity, preferably at least 70% sequence identity, at least 80%, at least 90%, at least 95%, at least 98%, at least 99% sequence identity, or even 100% sequence identity with SEQ ID NO: 2, 1, 5-12, 13, 15, 17, 19, 21, 23, 25, or 27, or a functional fragment thereof, or an orthologue or a paralogue thereof, or a splice variant thereof;

(ii) an exogenous nucleic acid coding for a protein having at least 60% identity, preferably at least 70% sequence identity, at least 80%, at least 90%, at least 95%, at least 98%, at least 99% sequence identity, or even 100% sequence identity with SEQ ID NO: 3, 14, 16, 18, 20, 22, 24, 26, or 28, a functional fragment thereof, an orthologue or a paralogue thereof; preferably the encoded protein confers enhanced fungal resistance relative to control plants;

(iii) an exogenous nucleic acid capable of hybridizing under stringent conditions with a complementary sequence of any of the nucleic acids according to (i) or (ii); preferably encoding a CASAR protein; preferably wherein the nucleic acid molecule codes for a polypeptide which has essentially identical properties to the polypeptide described in SEQ ID NO: 3; preferably the encoded protein confers enhanced fungal resistance relative to control plants; and/or (iv) an exogenous nucleic acid encoding the same CASAR polypeptide as any of the nucleic acids of (i) to (iii) above, but differing from the nucleic acids of (i) to (iii) above due to the degeneracy of the genetic code.

Preferably, the method for the production of the transgenic plant, transgenic plant part, or transgenic plant cell additionally comprises the step of harvesting the seeds of the transgenic plant and planting the seeds and growing the seeds to plants, wherein the grown plant(s) comprises (i) the exogenous nucleic acid having at least 60% identity with SEQ ID NO: 2, 1, 5-12, 13, 15, 17, 19, 21, 23, 25, or 27, a functional fragment thereof, an orthologue or a paralogue thereof, or a splice variant thereof;

(ii) the exogenous nucleic acid encoding a protein having at least 60% identity with SEQ ID NO: 3, 14, 16, 18, 20, 22, 24, 26, or 28, or a functional fragment thereof, an orthologue or a paralogue thereof; preferably the encoded protein confers enhanced fungal resistance relative to control plants;

(iii) the exogenous nucleic acid capable of hybridizing under stringent conditions with a complementary sequence of any of the nucleic acids according to (i) or (ii); preferably encoding a CASAR protein; preferably wherein the nucleic acid molecule codes for a polypeptide which has essentially identical properties to the polypeptide described in SEQ ID NO: 3; preferably the encoded protein confers enhanced fungal resistance relative to control plants; and/or (iv) the exogenous nucleic acid encoding the same CASAR protein as any of the nucleic acids of (i) to (iii) above, but differing from the nucleic acids of (i) to (iii) above due to the degeneracy of the genetic code;

preferably, the step of harvesting the seeds of the transgenic plant and planting the seeds and growing the seeds to plants, wherein the grown plant(s) comprises (i) the exogenous nucleic acid having at least 60% identity with SEQ ID NO: 2, 1, 5-12, 13, 15, 17, 19, 21, 23, 25, or 27, a functional fragment thereof, an orthologue or a paralogue thereof, or a splice variant thereof;

(ii) the exogenous nucleic acid encoding a protein having at least 60% identity with SEQ ID NO: 3, 14, 16, 18, 20, 22, 24, 26, or 28, or a functional fragment thereof, an orthologue or a paralogue thereof; preferably the encoded protein confers enhanced fungal resistance relative to control plants;

(iii) the exogenous nucleic acid capable of hybridizing under stringent conditions with a complementary sequence of any of the nucleic acids according to (i) or (ii); preferably encoding a CASAR protein; preferably wherein the nucleic acid molecule codes for a polypeptide which has essentially identical properties to the polypeptide described in SEQ ID NO: 3; preferably the encoded protein confers enhanced fungal resistance relative to control plants; and/or (iv) the exogenous nucleic acid encoding the same CASAR protein as any of the nucleic acids of (i) to (iii) above, but differing from the nucleic acids of (i) to (iii) above due to the degeneracy of the genetic code;

is repeated more than one time, preferably, 1, 2, 3, 4, 5, 6, 7, 8, 9, 10, 15, 20, 25, 30, 35, 40, 45, or 50 times.

The transgenic plants may be selected by known methods as described above (e.g., by screening for the presence of one or more markers which are encoded by plant-expressible genes co-transferred with the CASAR gene or by directly screening for the CASAR nucleic acid).

Furthermore, the use of the exogenous CASAR nucleic acid or the recombinant vector construct comprising the CASAR nucleic acid for the transformation of a plant, plant part, or plant cell to provide a fungal resistant plant, plant part, or plant cell is provided.

Harvestable Parts and Products

Harvestable parts of the transgenic plant according to the present invention are part of the invention. Preferably, the harvestable parts comprise the CASAR nucleic acid or CASAR protein. The harvestable parts may be seeds, roots, leaves and/or flowers comprising the CASAR nucleic acid or CASAR protein or parts thereof. Preferred parts of soy plants are soy beans comprising the CASAR nucleic acid or CASAR protein.

Products derived from a transgenic plant according to the present invention, parts thereof or harvestable parts thereof are part of the invention. A preferred product is meal or oil, preferably, soybean meal or soybean oil. Preferably, the soybean meal and/or oil comprises the CASAR nucleic acid or CASAR protein.

Preferably the harvestable parts of the transgenic plant according to the present invention or the products derived from a transgenic plant comprise an exogenous nucleic acid molecule consisting of or comprising a nucleic acid selected from the group consisting of:

(i) an exogenous nucleic acid having in increasing order of preference at least at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to the nucleic acid sequence represented by SEQ ID NO: 2, 1, 5-12, 13, 15, 17, 19, 21, 23, 25, or 27, or a functional fragment, derivative, orthologue, or paralogue thereof, or a splice variant thereof;

(ii) an exogenous nucleic acid encoding a CASAR protein comprising an amino acid sequence having in increasing order of preference at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to the amino acid sequence represented by SEQ ID NO: 3, 14, 16, 18, 20, 22, 24, 26, or 28, or a functional fragment, derivative, orthologue, or paralogue thereof; preferably the CASAR protein has essentially the same biological activity as a CASAR protein encoded by SEQ ID NO: 2 or 1; preferably the CASAR protein confers enhanced fungal, preferably rust, resistance relative to control plants;

(iii) an exogenous nucleic acid molecule which hybridizes with a complementary sequence of any of the nucleic acid molecules of (i) or (ii) under high stringency hybridization conditions; preferably encoding a CASAR protein; preferably wherein the nucleic acid molecule codes for a polypeptide which has essentially identical properties to the polypeptide described in SEQ ID NO: 3; preferably the encoded protein confers enhanced fungal, preferably rust, resistance relative to control plants; and (iv) an exogenous nucleic acid encoding the same CASAR protein as the CASAR nucleic acids of (i) to (iii) above, but differing from the CASAR nucleic acids of (i) to (iii) above due to the degeneracy of the genetic code, or wherein the harvestable part of the transgenic plant or the product derived from the transgenic plant comprises a CASAR protein encoded by any one of the CASAR nucleic acids of (i) to (iv).

Methods for Manufacturing a Product

The plants, plant parts or plant cells of the invention or obtainable by the methods of invention can be used for the manufacturing of a harvestable part or product.

In one embodiment the method for the production of a product comprises a) growing the plants of the invention or obtainable by the methods of invention and b) producing said product from or by the plants of the invention and/or parts, e.g. seeds, of these plants.

In a further embodiment the method comprises the steps a) growing the plants of the invention, b) removing the harvestable parts as defined above from the plants and c) producing said product from or by the harvestable parts of the invention.

Preferably the products obtained by said method comprises an exogenous nucleic acid molecule consisting of or comprising a nucleic acid selected from the group consisting of:

(i) an exogenous nucleic acid having in increasing order of preference at least at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to the nucleic acid sequence represented by SEQ ID NO: 2, 1, 5-12, 13, 15, 17, 19, 21, 23, 25, or 27, or a functional fragment, derivative, orthologue, or paralogue thereof, or a splice variant thereof;

(ii) an exogenous nucleic acid encoding a CASAR protein comprising an amino acid sequence having in increasing order of preference at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to the amino acid sequence represented by SEQ ID NO: 3, 14, 16, 18, 20, 22, 24, 26, or 28, or a functional fragment, derivative, orthologue, or paralogue thereof; preferably the CASAR protein has essentially the same biological activity as a CASAR protein encoded by SEQ ID NO: 2 or 1; preferably the CASAR protein confers enhanced fungal, preferably rust, resistance relative to control plants;

(iii) an exogenous nucleic acid molecule which hybridizes with a complementary sequence of any of the nucleic acid molecules of (i) or (ii) under high stringency hybridization conditions; preferably encoding a CASAR protein; preferably wherein the nucleic acid molecule codes for a polypeptide which has essentially identical properties to the polypeptide described in SEQ ID NO: 3; preferably the encoded protein confers enhanced fungal, preferably rust, resistance relative to control plants; and (iv) an exogenous nucleic acid encoding the same CASAR protein as the CASAR nucleic acids of (i) to (iii) above, but differing from the CASAR nucleic acids of (i) to (iii) above due to the degeneracy of the genetic code, or wherein the product obtained by said method comprises a CASAR protein encoded by any one of the CASAR nucleic acids of (i) to (iv).

The product may be produced at the site where the plant has been grown, the plants and/or parts thereof may be removed from the site where the plants have been grown to produce the product. Typically, the plant is grown, the desired harvestable parts are removed from the plant, if feasible in repeated cycles, and the product made from the harvestable parts of the plant. The step of growing the plant may be performed only once each time the methods of the invention is performed, while allowing repeated times the steps of product production e.g. by repeated removal of harvestable parts of the plants of the invention and if necessary further processing of these parts to arrive at the product. It is also possible that the step of growing the plants of the invention is repeated and plants or harvestable parts are stored until the production of the product is then performed once for the accumulated plants or plant parts. Also, the steps of growing the plants and producing the product may be performed with an overlap in time, even simultaneously to a large extend or sequentially. Generally the plants are grown for some time before the product is produced.

In one embodiment the products produced by said methods of the invention are plant products such as, but not limited to, a foodstuff, feedstuff, a food supplement, feed supplement, fiber, cosmetic and/or pharmaceutical. Foodstuffs are regarded as compositions used for nutrition and/or for supplementing nutrition. Animal feedstuffs and animal feed supplements, in particular, are regarded as foodstuffs.

In another embodiment the inventive methods for the production are used to make agricultural products such as, but not limited to, plant extracts, proteins, amino acids, carbohydrates, fats, oils, polymers, vitamins, and the like.

It is possible that a plant product consists of one or more agricultural products to a large extent.

Methods for Breeding/Methods for Plant Improvement/Methods Plant Variety Production The transgenic plants of the invention may be crossed with similar transgenic plants or with transgenic plants lacking the nucleic acids of the invention or with non-transgenic plants, using known methods of plant breeding, to prepare seeds. Further, the transgenic plant cells or plants of the present invention may comprise, and/or be crossed to another transgenic plant that comprises one or more exogenous nucleic acids, thus creating a "stack" of transgenes in the plant and/or its progeny. The seed is then planted to obtain a crossed fertile transgenic plant comprising the CASAR nucleic acid. The crossed fertile transgenic plant may have the particular expression cassette inherited through a female parent or through a male parent. The second plant may be an inbred plant. The crossed fertile transgenic may be a hybrid. Also included within the present invention are seeds of any of these crossed fertile transgenic plants. The seeds of this invention can be harvested from fertile transgenic plants and be used to grow progeny generations of transformed plants of this invention including hybrid plant lines comprising the exogenous nucleic acid.

Thus, one embodiment of the present invention is a method for breeding a fungal resistant plant comprising the steps of (a) crossing a transgenic plant described herein or a plant obtainable by a method described herein with a second plant;
(b) obtaining a seed or seeds resulting from the crossing step described in (a);
(c) planting said seed or seeds and growing the seed or seeds to plants; and
(d) selecting from said plants the plants expressing a CASAR protein, preferably encoded by
   (i) an exogenous nucleic acid having at least 60% identity with SEQ ID NO: 2, 1, 5-12, 13, 15, 17, 19, 21, 23, 25, or 27, a functional fragment thereof, an orthologue or a paralogue thereof, or a splice variant thereof;
   (ii) an exogenous nucleic acid encoding a protein having at least 60% identity with SEQ ID NO: 3, 14, 16, 18, 20, 22, 24, 26, or 28, or a functional fragment thereof, an orthologue or a paralogue thereof; preferably the encoded protein confers enhanced fungal resistance relative to control plants;
   (iii) an exogenous nucleic acid capable of hybridizing under stringent conditions with a complementary sequence of any of the nucleic acids according to (i) or (ii); preferably encoding a CASAR protein; preferably wherein the nucleic acid molecule codes for a polypeptide which has essentially identical properties to the polypeptide described in SEQ ID NO: 3; preferably the encoded protein confers enhanced fungal resistance relative to control plants; and/or by
   (iv) an exogenous nucleic acid encoding the same CASAR protein as any of the nucleic acids of (i) to (iii) above, but differing from the nucleic acids of (i) to (iii) above due to the degeneracy of the genetic code.

Another preferred embodiment is a method for plant improvement comprising (a) obtaining a transgenic plant by any of the methods of the present invention;
(b) combining within one plant cell the genetic material of at least one plant cell of the plant of (a) with the genetic material of at least one cell differing in one or more gene from the plant cells of the plants of (a) or crossing the transgenic plant of (a) with a second plant;
(c) obtaining seed from at least one plant generated from the one plant cell of (b) or the plant of the cross of step (b);
(d) planting said seeds and growing the seeds to plants; and
(e) selecting from said plants, plants expressing the nucleic acid encoding the CASAR protein; and optionally
(f) producing propagation material from the plants expressing the nucleic acid encoding the CASAR protein.

The transgenic plants may be selected by known methods as described above (e.g., by screening for the presence of one or more markers which are encoded by plant-expressible genes co-transferred with the CASAR gene or screening for the CASAR nucleic acid itself).

According to the present invention, the introduced CASAR nucleic acid may be maintained in the plant cell stably if it is incorporated into a non-chromosomal autonomous replicon or integrated into the plant chromosomes. Whether present in an extra-chromosomal nonreplicating or replicating vector construct or a vector construct that is integrated into a chromosome, the exogenous CASAR nucleic acid preferably resides in a plant expression cassette. A plant expression cassette preferably contains regulatory sequences capable of driving gene expression in plant cells that are functional linked so that each sequence can fulfill its function, for example, termination of transcription by polyadenylation signals. Preferred polyadenylation signals are those originating from *Agrobacterium tumefaciens* t-DNA such as the gene 3 known as octopine synthase of the Ti-plasmid pTiACH5 (Gielen et al., 1984, EMBO J. 3:835) or functional equivalents thereof, but also all other terminators functionally active in plants are suitable. As plant gene expression is very often not limited on transcriptional levels, a plant expression cassette preferably contains other functional linked sequences like translational enhancers such as the overdrive-sequence containing the 5'-untranslated leader sequence from tobacco mosaic virus increasing the polypeptide per RNA ratio (Gallie et al., 1987, Nucl. Acids Research 15:8693-8711). Examples of plant expression vectors include those detailed in: Becker, D. et al., 1992, New plant binary vectors with selectable markers located proximal to the left border, Plant Mol. Biol. 20:1195-1197; Bevan, M. W., 1984, Binary *Agrobacterium* vectors for plant transformation, Nucl. Acid. Res. 12:8711-8721; and Vectors for Gene Transfer in Higher Plants; in: Transgenic Plants, Vol. 1, Engineering and Utilization, eds.: Kung and R. Wu, Academic Press, 1993, S. 15-38.

EXAMPLES

The following examples are not intended to limit the scope of the claims to the invention, but are rather intended to be exemplary of certain embodiments. Any variations in the exemplified methods that occur to the skilled artisan are intended to fall within the scope of the present invention.

Example 1: General Methods

The chemical synthesis of oligonucleotides can be affected, for example, in the known fashion using the phosphoamidite method (Voet, Voet, 2nd Edition, Wiley Press New York, pages 896-897). The cloning steps carried out for the purposes of the present invention such as, for example, restriction cleavages, agarose gel electrophoresis, purification of DNA fragments, transfer of nucleic acids to nitrocellulose and nylon membranes, linking DNA fragments, transformation of *E. coli* cells, bacterial cultures, phage multiplication and sequence analysis of recombinant DNA, are carried out as described by Sambrook et al. Cold Spring Harbor Laboratory Press (1989), ISBN 0-87969-309-6. The sequencing of recombinant DNA molecules is carried out with an MWG-Licor laser fluorescence DNA sequencer following the method of Sanger (Sanger et al., Proc. Natl. Acad. Sci. USA 74, 5463 (1977)).

Example 2: Cloning of Overexpression Vector Constructs

The CASAR cDNA (as shown in SEQ ID NO: 1) was synthesized in a way that an BamHI restriction site is located in front of the start-ATG and an PstI restriction site downstream of the stop-codon. The synthesized cDNA was digested using the restriction enzyme PstI (NEB Biolabs), the sticky end of the PstI site was blunted using Mung Bean Nuclease according to manufactures manual (NEB Biolabs). The blunted fragment was digested using the restriction enzyme BamHI and ligated in a HindIII digested Gateway pENTRY-B vector (Invitrogen, Life Technologies, Carlsbad, Calif., USA). The sticky end of the HindIII site was blunted using Mung Bean Nuclease according to manufactures manual (NEB Biolabs) and the blunted vector was digested with BamHI before the ligation.

Figure 2:
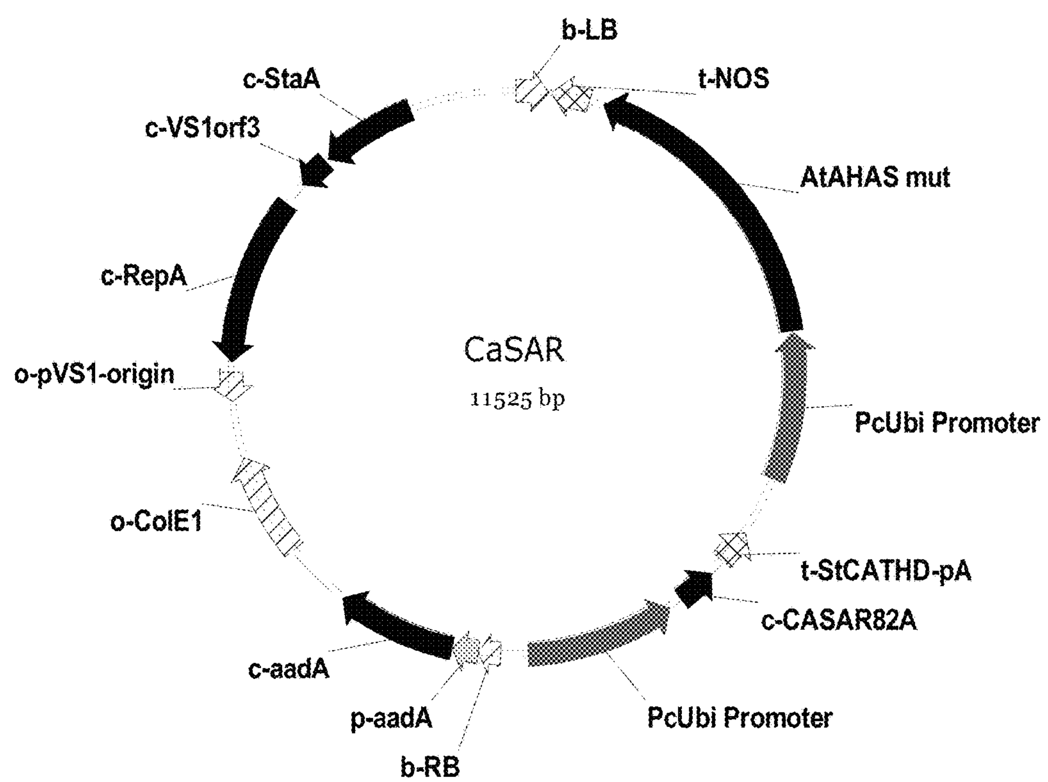
FIG. 2 shows the schematic illustration of the plant transformation vector harboring the CASAR cDNA under control of the parsley ubiquitine promoter.

To obtain the binary plant transformation vector, a triple LR reaction (Gateway system, Invitrogen, Life Technologies, Carlsbad, Calif., USA) was performed according to manufacturer's protocol by using a pENTRY-A vector containing a parsley ubiquitine promoter, the above described pENTRY-B vector containing the CASAR gene and a pENTRY-C vector containing the terminator of the cathepsin D inhibitor gene from *Solanum tuberosum*. As target a binary pDEST vector was used which is composed of: (1) a Spectinomycin/Streptomycin resistance cassette for bacterial selection (2) a pVS1 origin for replication in Agrobacteria (3) a colE-1 origin of replication for stable maintenance in *E. coli* and (4) between the right and left border an AHAS selection under control of a pcUbi-promoter (FIG. 2). The recombination reaction was transformed into *E. coli* (DH5alpha), mini-prepped and screened by specific restriction digestions. A positive clone from each vector construct was sequenced and submitted for soy transformation.

The soybean-expression optimized CASAR cDNA (as shown in SEQ ID NO: 2) was synthesized in a way that an NcoI restriction site is located in front of the start-ATG and an AscI restriction site downstream of the stop-codon. The synthesized cDNAs were digested using the restriction enzymes NcoI and AscI (NEB Biolabs) and ligated in a NcoI/AscI digested Gateway pENTRY-B vector (Invitrogen, Life Technologies, Carlsbad, Calif., USA) in a way that the full-length fragment is located in sense direction between the "rust induced mesophyll specific promoter 820" (mesophyll specific promoter, expression induced by *Phakopsora pachyrhizi*, SEQ ID NO: 4) and the terminator of the cathepsin D inhibitor gene from *Solanum tuberosum* (t-StCATHD-pA).

Figure 3:
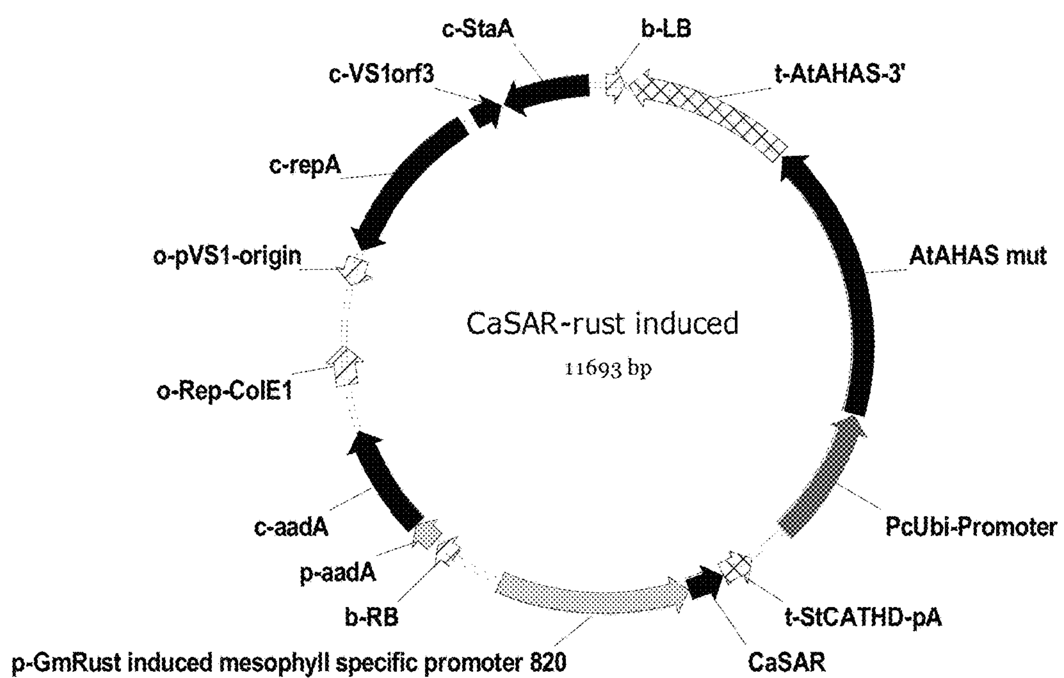
FIG. 3 shows the schematic illustration of the plant transformation vector harboring the CASAR cDNA under the control of the pathogen induced "rust induced mesophyll specific promoter 820".

To obtain the binary plant transformation vector, a triple LR reaction (Gateway system, Invitrogen, Life Technologies, Carlsbad, Calif., USA) was performed according to manufacturers protocol by using an empty pENTRY-A vector, the promoter::cDNA::terminator in a pENTRY-B vector, and an empty pENTRY-C vector. As target a binary pDEST vector was used which is composed of: (1) a Spectinomycin/Streptomycin resistance cassette for bacterial selection (2) a pVS1 origin for replication in Agrobacteria (3) a colE-1 origin of replication for stable maintenance in *E. coli* and (4) between the right and left border an AHAS selection under control of a pcUbi-promoter (FIG. 3). The recombination reaction was transformed into *E. coli* (DH5alpha), mini-prepped and screened by specific restriction digestions. A positive clone from each vector construct was sequenced and submitted soy transformation.

Example 3: Soy Transformation

The expression vector constructs (see example 2) were transformed into soy.

3.1 Sterilization and Germination of Soy Seeds

Virtually any seed of any soy variety can be employed in the method of the invention. A variety of soybean cultivar (including Jack, Williams 82, Jake, Stoddard and Resnik) is appropriate for soy transformation. Soy seeds were sterilized in a chamber with a chlorine gas produced by adding 3.5 ml 12N HCl drop wise into 100 ml bleach (5.25% sodium hypochlorite) in a desiccator with a tightly fitting lid. After 24 to 48 hours in the chamber, seeds were removed and approximately 18 to 20 seeds were plated on solid GM medium with or without 5 μM 6-benzyl-aminopurine (BAP) in 100 mm Petri dishes. Seedlings without BAP are more elongated and roots develop, especially secondary and lateral root formation. BAP strengthens the seedling by forming a shorter and stockier seedling.

Seven-day-old seedlings grown in the light (>100 μEinstein/m$^2$s) at 25° C. were used for explant material for the three-explant types. At this time, the seed coat was split, and the epicotyl with the unifoliate leaves have grown to, at minimum, the length of the cotyledons. The epicotyl should be at least 0.5 cm to avoid the cotyledonary-node tissue (since soycultivars and seed lots may vary in the developmental time a description of the germination stage is more accurate than a specific germination time).

For inoculation of entire seedlings, see Method A (example 3.3.1 and 3.3.2) or leaf explants, see Method B (example 3.3.3).

For method C (see example 3.3.4), the hypocotyl and one and a half or part of both cotyledons were removed from each seedling. The seedlings were then placed on propagation media for 2 to 4 weeks. The seedlings produce several branched shoots to obtain explants from. The majority of the explants originated from the plantlet growing from the apical bud. These explants were preferably used as target tissue.

3.2—Growth and Preparation of *Agrobacterium* Culture

*Agrobacterium* cultures were prepared by streaking *Agrobacterium* (e.g., *A. tumefaciens* or *A. rhizogenes*) carrying the desired binary vector (e.g. H. Klee. R. Horsch and S. Rogers 1987 *Agrobacterium*-Mediated Plant Transformation and its further Applications to Plant Biology; Annual Review of Plant Physiology Vol. 38: 467-486) onto solid YEP growth medium (YEP media: 10 g yeast extract, 10 g Bacto Peptone, 5 g NaCl, Adjust pH to 7.0, and bring final volume to 1 liter with H2O, for YEP agar plates add 20 g Agar, autoclave) and incubating at 25° C. until colonies appeared (about 2 days). Depending on the selectable marker genes present on the Ti or Ri plasmid, the binary vector, and the bacterial chromosomes, different selection compounds were be used for *A. tumefaciens* and *A. rhizogenes* selection in the YEP solid and liquid media. Various *Agrobacterium* strains can be used for the transformation method.

After approximately two days, a single colony (with a sterile toothpick) was picked and 50 ml of liquid YEP was inoculated with antibiotics and shaken at 175 rpm (25° C.) until an $OD_{600}$ between 0.8-1.0 is reached (approximately 2 d). Working glycerol stocks (15%) for transformation are prepared and one-ml of *Agrobacterium* stock aliquoted into 1.5 ml Eppendorf tubes then stored at −80° C.

The day before explant inoculation, 200 ml of YEP were inoculated with 5 μl to 3 ml of working *Agrobacterium* stock in a 500 ml Erlenmeyer flask. The flask was shaken overnight at 25° C. until the $OD_{600}$ was between 0.8 and 1.0. Before preparing the soy explants, the Agrobacteria were pelleted by centrifugation for 10 min at 5,500×g at 20° C. The pellet was resuspended in liquid CCM to the desired density ($OD_{600}$ 0.5-0.8) and placed at room temperature at least 30 min before use.

3.3—Explant Preparation and Co-Cultivation (Inoculation)

3.3.1 Method A: Explant Preparation on the Day of Transformation.

Seedlings at this time had elongated epicotyls from at least 0.5 cm but generally between 0.5 and 2 cm. Elongated epicotyls up to 4 cm in length had been successfully employed. Explants were then prepared with: i) with or without some roots, ii) with a partial, one or both cotyledons, all preformed leaves were removed including apical meristem, and the node located at the first set of leaves was injured with several cuts using a sharp scalpel.

This cutting at the node not only induced *Agrobacterium* infection but also distributed the axillary meristem cells and damaged pre-formed shoots. After wounding and preparation, the explants were set aside in a Petri dish and subsequently co-cultivated with the liquid CCM/*Agrobacterium* mixture for 30 minutes. The explants were then removed from the liquid medium and plated on top of a sterile filter paper on 15×100 mm Petri plates with solid co-cultivation medium. The wounded target tissues were placed such that they are in direct contact with the medium.

3.3.2 Modified Method A: Epicotyl Explant Preparation

Soyepicotyl segments prepared from 4 to 8 d old seedlings were used as explants for regeneration and transformation. Seeds of soya cv. L00106CN, 93-41131 and Jack were germinated in 1/10 MS salts or a similar composition medium with or without cytokinins for 4 to 8 d. Epicotyl explants were prepared by removing the cotyledonary node and stem node from the stem section. The epicotyl was cut into 2 to 5 segments. Especially preferred are segments attached to the primary or higher node comprising axillary meristematic tissue.

The explants were used for *Agrobacterium* infection. *Agrobacterium* AGL1 harboring a plasmid with the gene of interest (GOI) and the AHAS, bar or dsdA selectable marker gene was cultured in LB medium with appropriate antibiotics overnight, harvested and resuspended in a inoculation medium with acetosyringone. Freshly prepared epicotyl segments were soaked in the *Agrobacterium* suspension for 30 to 60 min and then the explants were blotted dry on sterile filter papers. The inoculated explants were then cultured on a co-culture medium with L-cysteine and TTD and other chemicals such as acetosyringone for increasing T-DNA delivery for 2 to 4 d. The infected epicotyl explants were then placed on a shoot induction medium with selection agents such as imazapyr (for AHAS gene), glufosinate (for bar gene), or D-serine (for dsdA gene). The regenerated shoots were sub-cultured on elongation medium with the selective agent.

For regeneration of transgenic plants the segments were then cultured on a medium with cytokinins such as BAP, TDZ and/or Kinetin for shoot induction. After 4 to 8 weeks, the cultured tissues were transferred to a medium with lower concentration of cytokinin for shoot elongation. Elongated shoots were transferred to a medium with auxin for rooting and plant development. Multiple shoots were regenerated.

Many stable transformed sectors showing strong cDNA expression were recovered. Soybean plants were regenerated from epicotyl explants. Efficient T-DNA delivery and stable transformed sectors were demonstrated.

3.3.3 Method B: Leaf Explants

For the preparation of the leaf explant the cotyledon was removed from the hypocotyl. The cotyledons were separated from one another and the epicotyl is removed. The primary leaves, which consist of the lamina, the petiole, and the stipules, were removed from the epicotyl by carefully cutting at the base of the stipules such that the axillary meristems were included on the explant. To wound the explant as well as to stimulate de novo shoot formation, any preformed shoots were removed and the area between the stipules was cut with a sharp scalpel 3 to 5 times.

The explants are either completely immersed or the wounded petiole end dipped into the *Agrobacterium* suspension immediately after explant preparation. After inoculation, the explants are blotted onto sterile filter paper to remove excess *Agrobacterium* culture and place explants with the wounded side in contact with a round 7 cm Whatman paper overlaying the solid CCM medium (see above). This filter paper prevents *A. tumefaciens* overgrowth on the soy-explants. Wrap five plates with Parafilm™ "M" (American National Can, Chicago, Ill., USA) and incubate for three to five days in the dark or light at 25° C.

3.3.4 Method C: Propagated Axillary Meristem

For the preparation of the propagated axillary meristem explant propagated 3-4 week-old plantlets were used. Axillary meristem explants can be pre-pared from the first to the fourth node. An average of three to four explants could be obtained from each seedling. The explants were prepared from plantlets by cutting 0.5 to 1.0 cm below the axillary node on the internode and removing the petiole and leaf from the explant. The tip where the axillary meristems lie was cut with a scalpel to induce de novo shoot growth and allow access of target cells to the *Agrobacterium*. Therefore, a 0.5 cm explant included the stem and a bud.

Once cut, the explants were immediately placed in the *Agrobacterium* suspension for 20 to 30 minutes. After inoculation, the explants were blotted onto sterile filter paper to remove excess *Agrobacterium* culture then placed almost completely immersed in solid CCM or on top of a round 7 cm filter paper overlaying the solid CCM, depending on the *Agrobacterium* strain. This filter paper prevents *Agrobacterium* overgrowth on the soy-explants. Plates were wrapped with Parafilm™"M" (American National Can, Chicago, Ill., USA) and incubated for two to three days in the dark at 25° C.

3.4—Shoot Induction

After 3 to 5 days co-cultivation in the dark at 25° C., the explants were rinsed in liquid SIM medium (for SIM, see Olhoft et al., A novel *Agrobacterium rhizogenes*-mediated transformation method of soy using primary-node explants from seedlings, In Vitro Cell. Dev. Biol.—Plant (2007) 43:536-549) or Modwash medium (1×B5 major salts, 1×B5 minor salts, 1×MSIII iron, 3% Sucrose, 1×B5 vitamins, 30 mM MES, 350 mg/L Timentin™ pH 5.6, WO 2005/121345) to remove excess *Agrobacterium* and blotted dry on sterile filter paper (to prevent damage especially on the lamina) before placing on the solid SIM medium. The approximately 5 explants (Method A) or 10 to 20 (Methods B and C) explants were placed such that the target tissue was in direct contact with the medium. During the first 2 weeks, the explants could be cultured with or without selective medium. Preferably, explants were transferred onto SIM without selection for one week.

For leaf explants (Method B), the explant should be placed into the medium such that it is perpendicular to the surface of the medium with the petiole imbedded into the medium and the lamina out of the medium.

For propagated axillary meristem (Method C), the explant was placed into the medium such that it was parallel to the surface of the medium (basipetal) with the explant partially embedded into the medium.

Wrap plates with Scotch 394 venting tape (3M, St. Paul, Minn., USA) were placed in a growth chamber for two weeks with a temperature averaging 25° C. under 18 h light/6 h dark cycle at 70-100 μE/m$^2$s. The explants remained on the SIM medium with or without selection until de novo shoot growth occurred at the target area (e.g., axillary meristems at the first node above the epicotyl). Transfers to fresh medium can occur during this time. Explants were transferred from the SIM with or without selection to SIM with selection after about one week. At this time, there was considerable de novo shoot development at the base of the petiole of the leaf explants in a variety of SIM (Method B), at the primary node for seedling explants (Method A), and at the axillary nodes of propagated explants (Method C).

Preferably, all shoots formed before transformation were removed up to 2 weeks after co-cultivation to stimulate new growth from the meristems. This helped to reduce chimerism in the primary transformant and increase amplification of transgenic meristematic cells. During this time the explant may or may not be cut into smaller pieces (i.e. detaching the node from the explant by cutting the epicotyl).

3.5—Shoot Elongation

After 2 to 4 weeks (or until a mass of shoots was formed) on SIM medium (preferably with selection), the explants were transferred to SEM medium (shoot elongation medium, see Olhoft et al., A novel *Agrobacterium rhizogenes*-mediated transformation method of soy using primary-node explants from seedlings, In Vitro Cell. Dev. Biol. Plant (2007) 43:536-549) that stimulates shoot elongation of the shoot primordia. This medium may or may not contain a selection compound.

After every 2 to 3 weeks, the explants were transferred to fresh SEM medium (preferably containing selection) after carefully removing dead tissue. The explants should hold together and not fragment into pieces and retain somewhat healthy. The explants were continued to be transferred until the explant dies or shoots elongate. Elongated shoots >3 cm were removed and placed into RM medium for about 1 week (Method A and B), or about 2 to 4 weeks depending on the cultivar (Method C) at which time roots began to form. In the case of explants with roots, they were transferred directly into soil. Rooted shoots were transferred to soil and hardened in a growth chamber for 2 to 3 weeks before transferring to the greenhouse. Regenerated plants obtained using this method were fertile and produced on average 500 seeds per plant.

After 5 days of co-cultivation with *Agrobacterium tumefaciens* transient expression of the gene of interest (GOI) was widespread on the seedling axillary meristem explants especially in the regions wounding during explant preparation (Method A). Explants were placed into shoot induction medium without selection to see how the primary-node responds to shoot induction and regeneration. Thus far, greater than 70% of the explants were formed new shoots at this region. Expression of the GOI was stable after 14 days on SIM, implying integration of the T-DNA into the soy genome. In addition, preliminary experiments resulted in the formation of cDNA expressing shoots forming after 3 weeks on SIM.

For Method C, the average regeneration time of a soy plantlet using the propagated axillary meristem protocol was 14 weeks from explant inoculation. Therefore, this method has a quick regeneration time that leads to fertile, healthy soy plants.

Example 4: Pathogen Assay 4.1. Growth of Plants

10 T1 plants per event were potted and grown for 3-4 weeks in the phytochamber (16 h-day-und 8 h-night-Rhythm at a temperature of 16 and 22° C. and a humidity of 75%) till the first 2 trifoliate leaves were fully expanded.

4.2 Inoculation

The plants were inoculated with *P. pachyrhizi.*

In order to obtain appropriate spore material for the inoculation, soybean leaves which had been infected with rust 15-20 days ago, were taken 2-3 days before the inoculation and transferred to agar plates (1% agar in H2O). The leaves were placed with their upper side onto the agar, which allowed the fungus to grow through the tissue and to produce very young spores. For the inoculation solution, the spores were knocked off the leaves and were added to a Tween-H2O solution. The counting of spores was performed under a light microscope by means of a Thoma counting chamber. For the inoculation of the plants, the spore suspension was added into a compressed-air operated spray flask and applied uniformly onto the plants or the leaves until the leaf surface is well moisturized. For macroscopic assays we used a spore density of 1-5×10$^5$ spores/ml. For the microscopy, a density of >5×10$^5$ spores/ml is used. The inoculated plants were placed for 24 hours in a greenhouse chamber with an average of 22° C. and >90% of air humidity. The following cultivation was performed in a chamber with an average of 25° C. and 70% of air humidity.

Example 5: Microscopical Screening

For the evaluation of the pathogen development, the inoculated leaves of plants were stained with aniline blue 48 hours after infection.

The aniline blue staining serves for the detection of fluorescent substances. During the defense reactions in host interactions and non-host interactions, substances such as phenols, callose or lignin accumulated or were produced and were incorporated at the cell wall either locally in papillae or in the whole cell (hypersensitive reaction, HR). Complexes were formed in association with aniline blue, which lead e.g. in the case of callose to yellow fluorescence. The leaf material was transferred to falcon tubes or dishes containing destaining solution II (ethanol/acetic acid 6/1) and was incubated in a water bath at 90° C. for 10-15 minutes. The destaining solution II was removed immediately thereafter, and the leaves were washed 2× with water. For the staining, the leaves were incubated for 1.5-2 hours in staining solution II (0.05% aniline blue=methyl blue, 0.067 M di-potassium hydrogen phosphate) and analyzed by microscopy immediately thereafter.

The different interaction types were evaluated (counted) by microscopy. An Olympus UV microscope BX61 (incident light) and a UV Longpath filter (excitation: 375/15, Beam splitter: 405 LP) are used. After aniline blue staining, the spores appeared blue under UV light. The papillae could be recognized beneath the fungal appressorium by a green/yellow staining. The hypersensitive reaction (HR) was characterized by a whole cell fluorescence.

Example 6: Evaluating the Susceptibility to Soybean Rust

The progression of the soybean rust disease was scored by the estimation of the diseased area (area which was covered by sporulating uredinia) on the backside (abaxial side) of the leaf. Additionally the yellowing of the leaf was taken into account (for scheme see FIG. 1).

At all 43 $T_1$ soybean plants (5 independent events, 7-10 transgenic plants each; expression of transgene checked by RT-PCR) expressing the CASAR protein were inoculated with spores of *Phakopsora pachyrhizi* The macroscopic disease symptoms caused by *P. pachyrhizi* on the inoculated soybean plants were scored 14 days after inoculation.

The average of the percentage of the leaf area showing fungal colonies or strong yellowing/browning on all leaves was considered as diseased leaf area. At all 43 soybean $T_1$ plants expressing CASAR (expression checked by RT-PCR) were evaluated in parallel to non-transgenic control plants of the same variety. Non-transgenic soy plants grown in parallel to the transgenic plants were used as control. The average of the diseased leaf area is shown in FIG. 7 for plants exogenously expressing CASAR compared with wildtype plants. Overexpression of CASAR reduces the diseased leaf area in comparison to non-transgenic control plants by 44.5% in average over all 5 independent events tested. This data clearly indicates that the in-planta expression of the CASAR expression vector construct lead to a lower disease scoring of transgenic plants compared to non-transgenic controls. So, the expression of CASAR (as shown in SEQ ID NO: 1) in soybean significantly ($p<0.001$) increases the resistance of soybean against soybean rust.

The invention claimed is:

1. A method for preventing, reducing, or delaying *Phakopsora* infection in a soybean plant, a soybean plant part, or a soybean plant cell, said method comprising:

providing a transgenic soybean plant, transgenic soybean plant part, or transgenic soybean plant cell with an exogenous nucleic acid encoding a *Capsicum annuum* systemic acquired resistance (CASAR) protein with at least 75% identity to SEQ ID NO:3, wherein the CASAR protein confers increased resistance against *Phakopsora* thereto in comparison to a wild type soybean plant, wild type soybean plant part or wild type soybean plant cell; and growing the transgenic soybean plant, transgenic soybean plant part, or transgenic soybean plant cell in the presence of a fungal pathogen of the genus *Phakopsora*, wherein *Phakopsora* infection is prevented, reduced, or delayed in the transgenic soybean plant, transgenic soybean plant part, or transgenic soybean plant cell as compared to a wild type soybean plant, wild type soybean plant part, or wild type soybean plant cell.

2. The method of claim 1, wherein the exogenous nucleic acid is in operable linkage with a promoter, and the promoter is a mesophyll-specific promoter having the nucleic acid sequence of SEQ ID NO: 4.

3. A recombinant vector construct comprising in operable linkage:

(a) (i) a nucleic acid comprising SEQ ID NO: 1 or 2; or (ii) a nucleic acid encoding a CASAR protein comprising an amino acid sequence having at least 75% identity with SEQ ID NO: 3;

(b) a rust-induced promoter and (c) a transcription termination sequence.

4. The vector construct of claim 3, wherein the promoter is a mesophyll-specific promoter having the nucleic acid sequence of SEQ ID NO: 4.

5. A method for the production of a transgenic soy plant, transgenic soy plant part, or transgenic soy plant cell having increased resistance against *Phakopsora*, said method comprising (a) introducing the recombinant vector construct of claim 3 into a soybean plant, a plant soybean part, or a soybean plant cell; and (b) regenerating a transgenic plant, transgenic plant part, or transgenic plant cell from the plant, plant part or plant cell.

6. The method of claim 5, further comprising the step of harvesting the seeds of the transgenic plant and planting the seeds and growing the seeds to plants, wherein the grown plants comprise the recombinant vector construct.

7. A transgenic soy plant, transgenic soy plant part, or transgenic soy plant cell comprising the recombinant vector construct of claim 3.

8. A part of a transgenic soy plant of claim 7, wherein the part comprises the recombinant vector construct.

9. The plant part of claim 8, wherein the part is a seed comprising the recombinant vector construct.

10. A method for the production of a product, said method comprising:

a) growing the transgenic soy plant of claim 7 and b) producing said product from the plant and/or a part thereof, where the product comprises the recombinant vector construct.

11. The method of claim 10, wherein said product is produced from seeds of the plant.

12. The method of claim 10, wherein the product is meal or oil.

13. A product derived from the transgenic soy plant of claim 7, wherein the product comprises the recombinant vector construct.

14. The product of claim 13, wherein the product is soybean meal or soy oil.

15. A method for breeding a rust resistant plant, said method comprising:

(a) crossing the transgenic soy plant of claim 7 with a second soy plant;

(b) obtaining seed from the cross of step (a);

(c) planting said seeds and growing the seeds to plants; and (d) selecting from the plants produced in step (c) plants expressing the CASAR protein, wherein the selected plants comprise the recombinant vector construct.

* * * * *